US011771823B2

(12) United States Patent
Turner et al.

(10) Patent No.: US 11,771,823 B2
(45) Date of Patent: *Oct. 3, 2023

(54) FLUID DELIVERY DEVICES, SYSTEMS AND METHODS

(71) Applicant: MEDTRONIC MINIMED, INC., Northridge, CA (US)

(72) Inventors: Brandon Turner, Austin, TX (US); John Burns, Austin, TX (US); Dan Benzon, Austin, TX (US); Adam Burnight, Austin, TX (US); Brian Highley, Keller, TX (US); Jason Adams, Frisco, TX (US); Kraig Kooiman, Flower Mound, TX (US); Clint Taylor, Addison, TX (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 992 days.

This patent is subject to a terminal disclaimer.

(21) Appl. No.: 16/460,565

(22) Filed: Jul. 2, 2019

(65) Prior Publication Data

US 2019/0388617 A1    Dec. 26, 2019

Related U.S. Application Data

(60) Division of application No. 14/722,106, filed on May 26, 2015, now Pat. No. 10,342,919, which is a (Continued)

(51) Int. Cl.
*A61M 5/158* (2006.01)
*A61M 5/168* (2006.01)
(Continued)

(52) U.S. Cl.
CPC ......... *A61M 5/1582* (2013.01); *A61K 9/0019* (2013.01); *A61K 9/0021* (2013.01); (Continued)

(58) Field of Classification Search
CPC .. A61M 2005/1581; A61M 2005/1587; A61M 5/168; A61M 5/162; A61M 39/04; (Continued)

(56) References Cited

U.S. PATENT DOCUMENTS 3,547,119 A    12/1970  Hall et al.
3,620,209 A    11/1971  Kravitz
(Continued)

FOREIGN PATENT DOCUMENTS

CA    1027540      10/1975
CN    2189466 Y    2/1995
(Continued)

OTHER PUBLICATIONS

"Insuflon" retrieved on Nov. 12, 2004 from http://www.poara.com/eng/insuflon/insuflon.htm.
(Continued)

*Primary Examiner* — Nathan R Price
*Assistant Examiner* — Anh Bui
(74) *Attorney, Agent, or Firm* — FORTEM IP LLP

(57) ABSTRACT

Fluid delivery devices, systems and methods. The fluid delivery devices may be used to delivery fluid (e.g., insulin) to a user. The devices may have one or more inlets, and may be configured for use with an injection device, such as a syringe, and/or with a pump.

16 Claims, 50 Drawing Sheets

Related U.S. Application Data division of application No. 13/557,026, filed on Jul. 24, 2012, now Pat. No. 9,039,660, which is a continuation of application No. 11/592,719, filed on Nov. 3, 2006, now Pat. No. 8,226,614.

(60) Provisional application No. 60/733,311, filed on Nov. 3, 2005.

(51) Int. Cl.
- A61M 39/02 (2006.01)
- A61K 9/00 (2006.01)
- A61M 39/04 (2006.01)
- A61M 5/162 (2006.01)
- A61M 5/32 (2006.01)

(52) U.S. Cl.
CPC ............ A61M 5/162 (2013.01); A61M 5/168 (2013.01); A61M 5/16804 (2013.01); A61M 39/0247 (2013.01); A61M 39/04 (2013.01); A61M 5/158 (2013.01); A61M 5/3202 (2013.01); A61M 2005/1581 (2013.01); A61M 2005/1587 (2013.01); A61M 2039/027 (2013.01); A61M 2039/0294 (2013.01)

(58) Field of Classification Search
CPC ...... A61M 39/0247; A61M 2039/0294; A61M 2039/027
See application file for complete search history.

(56) References Cited

U.S. PATENT DOCUMENTS

| | | |
|---|---|---|
| 4,311,137 A | 1/1982 | Gerard |
| 4,315,513 A | 2/1982 | Nawash et al. |
| 4,430,081 A | 2/1984 | Timmermans |
| 4,525,164 A | 6/1985 | Loeb et al. |
| 4,531,937 A | 7/1985 | Yates |
| 4,534,758 A | 8/1985 | Akers et al. |
| 4,568,335 A | 2/1986 | Updike et al. |
| 4,578,063 A | 3/1986 | Inman et al. |
| 4,675,006 A | 6/1987 | Hrushesky |
| 4,755,173 A | 7/1988 | Konopka et al. |
| 4,772,261 A | 9/1988 | Von Hoff et al. |
| 4,817,631 A | 4/1989 | Schnepp-Pesch et al. |
| 4,874,377 A | 10/1989 | Newgard et al. |
| 4,904,241 A | 2/1990 | Bark |
| 4,966,588 A | 10/1990 | Rayman et al. |
| 5,080,654 A | 1/1992 | Picha et al. |
| 5,092,849 A | 3/1992 | Sampson |
| 5,098,405 A * | 3/1992 | Peterson ............... A61M 39/02 604/246 |
| 5,108,377 A | 4/1992 | Cone et al. |
| 5,122,114 A | 6/1992 | Miller et al. |
| 5,176,653 A | 1/1993 | Metals |
| 5,176,662 A | 1/1993 | Bartholomew et al. |
| 5,257,980 A | 11/1993 | Van Antwerp et al. |
| 5,306,243 A | 4/1994 | Bonaldo |
| 5,332,398 A | 7/1994 | Miller et al. |
| 5,342,316 A | 8/1994 | Wallace |
| 5,370,625 A | 12/1994 | Shickman |
| 5,409,466 A | 4/1995 | Watson et al. |
| 5,522,803 A | 6/1996 | Teissen-Simony |
| 5,545,143 A | 8/1996 | Fischell |
| 5,545,152 A | 8/1996 | Fudnerburk et al. |
| 5,569,206 A | 10/1996 | Gorman et al. |
| 5,584,813 A | 12/1996 | Livingston et al. |
| 5,607,407 A | 3/1997 | Tolkoff et al. |
| 5,618,295 A | 4/1997 | Min |
| 5,647,851 A | 7/1997 | Pokras |
| 5,718,682 A | 2/1998 | Tucker |
| 5,727,770 A | 3/1998 | Dennis |
| 5,749,861 A | 5/1998 | Guala et al. |
| 5,797,879 A | 8/1998 | DeCampli |
| 5,839,895 A | 11/1998 | Fisburne |
| 5,848,989 A | 12/1998 | Villani |
| 5,851,197 A | 12/1998 | Marano et al. |
| 5,871,500 A | 2/1999 | Jepson et al. |
| 5,873,844 A | 2/1999 | Campero et al. |
| 5,925,017 A | 7/1999 | Kriesel et al. |
| 5,951,521 A | 9/1999 | Mastrototaro et al. |
| 5,954,684 A | 9/1999 | Flower et al. |
| 5,954,687 A | 9/1999 | Baudino |
| 5,968,011 A | 10/1999 | Larsen et al. |
| 5,980,506 A | 11/1999 | Mathiasen |
| 5,989,224 A | 11/1999 | Exline et al. |
| 6,017,328 A | 1/2000 | Fischell et al. |
| 6,056,718 A | 5/2000 | Funderburk et al. |
| 6,068,613 A | 5/2000 | Kriesel et al. |
| 6,074,371 A | 6/2000 | Fischell |
| 6,086,575 A | 7/2000 | Mejslov |
| 6,093,172 A | 7/2000 | Funderburk et al. |
| 6,110,154 A | 8/2000 | Shimomura et al. |
| 6,123,690 A | 9/2000 | Mejslov |
| 6,176,235 B1 | 1/2001 | Benarrouch et al. |
| 6,231,531 B1 | 5/2001 | Lum et al. |
| 6,254,586 B1 | 7/2001 | Mann et al. |
| 6,293,925 B1 | 9/2001 | Safabash et al. |
| 6,302,866 B1 | 10/2001 | Marggi |
| 6,344,033 B1 | 2/2002 | Jepson et al. |
| 6,355,021 B1 | 3/2002 | Nielsen et al. |
| 6,387,098 B1 | 5/2002 | Cole et al. |
| 6,413,244 B1 | 7/2002 | Bestetti et al. |
| 6,461,329 B1 | 10/2002 | Van Antwerp et al. |
| 6,488,663 B1 | 12/2002 | Steg |
| 6,520,938 B1 | 2/2003 | Funderburk et al. |
| 6,572,586 B1 | 6/2003 | Wojcik |
| 6,579,267 B2 | 6/2003 | Lynch et al. |
| 6,585,695 B1 | 7/2003 | Adair et al. |
| 6,602,229 B2 | 8/2003 | Coss |
| 6,629,949 B1 | 10/2003 | Douglas |
| 6,641,566 B2 | 11/2003 | Douglas et al. |
| 6,659,982 B2 | 12/2003 | Douglas et al. |
| 6,673,440 B2 | 1/2004 | Douglas et al. |
| 6,685,674 B2 | 2/2004 | Douglas et al. |
| 6,699,218 B2 | 3/2004 | Flaherty et al. |
| 6,702,761 B1 | 3/2004 | Damadian et al. |
| 6,736,797 B1 | 5/2004 | Larsen et al. |
| 6,749,587 B2 | 6/2004 | Flaherty |
| 6,749,589 B1 | 6/2004 | Douglas et al. |
| 6,805,693 B2 | 10/2004 | Gray et al. |
| 6,840,922 B2 | 1/2005 | Nielsen et al. |
| 6,908,459 B2 | 6/2005 | Harding et al. |
| 6,960,192 B1 | 11/2005 | Flaherty et al. |
| 6,964,649 B2 | 11/2005 | Goll |
| 7,008,383 B1 | 3/2006 | Damadian et al. |
| 7,022,108 B2 | 4/2006 | Marano-Ford et al. |
| 7,029,455 B2 | 4/2006 | Flaherty |
| 7,033,339 B1 | 4/2006 | Lynn |
| 7,083,597 B2 | 8/2006 | Lynch et al. |
| 7,303,543 B1 | 12/2007 | Mauel et al. |
| 7,309,326 B2 | 12/2007 | Fangrow, Jr. |
| 7,338,465 B2 | 3/2008 | Patton |
| 7,494,481 B2 | 2/2009 | Moberg et al. |
| 7,520,867 B2 | 4/2009 | Bowman et al. |
| 7,524,300 B2 | 4/2009 | Patton |
| 7,569,034 B2 | 8/2009 | Lynch et al. |
| 7,704,228 B2 | 4/2010 | Patton |
| 7,713,258 B2 | 5/2010 | Adams et al. |
| 7,731,680 B2 | 6/2010 | Patton |
| 7,892,216 B2 | 2/2011 | Fangrow, Jr. |
| 7,931,615 B2 | 4/2011 | Fangrow, Jr. |
| 7,935,090 B2 | 5/2011 | Patton |
| 8,216,208 B2 | 7/2012 | Patton |
| 8,221,361 B2 | 7/2012 | Patton |
| 8,221,362 B2 | 7/2012 | Patton |
| 8,221,386 B2 | 7/2012 | Patton |
| 8,226,614 B2 * | 7/2012 | Turner .................. A61M 5/162 604/164.04 |
| 8,262,627 B2 | 9/2012 | Patton |
| 8,366,683 B2 | 2/2013 | Patton |
| 8,551,047 B2 | 10/2013 | Burns et al. |
| 8,777,925 B2 | 7/2014 | Patton |

(56) References Cited

U.S. PATENT DOCUMENTS

| | | | |
|---|---|---|---|
| 9,486,575 | B2 | 11/2016 | Patton |
| 2001/0053887 | A1 | 12/2001 | Douglas et al. |
| 2001/0053889 | A1* | 12/2001 | Marggi .................. A61M 39/02 604/93.01 |
| 2001/0056064 | A1 | 12/2001 | Aoki |
| 2002/0045867 | A1 | 4/2002 | Nielsen et al. |
| 2002/0065484 | A1 | 5/2002 | Douglas et al. |
| 2002/0072720 | A1 | 6/2002 | Hague et al. |
| 2002/0072733 | A1 | 6/2002 | Flaherty |
| 2002/0107476 | A1 | 8/2002 | Mann et al. |
| 2002/0120231 | A1* | 8/2002 | Douglas ............ A61M 25/0097 604/82 |
| 2002/0123719 | A1 | 9/2002 | Lavi et al. |
| 2002/0123724 | A1 | 9/2002 | Douglas et al. |
| 2002/0123740 | A1 | 9/2002 | Flaherty et al. |
| 2002/0128600 | A1 | 9/2002 | Nissels |
| 2002/0151855 | A1 | 10/2002 | Douglas et al. |
| 2002/0161332 | A1 | 10/2002 | Ramey |
| 2002/0173769 | A1 | 11/2002 | Gray et al. |
| 2003/0023203 | A1 | 1/2003 | Lavi et al. |
| 2003/0073952 | A1 | 4/2003 | Flaherty et al. |
| 2003/0088238 | A1 | 5/2003 | Poulsen et al. |
| 2003/0097092 | A1 | 5/2003 | Flaherty |
| 2003/0100885 | A1 | 5/2003 | Pettis et al. |
| 2003/0114751 | A1 | 6/2003 | Pedain et al. |
| 2003/0176852 | A1 | 9/2003 | Lynch et al. |
| 2003/0199823 | A1 | 10/2003 | Bobroff et al. |
| 2003/0212364 | A1 | 11/2003 | Mann et al. |
| 2003/0213723 | A1 | 11/2003 | Lombardi |
| 2003/0216686 | A1 | 11/2003 | Lynch et al. |
| 2004/0001809 | A1 | 1/2004 | Brisken et al. |
| 2004/0002682 | A1 | 1/2004 | Kovelman et al. |
| 2004/0006316 | A1* | 1/2004 | Patton .................. A61M 5/162 604/288.02 |
| 2004/0015134 | A1 | 1/2004 | Lavi et al. |
| 2004/0030285 | A1 | 2/2004 | Lavi et al. |
| 2004/0073160 | A1 | 4/2004 | Pinkerton |
| 2004/0143216 | A1 | 7/2004 | Douglas et al. |
| 2004/0143241 | A1 | 7/2004 | Douglas et al. |
| 2004/0204687 | A1 | 10/2004 | Mogensen et al. |
| 2004/0204690 | A1 | 10/2004 | Yashiro et al. |
| 2004/0204691 | A1 | 10/2004 | Yashiro et al. |
| 2004/0260235 | A1 | 12/2004 | Douglas |
| 2004/0267238 | A1 | 12/2004 | Haarala et al. |
| 2005/0092387 | A1 | 5/2005 | Schorn et al. |
| 2005/0101910 | A1 | 5/2005 | Bowman et al. |
| 2005/0101933 | A1 | 5/2005 | Marrs et al. |
| 2005/0104473 | A1 | 5/2005 | Yoshida |
| 2005/0107743 | A1 | 5/2005 | Fangrow |
| 2005/0113761 | A1 | 5/2005 | Faust et al. |
| 2005/0240154 | A1 | 10/2005 | Mogensen et al. |
| 2006/0015076 | A1 | 1/2006 | Heinzerling et al. |
| 2006/0030815 | A1 | 2/2006 | Csincsura et al. |
| 2006/0129090 | A1 | 6/2006 | Moberg et al. |
| 2006/0173386 | A1 | 8/2006 | Lindquist |
| 2006/0217659 | A1 | 9/2006 | Patton |
| 2006/0264818 | A1 | 11/2006 | Patton |
| 2006/0264900 | A1 | 11/2006 | Patton |
| 2006/0264901 | A1 | 11/2006 | Patton |
| 2007/0049874 | A1 | 3/2007 | Patton |
| 2007/0049875 | A1 | 3/2007 | Patton |
| 2007/0049876 | A1 | 3/2007 | Patton |
| 2007/0049877 | A1 | 3/2007 | Patton |
| 2007/0088385 | A1 | 4/2007 | Perry |
| 2007/0093756 | A1 | 4/2007 | Patton |
| 2007/0093757 | A1 | 4/2007 | Patton |
| 2007/0219510 | A1 | 9/2007 | Zinn et al. |
| 2008/0021375 | A1 | 1/2008 | Burns |
| 2008/0045891 | A1 | 2/2008 | Maule et al. |
| 2008/0051714 | A1 | 2/2008 | Moberg et al. |
| 2009/0163878 | A1 | 6/2009 | Moberg et al. |

FOREIGN PATENT DOCUMENTS

| | | |
|---|---|---|
| CN | 2538364 Y | 3/2003 |
| CN | 1558782 A | 12/2004 |
| DE | 1991-12459 A1 | 9/2000 |
| DE | 1991-12459 C2 | 2/2001 |
| EP | 0239244 | 9/1987 |
| EP | 1 205 211 | 5/2002 |
| EP | 1566193 | 8/2005 |
| FR | 575559 | 8/1924 |
| FR | 2607012 | 5/1988 |
| GB | 1482052 | 8/1977 |
| JP | 59-118152 | 7/1984 |
| JP | 03-126438 | 5/1991 |
| WO | WO 87/01041 | 2/1987 |
| WO | WO 88/03816 | 6/1988 |
| WO | WO 92/20400 | 11/1992 |
| WO | WO 2002/040083 | 5/2002 |
| WO | WO 2005/049117 | 6/2005 |
| WO | WO 2006/097111 | 9/2006 |
| WO | WO 2007/040853 | 4/2007 |
| WO | WO 2007/056309 | 5/2007 |

OTHER PUBLICATIONS

Altman et al., "The Revised CONSORT Statement for Reporting Randomized Trials: Explanation and Elaboration," Annals Internal Medicine, 134:663-694, 2001.
American Diabetes Association "Standards of medical care for patients with diabetes mellitus." Diabetes Care, 25:213-29, 2002.
Anderson et al., "The use of an indwelling Teflon catheter for subcutaneous heparin administration during pregnancy. A randomized crossover study." Arch. Intern. Med., 153:841-4, 1993.
Chinese Search Report issued in Chinese Application No. 2006800475377, dated Aug. 27, 2012.
Dyer et al., "Insuflon Versus Subcutaneous Injection for Cytokine Administration in Children for Cytokine Administration in Children and Adolescents: A Randomized Crossover Study," J. Pediatric Oncology Nursing, 21:79-86, 2004.
English Translation of Office Action issued in Chinese Application No. 038158213, dated Jul. 6, 2007.
English Translation of Office Action issued in Chinese Application No. 038158213, dated Feb. 20, 2009.
English Translation of Office Action issued in Chinese Patent App. No. 03815821.3, dated Jun. 26, 2009.
English Translation of Office Action issued in Japanese Application No. 2004-519654, dated Apr. 28, 2008.
English Translation of Office Action issued in Japanese Application No. 2004-519654, dated Nov. 25, 2008.
Examination Report issued in Indian Patent Application No. 2424/DELNP/2008, dated Dec. 21, 2015.
Examination Report issued in Indian Patent Application No. 4282/DELNP/2008, dated Jan. 25, 2016.
Extended European Search Report issued in European Patent Application No. 06789895.7, dated Aug. 3, 2016.
FDA, Section 510(k) Notification for Viggo Insuflon, Aug. 24, 1998, Silver Spring, Maryland.
File History of U.S. Appl. No. 09/110,360, filed Jul. 6, 1998.
Final Rejection issued in U.S. Appl. No. 13/557,026, dated Sep. 18, 2014.
Final Rejection issued in U.S. Appl. No. 14/722,106, dated Jan. 23, 2018.
Final Rejection issued in U.S. Appl. No. 14/722,106, dated Oct. 1, 2018.
Graham et al.;"Control of Important Clinical Parameters for Patients with Type 2 Diabetes Mellitus," Diabetes,. 51:A-274, 2002 (Abstract No. 1112-P).
Hanas et al., "X-ray appearance of the indwelling catheter when using insuflon for insulin injections." Department of Pediatrics Uddevalla Hospital, Uddevalla, Sweden. Abstracts of the 17th Annual Meeting of ISGD, Hormone Research 35:58, 1991.
Hanas et al.; "Experience of Pain from Insulin Injections Using Syringes Pens and Indwelling Catheters." Department of Pediatrics, Uddevalla Hospital, Uddevalla Sweden. Abstract. 1989.

(56) References Cited

OTHER PUBLICATIONS

Hanas et al.; "Metabolic control is not altered when using indwelling catheters for insulin injections." Diabetes Care, 17:716-8, 1994.
Hanas et al.; "Side effects and indwelling times of subcutaneous catheters for insulin injections: a new device for injecting insulin with a minimum of pain in the treatment of insulin-dependent diabetes mellitus." Diabetes Res. Clin. Pract., 10:73-83, 1990.
Hanas et al.; "Unchanged insulin absorption after 4 days' use of subcutaneous indwelling catheters for insulin injections." Diabetes Care, 20:487-90, 1997.
Hanas, "Reducing injection pain in children and adolescents with diabetes: a review of indwelling catheters," Pediatric Diabetes, 5:102, 2004.
Heine, "A Randomized trial of continuous subcutaneous insulin infusion and intensive injection therapy in type 1 diabetes for patients with long-standing poor glycemic control," Diabetes Care, Nov. 1, 2002.
Henry et al., "Intensive conventional insulin therapy for type II diabetes. Metabolic effects during a 6-mo outpatient trial." Diabetes Care, 16:21-31, 1993.
Hunt et al. "NIDDM patients' fears and hopes about insulin therapy. The basis of patient reluctance." Diabetes Care, 20:292-8, 1997.
International Search Report and Written Opinion issued in PCT/US06/32609, dated Feb. 27, 2007.
International Search Report and Written Opinion issued in PCT/US06/43231, dated May 14, 2007.
Kaar et al., "Insulin Administration via a Subcutaneous Catheter: Effects on absorption," Diabetes Care, 16:1412-1413, 1993.
Knip et al., "No evidence of an accelerated absorption of exogenous insulin after using a subcutaneous catheter for 5 days in children with IDDM" Diabetes Care, June, 17:627, 1994.
Koro et al., "Glycemic control from 1988 to 2000 among U.S. adults diagnosed with type 2 diabetes: a preliminary report," Diabetes Care, 27:17-20, 2004.
Lamacraft et al., "Subcutaneous cannulae for morphine boluses in children: assessment of a technique," J. Pain Symptom Manage., 13:43-9, 1997.
Liu et al., "Insulin absorption is faster when keeping the infusion site in use for three days during continuous subcutaneous insulin infusion." Diabetes Res. Clin. Pract., 12:19-24, 1991.
Long and Hughes,. "Indwelling cannula for insulin administration in dibetes mellitus." Arch. Dis. Child, 66:348-9, 1991.
McGrath et al., "A new analogue scale for assessing children's pain: an initial validation study," Pain, Mar; 64:435-43, 1996.
Minutes of Oral Proceeds issued in European Patent Application No. 03739327.9, issued Apr. 4, 2013.
Notice of Allowance issued in U.S. Appl. No. 11/466,349, dated Jun. 6, 2013.
Notice of Allowance issued in U.S. Appl. No. 13/557,026, dated Jan. 22, 2015.
Notice of Allowance issued in U.S. Appl. No. 14/332,185, dated Jul. 7, 2016.
Notice of Allowance issued in U.S. Appl. No. 14/722,106, dated Feb. 22, 2019.
Notice of Allowance, issued in U.S. Appl. No. 11/483,218, dated Oct. 7, 2008.
Notice of Allowance, issued in U.S. Appl. No. 11/483,218, dated Feb. 10, 2009.
Office Action in Canadian App. No. 2,490,549, dated Feb. 23, 2010.
Office Action in Canadian Patent Application No. 2,490,549, dated Dec. 20, 2010.
Office Action in U.S. Appl. No. 11/372,681, dated May 6, 2010.
Office Action in U.S. Appl. No. 11/483,219, dated Dec. 16, 2010.
Office Action in U.S. Appl. No. 10/188,591, dated Dec. 15, 2005.
Office Action in U.S. Appl. No. 10/188,591, dated Dec. 15, 2006.
Office Action in U.S. Appl. No. 10/188,591, dated Feb. 27, 2006.
Office Action in U.S. Appl. No. 10/188,591, dated Jun. 7, 2006.
Office Action in U.S. Appl. No. 10/188,591, dated May 30, 2007.
Office Action in U.S. Appl. No. 10/188,591, dated Sep. 20, 2006.
Office Action in U.S. Appl. No. 11/372,681, dated Aug. 25, 2006.
Office Action in U.S. Appl. No. 11/372,681, dated Aug. 24, 2007.
Office Action in U.S. Appl. No. 11/372,681, dated Aug. 6, 2009.
Office Action in U.S. Appl. No. 11/372,681, dated Dec. 27, 2007.
Office Action in U.S. Appl. No. 11/372,681, dated Feb. 23, 2007.
Office Action in U.S. Appl. No. 11/372,681, dated Feb. 20, 2009.
Office Action in U.S. Appl. No. 11/372,681, dated May 1, 2008.
Office Action in U.S. Appl. No. 11/372,681, dated Nov. 20, 2009.
Office Action in U.S. Appl. No. 11/372,681, dated Sep. 12, 2008.
Office Action in U.S. Appl. No. 11/466,349 dated Jun. 12, 2009.
Office Action in U.S. Appl. No. 11/466,349, dated Nov. 6, 2009.
Office Action in U.S. Appl. No. 11/466,349, dated May 4, 2011.
Office Action in U.S. Appl. No. 11/482,265, dated Aug. 25, 2006.
Office Action in U.S. Appl. No. 11/482,265, dated Apr. 3, 2008.
Office Action in U.S. Appl. No. 11/482,265, dated Dec. 11, 2007.
Office Action in U.S. Appl. No. 11/482,265, dated Dec. 16, 2010.
Office Action in U.S. Appl. No. 11/482,265, dated Jan. 12, 2009.
Office Action in U.S. Appl. No. 11/482,265, dated Jun. 10, 2010.
Office Action in U.S. Appl. No. 11/482,265, dated May 30, 2007.
Office Action in U.S. Appl. No. 11/482,265, dated Nov. 30, 2006.
Office Action in U.S. Appl. No. 11/482,265, dated May 29, 2009.
Office Action in U.S. Appl. No. 11/482,265, dated Nov. 17, 2009.
Office Action in U.S. Appl. No. 11/483,219, dated Apr. 3, 2008.
Office Action in U.S. Appl. No. 11/483,219, dated Aug. 11, 2006.
Office Action in U.S. Appl. No. 11/483,219, dated Dec. 11, 2007.
Office Action in U.S. Appl. No. 11/483,219, dated Jan. 12, 2009.
Office Action in U.S. Appl. No. 11/483,219, dated Jun. 9, 2010.
Office Action in U.S. Appl. No. 11/483,219, dated May 30, 2007.
Office Action in U.S. Appl. No. 11/483,219, dated May 29, 2009.
Office Action in U.S. Appl. No. 11/483,219, dated Nov. 30, 2006.
Office Action in U.S. Appl. No. 11/483,219, dated Nov. 17, 2009.
Office Action in U.S. Appl. No. 11/532,747, dated Dec. 27, 2007.
Office Action in U.S. Appl. No. 11/532,747, dated Jun. 30, 2008.
Office Action in U.S. Appl. No. 11/532,747, dated Mar. 18, 2009.
Office Action in U.S. Appl. No. 11/532,747, dated Mar. 31, 2010.
Office Action in U.S. Appl. No. 11/532,747, dated Nov. 17, 2011.
Office Action in U.S. Appl. No. 11/532,747, dated Oct. 8, 2008.
Office Action in U.S. Appl. No. 11/532,747, dated Oct. 21, 2009.
Office Action in U.S. Appl. No. 11/532,772, dated Apr. 28, 2010.
Office Action in U.S. Appl. No. 11/532,772, dated Jan. 12, 2011.
Office Action in U.S. Appl. No. 11/532,772, dated Jun. 2, 2009.
Office Action in U.S. Appl. No. 11/532,772, dated Nov. 12, 2008.
Office Action in U.S. Appl. No. 11/532,772, dated Oct. 23, 2009.
Office Action in U.S. Appl. No. 11/532,824, dated Apr. 1, 2009.
Office Action in U.S. Appl. No. 11/532,824, dated May 12, 2010.
Office Action in U.S. Appl. No. 11/532,824, dated Oct. 22, 2009.
Office Action in U.S. Appl. No. 11/532,836, dated Aug. 6, 2009.
Office Action in U.S. Appl. No. 11/532,836, dated Feb. 20, 2009.
Office Action in U.S. Appl. No. 11/532,836, dated Jan. 29, 2008.
Office Action in U.S. Appl. No. 11/532,836, dated Jan. 11, 2011.
Office Action in U.S. Appl. No. 11/532,836, dated Jun. 27, 2008.
Office Action in U.S. Appl. No. 11/532,836, dated May 20, 2010.
Office Action in U.S. Appl. No. 11/532,836, dated Nov. 19, 2009.
Office Action in U.S. Appl. No. 11/532,836, dated Sep. 17, 2008.
Office Action in U.S. Appl. No. 11/532,845, dated Apr. 9, 2009.
Office Action in U.S. Appl. No. 11/532,845, dated Oct. 30, 2009.
Office Action in U.S. Appl. No. 11/532,858, dated Apr. 9, 2009.
Office Action in U.S. Appl. No. 11/532,858, dated Oct. 30, 2009.
Office Action in U.S. Appl. No. 11/592,719, dated Dec. 10, 2010.
Office Action in U.S. Appl. No. 11/592,719, dated Nov. 18, 2010.
Office Action in U.S. Appl. No. 11/592,719, dated Oct. 18, 2010.
Office Action in U.S. Appl. No. 12/042,206, dated Mar. 23, 2011.
Office Action in U.S. Appl. No. 12/042,206, dated Sep. 20, 2010.
Office Action in U.S. Appl. No. 12/042,212, dated Jan. 18, 2011.
Office Action in U.S. Appl. No. 11/372,681, dated Dec. 16, 2010.
Office Action in U.S. Appl. No. 11/483,218, dated Apr. 8, 2008.
Office Action in U.S. Appl. No. 11/483,218, dated Aug. 25, 2006.
Office Action in U.S. Appl. No. 11/483,218, dated Jul. 27, 2007.
Office Action in U.S. Appl. No. 11/483,218, dated Mar. 26, 2007.
Office Action in U.S. Appl. No. 11/483,218, dated Nov. 30, 2006.
Office Action issued 2011 in Australian Patent Application No. 2006311708, dated Sep. 22, 2011.
Office Action issued in Australian Patent Application No. 2013206380, dated Nov. 24, 2014.

(56) References Cited

OTHER PUBLICATIONS

Office Action Issued in Australian Patent Application No. 2015258342, dated Aug. 22, 2016.
Office Action issued in Australian Patent Application No. 2015258342, dated May 10, 2017.
Office Action issued in Australian Patent Application No. 2015258342, dated Jul. 3, 2017.
Office Action issued in Chinese Application No. 2006800475377, dated Oct. 29, 2010.
Office Action issued in Chinese Application No. 2006800475377, dated Jul. 13, 2011.
Office Action issued in Chinese Patent Application No. 200680038075.2, dated Nov. 23, 2010.
Office Action issued in Chinese Patent Application No. 200680038075.2, dated Feb. 29, 2012.
Office Action issued in Chinese Patent Application No. 200680038075.2, dated Mar. 4, 2013.
Office Action issued in Chinese Patent Application No. 200680038075.2, dated Jan. 14, 2014.
Office Action issued in European Patent Application No. 03739327.9, dated Apr. 9, 2012.
Office Action issued in European Patent Application No. 03739327.9, dated Sep. 24, 2014.
Office Action issued in European Patent Application No. 03739327.9, dated Sep. 21, 2015.
Office Action issued in New Zealand Patent Application No. 566773, dated Oct. 9, 2009.
Office Action issued in New Zealand Patent Application No. 567891, dated Nov. 9, 2009
Office Action issued in Russian Application No. 2008110940, dated Jun. 11, 2010.
Office Action issued in Russian Patent Application No. 2008122063, dated Oct. 5, 2010.
Office Action issued in U.S. Appl. No. 11/466,349, dated Jul. 21, 2011
Office Action issued in U.S. Appl. No. 13/557,026, dated Apr. 4, 2014.
Office Action Issued in U.S. Appl. No. 14/332,185, dated Dec. 17, 2014.
Office Action issued in U.S. Appl. No. 14/332,185, dated Apr. 8, 2015.
Office Action issued in U.S. Appl. No. 14/332,185, dated Aug. 20, 2015.
Office Action issued in U.S. Appl. No. 14/332,185, dated May 2, 2016.
Office Action issued in U.S. Appl. No. 14/722,106, dated Nov. 9, 2017.
Office Action issued in U.S. Appl. No. 14/722,106, dated May 16, 2018.
Office Communication issued in Mexican Patent Application No. MX/a/2012/009448, dated Feb. 25, 2014. (Machine Translation).
Record of Examiner Interview issued in European Patent Application No. 03739327.9, dated Apr. 3, 2017.
Response to Final Office Action filed in U.S. Appl. No. 14/722,106, dated Mar. 23, 2018.
Response to Final Office Action issued in U.S. Appl. No. 14/722,106, dated Nov. 13, 2018.
Response to Final Rejection issued in U.S. Appl. No. 13/557,026, dated Dec. 16, 2014.
Response to Office Action filed in U.S. Appl. No. 13/557,026, dated Jul. 8, 2014.
Response to Office Action filed in U.S. Appl. No. 14/722,106, dated Nov. 10, 2017.
Response to Office Action filed in U.S. Appl. No. 14/722,106, dated Jun. 12, 2018.
Response to Office Action in U.S. Appl. No. 10/188,591, dated Jan. 19, 2006.
Response to Office Action in U.S. Appl. No. 10/188,591, dated Mar. 13, 2006.
Response to Office Action in U.S. Appl. No. 10/188,591, dated Sep. 1, 2006.
Response to Office Action in U.S. Appl. No. 10/188,591, dated Sep. 26, 2006.
Response to Office Action in U.S. Appl. No. 10/188,591, dated Mar. 15, 2007.
Response to Office Action in U.S. Appl. No. 10/188,591, dated Sep. 28, 2007.
Response to Office Action in U.S. Appl. No. 11/372,681, dated Nov. 27, 2006.
Response to Office Action in U.S. Appl. No. 11/372,681, dated Jun. 25, 2007.
Response to Office Action in U.S. Appl. No. 11/372,681, dated Nov. 26, 2007.
Response to Office Action in U.S. Appl. No. 11/372,681, dated Mar. 20, 2008.
Response to Office Action in U.S. Appl. No. 11/372,681, dated Aug. 1, 2008.
Response to Office Action in U.S. Appl. No. 11/372,681, dated Dec. 18, 2008.
Response to Office Action in U.S. Appl. No. 11/372,681, dated May 20, 2009.
Response to Office Action in U.S. Appl. No. 11/372,681, dated Sep. 8, 2009.
Response to Office Action in U.S. Appl. No. 11/372,681, dated Mar. 22, 2010.
Response to Office Action in U.S. Appl. No. 11/372,681, dated Nov. 5, 2010.
Response to Office Action in U.S. Appl. No. 11/372,681, dated Apr. 12, 2011.
Response to Office Action in U.S. Appl. No. 11/466,349, dated Sep. 14, 2009.
Response to Office Action in U.S. Appl. No. 11/466,349, dated Mar. 8, 2010.
Response to Office Action in U.S. Appl. No. 11/482,265, dated Sep. 15, 2006.
Response to Office Action in U.S. Appl. No. 11/482,265, dated Feb. 28, 2007.
Response to Office Action in U.S. Appl. No. 11/482,265, dated Sep. 12, 2007.
Response to Office Action in U.S. Appl. No. 11/482,265, dated Mar. 20, 2008.
Response to Office Action in U.S. Appl. No. 11/482,265, dated Oct. 3, 2008.
Response to Office Action in U.S. Appl. No. 11/482,265, dated Apr. 13, 2009.
Response to Office Action in U.S. Appl. No. 11/482,265, dated Aug. 31, 2009.
Response to Office Action in U.S. Appl. No. 11/482,265, dated Apr. 19, 2010.
Response to Office Action in U.S. Appl. No. 11/482,265, dated Nov. 9, 2010.
Response to Office Action in U.S. Appl. No. 11/482.265, dated Apr. 12, 2011.
Response to Office Action in U.S. Appl. No. 11/482,218, dated Sep. 15, 2006.
Response to Office Action in U.S. Appl. No. 11/483,218, dated Feb. 28, 2007.
Response to Office Action in U.S. Appl. No. 11/483,218, dated May 10, 2007.
Response to Office Action in U.S. Appl. No. 11/483,218, dated Aug. 4, 2008.
Response to Office Action in U.S. Appl. No. 11/483,219, dated Sep. 15, 2006.
Response to Office Action in U.S. Appl. No. 11/483,219, dated Feb. 28, 2007.
Response to Office Action in U.S. Appl. No. 11/483,219, dated Sep. 12, 2007.
Response to Office Action in U.S. Appl. No. 11/483,219, dated Mar. 20, 2008.
Response to Office Action in U.S. Appl. No. 11/483,219, dated Oct. 3, 2008.

(56) References Cited

OTHER PUBLICATIONS

Response to Office Action in U.S. Appl. No. 11/483,219, dated Apr. 13, 2009.
Response to Office Action in U.S. Appl. No. 11/483,219, dated Aug. 31, 2009.
Response to Office Action in U.S. Appl. No. 11/483,219, dated Apr. 19, 2010.
Response to Office Action in U.S. Appl. No. 11/483,219, dated Nov. 9, 2010.
Response to Office Action in U.S. Appl. No. 11/483,219, dated Apr. 12, 2011.
Response to Office Action in U.S. Appl. No. 11/532,747, dated Mar. 20, 2008.
Response to Office Action in U.S. Appl. No. 11/532,747, dated Aug. 4, 2008.
Response to Office Action in U.S. Appl. No. 11/532,747, dated Mar. 9, 2009.
Response to Office Action in U.S. Appl. No. 11/532,747, dated Jul. 17, 2009.
Response to Office Action in U.S. Appl. No. 11/532,747, dated Mar. 22, 2010.
Response to Office Action in U.S. Appl. No. 11/532,747, dated Sep. 30, 2010.
Response to Office Action in U.S. Appl. No. 11/532,747, dated Apr. 12, 2011.
Response to Office Action in U.S. Appl. No. 11/532,772, dated Mar. 12, 2009.
Response to Office Action in U.S. Appl. No. 11/532,772, dated Sep. 8, 2009.
Response to Office Action in U.S. Appl. No. 11/532,772, dated Mar. 23, 2010.
Response to Office Action in U.S. Appl. No. 11/532,772, dated Oct. 28, 2010.
Response to Office Action in U.S. Appl. No. 11/532,772, dated Apr. 11, 2011.
Response to Office Action in U.S. Appl. No. 11/532,824, dated Jul. 1, 2009.
Response to Office Action in U.S. Appl. No. 11/532,824, dated Mar. 22, 2010.
Response to Office Action in U.S. Appl. No. 11/532,824, dated Oct. 12, 2010.
Response to Office Action in U.S. Appl. No. 11/532,836, dated Mar. 20, 2008.
Response to Office Action in U.S. Appl. No. 11/532,836, dated Aug. 4, 2008.
Response to Office Action in U.S. Appl. No. 11/532,836, dated Dec. 17, 2008.
Response to Office Action in U.S. Appl. No. 11/532,836, dated May 20, 2009.
Response to Office Action in U.S. Appl. No. 11/532,836, dated Sep. 8, 2009.
Response to Office Action in U.S. Appl. No. 11/532,836, dated Apr. 19, 2010.
Response to Office Action in U.S. Appl. No. 11/532,836, dated Nov. 22, 2010.
Response to Office Action in U.S. Appl. No. 11/532,836, dated Apr. 12, 2011.
Response to Office Action in U.S. Appl. No. 11/532,845, dated Jul. 9, 2009.
Response to Office Action in U.S. Appl. No. 11/532,845, dated Feb. 1, 2010.
Response to Office Action in U.S. Appl. No. 11/532,858, dated Jul. 9, 2009.
Response to Office Action in U.S. Appl. No. 11/532,858, dated Feb. 1, 2010.
Response to Office Action in U.S. Appl. No. 11/5992,719, dated Apr. 11, 2011.
Response to Office Action in U.S. Appl. No. 12/042,206, dated Jan. 20, 2011.
Response to Office Action in U.S. Appl. No. 12/042,212, dated Apr. 18, 2011.
Response to Office Action issued in U.S. Appl. No. 11/466,349, dated Dec. 21, 2011.
Response to Office Action issued in U.S. Appl. No. 11/466,349, dated Sep. 19, 2012.
Response to Office Action Issued in U.S. Appl. No. 14/332,185, dated Mar. 17, 2015.
Response to Office Action issued in U.S. Appl. No. 14/332,185, dated Aug. 10, 2015.
Response to Office Action issued in U.S. Appl. No. 14/332,185, dated Jan. 8, 2016.
Response to Office Action issued in U.S. Appl. No. 14/332,185, dated Jun. 16, 2016.
Response to Office Action, in U.S. Appl. No. 11/483,218, dated Jan. 7, 2009.
Response to Office Action, in U.S. Appl. No. 11/483,218, dated Jan. 6, 2008.
Selam and Charles, "Devices for insulin administration." Diabetes Care, 13:955-79, 1990.
Su et al., "The Relationship between Regimen Burden and Psychological Well Being in Persons with Type 1 Diabetes: Inhaled vs Injectable Insulin," American Diabetes Association 62nd Annual Meeting and Scientific Sessions, San Francisco, CA, Jun. 14-18, 2002 (Abstract No. 1843-P, p. A448).
Summons to Attend Oral Proceedings issued in European Patent Application No. 03739327.9, issued Aug. 9, 2016.
Supplementary Search Report issued in European Patent Application No. 03739327.9, dated Jul. 5, 2012.
Taddio et al., "Use of lidocaine-priolcaine cream for vaccination pain in infants," J. Pediatr., 124:643-648, 1994.
Testa et al., "Patient satisfaction with insulin therapy in type 2 diabetes: a randomized trial of injectable vs. inhaled insulin." American Diabetes Association 62nd Annual Meeting and Scientific Sessions, Jun. 14-18, 2002, San Francisco, CA, US.
Text of Office Action, in Japanese App. No. 2004-519654, dated Oct. 16, 2009. (English translation).
Zambanini et al., "Injection related anxiety in insulin-treated diabetes." Diabetes Res. Clin. Pract., 46:239-46, 1999.

* cited by examiner

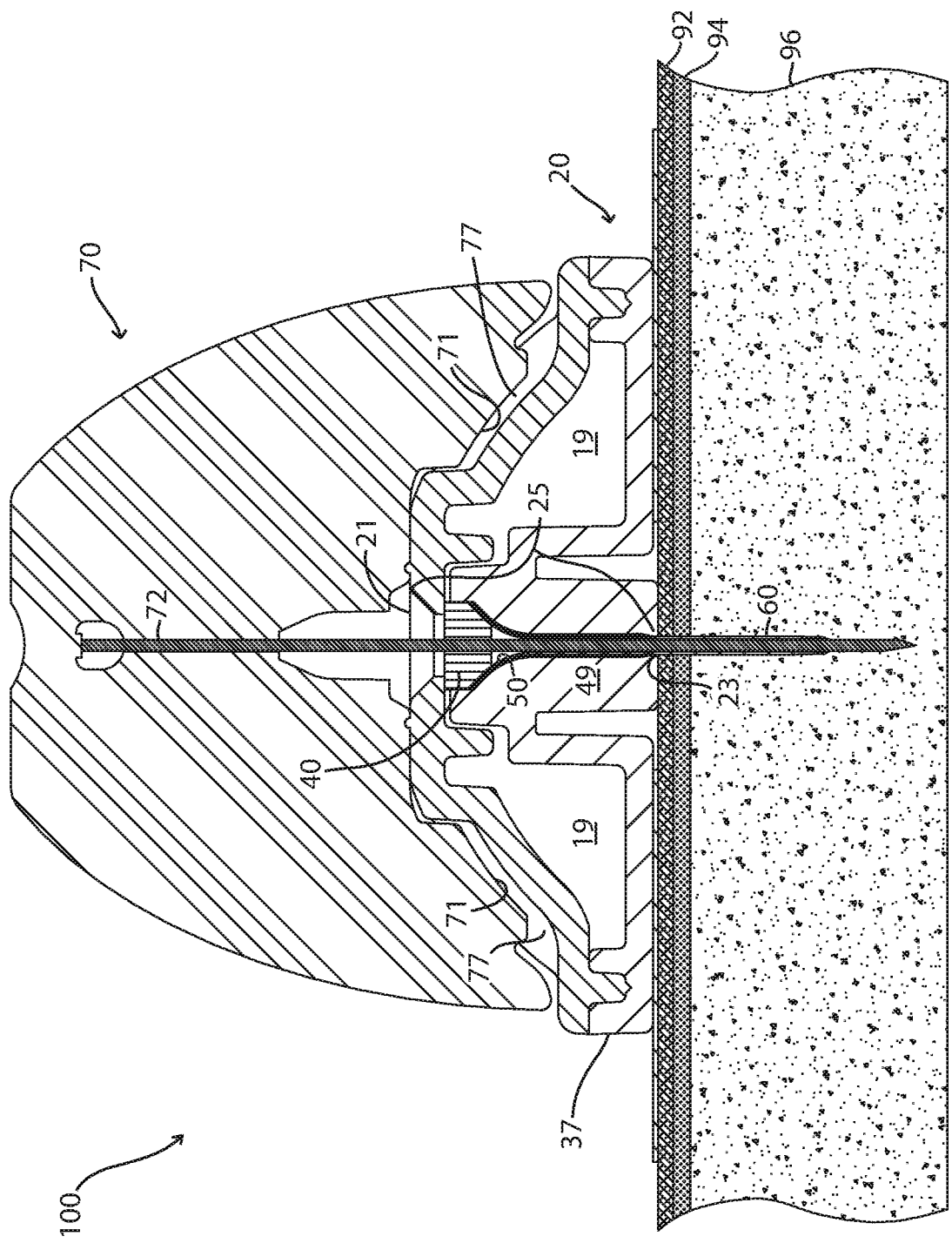

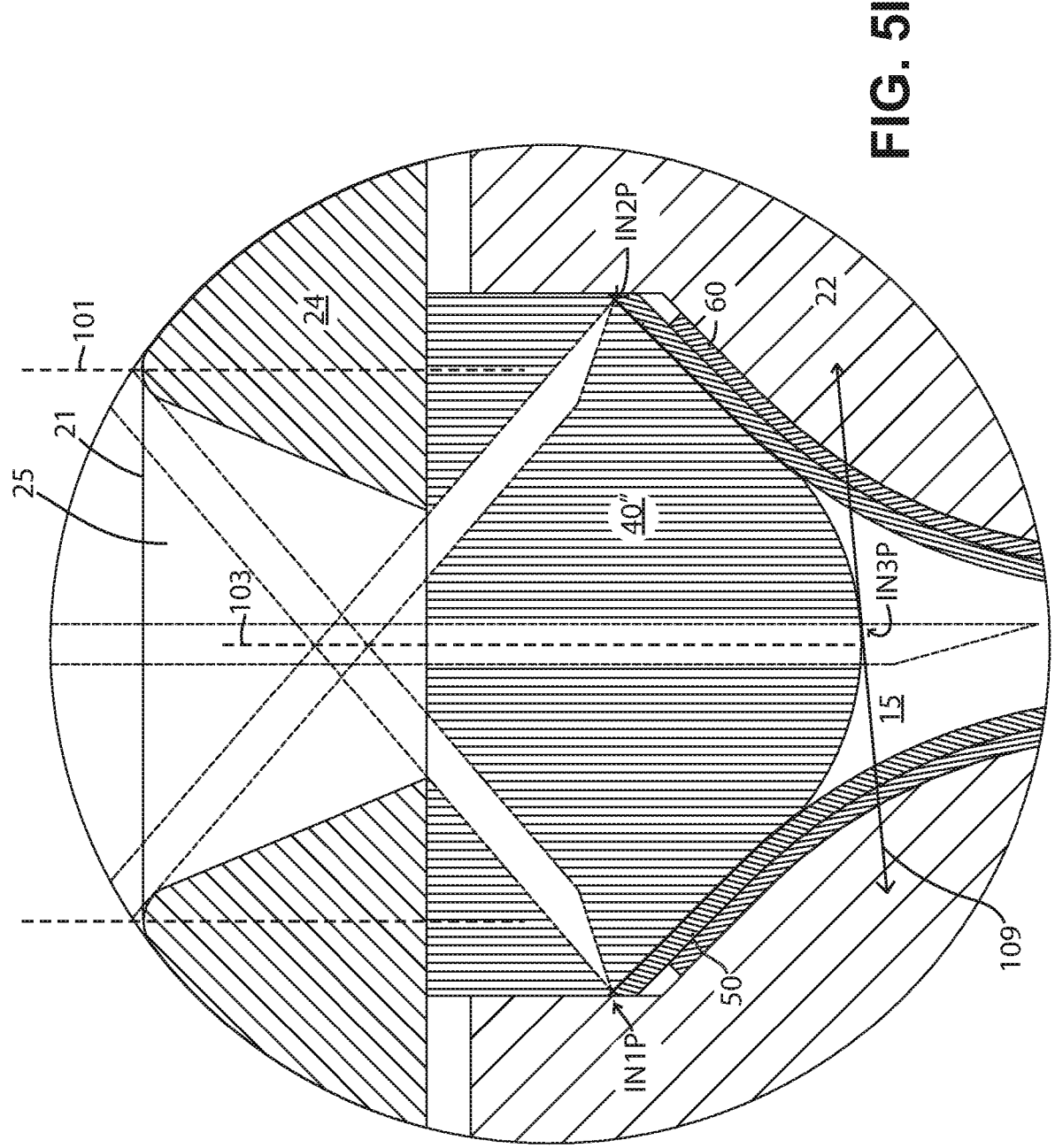

FLUID DELIVERY DEVICES, SYSTEMS AND METHODS

CROSS-REFERENCE(S) TO RELATED APPLICATION(S)

This is a division of co-pending U.S. application Ser. No. 14/722,106, filed May 26, 2015, which is a division of co-pending U.S. application Ser. No. 13/557,026, now U.S. Pat. No. 9,039,660, filed Jul. 24, 2012, which is a continuation of U.S. application Ser. No. 11/592,719, now U.S. Pat. No. 8,226,614, filed Nov. 3, 2006, which claims priority to U.S. Provisional Patent Application Ser. No. 60/733,311 filed Nov. 3, 2006, all of which are incorporated by reference without disclaimer.

BACKGROUND OF THE INVENTION

1. Field of the Invention

The invention relates generally to devices that can be inserted in and attached to a living being for the purpose of facilitating the introduction of a fluid, such as medicine, into the living being. The invention also relates to systems that include one or more such devices, and to methods of delivering fluid into a living being.

2. Description of Related Art

Examples of devices that can be used to deliver fluids to a living being include: U.S. Pat. Nos. 4,755,173; 4,966,588; 5,968,011; 6,017,328; 6,056,718; 6,074,371; 6,685,674; 6,736,797; U.S. Patent Application Pub. Nos. 2002/0072720; 2004/0006316; 2005/0101910; 2005/0107743; and abandoned Ser. No. 09/110,360 (incorporated by reference in U.S. Pat. No. 6,074,371).

SUMMARY OF THE INVENTION

Some embodiments of the present fluid delivery devices, systems and methods may be used to deliver fluid such as insulin to users such as people with diabetes. Some embodiments of the present fluid delivery devices may be configured to be worn for an extended period of time (e.g., multiple days) and allow a user to inject a fluid (such as a physician-prescribed drug) into the user's body without the need to repeatedly puncture the user's skin with a needle. The present fluid delivery devices, systems and methods include many different features that distinguish them from prior devices, and certain of those features are different in many ways from the features of prior devices. Different embodiments of the present fluid delivery devices, systems and methods include one or more of these features, which are interchangeable between embodiments to the extent that they are not inconsistent with the other features of a given embodiment.

Some embodiments of the present fluid delivery devices include, broadly, a body, a cannula, a needle guide, and a septum. The body may be made from one or more pieces, such as two pieces. The body may include one or more fluid delivery passageways. One or more of the fluid delivery passageways may be oriented at a non-parallel angle to the normal direction of installation of the device. In some embodiments that include two or more fluid delivery passageways, one the of the passageways may extend into and be angled with respect to another. In some multi-fluid delivery passageway embodiments, the devices also may include a passageway closing structure that at least partially blocks one of the passageways in a first position and another of the passageways in a second position. The passageway or passageways that are not blocked in a given position may remain at least partially unobstructed and, more preferably, substantially unobstructed. In some embodiments, the passageway closing structure may be actuated or shifted between positions by an injection device, such as an injection needle. In some multi-fluid delivery passageway embodiments, some or all of the fluid delivery passageways may be defined in part by a fitting adapted to be releasably coupled to an infusion pump connector fitting. Thus, in such embodiments, the device may allow for fluid delivery from a pump and fluid delivery from another structure, such as a syringe.

The cannula and the body of the devices may be integrally formed, such that the cannula comprises a tube-like structure that extends outwardly from the body (e.g., from the bottom surface of the body). The devices also may include an insertion device that is coupled to the body and that may be used to aid in insertion of the device, and a needle guard that is coupled to the body and that may be used to protect users from inadvertent needle sticks. In some embodiments of the present fluid delivery devices, a rigid cannula may be used instead of a needle guide and a soft cannula.

Some embodiments of the present systems (which may be characterized as fluid delivery systems) include one or more of the present fluid delivery devices that have been sterilized and enclosed in a package, with or without instructions for use contained within the package.

Some embodiments of the present methods (which may be characterized as fluid delivery methods) include installing one of the present fluid delivery devices to a user, and delivering fluid through the device and into the user.

BRIEF DESCRIPTION OF THE DRAWINGS

The following drawings illustrate by way of example and not limitation. Identical reference numbers do not necessarily indicate an identical structure. Rather, the same reference number may be used to indicate a similar feature or a feature with similar functionality, as may non-identical reference numbers. Every feature of each embodiment is not always labeled in every figure in which that embodiment appears, in order to keep the figures clear. The figures are drawn to scale, meaning the sizes of the depicted elements are accurate relative to each other for at least one set of embodiments of the present fluid delivery devices.

FIG. 4 is a cross-sectional view of the fluid delivery device shown in FIG. 1, taken along a plane that intersects the middle of both rotation-restricting recesses of the base element of the body, showing the device installed to a user. Most of the background lines shown in FIG. 3 have been eliminated from this figure (and from the remaining figures) in an effort to make the figure easier to review.

FIGS. 5H-5J show enlarged detail views of cross sections of a portion of different embodiments of the present fluid delivery devices.

DESCRIPTION OF ILLUSTRATIVE EMBODIMENTS

Figure 1:
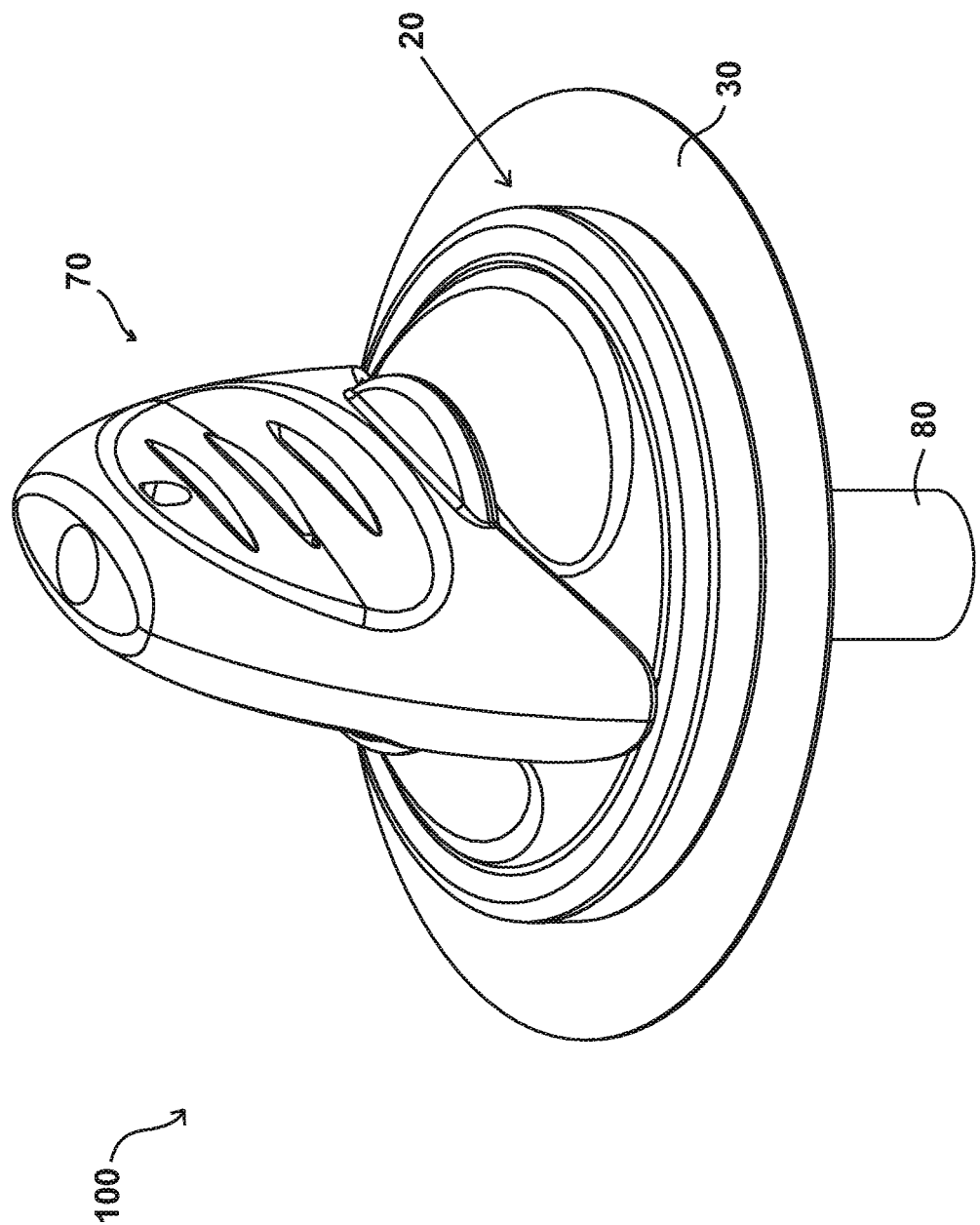
FIG. 1 is a perspective view of one embodiment of the present fluid delivery devices.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device, a system or a method that "comprises," "has," "contains," or "includes" one or more recited elements or steps possesses those recited elements or steps, but is not limited to possessing only those elements or steps; it may possess elements or steps that are not recited. Likewise, an element of a device, system or method that "comprises," "has," "contains," or "includes" one or more recited features possesses those features, but is not limited to possessing only those features; it may possess features that are not recited. Furthermore, a structure that is configured in a certain way must be configured in at least that way, but also may be configured in a way or ways that are not specified.

Thus, and by way of example, a fluid delivery device comprising a body having a first inlet, a first fluid delivery passageway extending from the first inlet, and a second fluid delivery passageway; a cannula having a portion that is coaxial with a portion of one of the first and second fluid delivery passageways; and a passageway closing structure oriented in a first position that substantially prevents fluid from flowing from the first inlet through the first fluid delivery passageway and out of the body, while allowing fluid to flow through the second fluid delivery passageway; the passageway closing structure being movable to a second position that substantially prevents fluid from flowing through the second fluid delivery passageway while allowing fluid to flow through the first fluid delivery passageway, is a fluid delivery device that possesses the recited body, cannula, and passageway closing structure, but is not limited to possessing only the recited elements (thus, other non-recited elements are not excluded). For example, the fluid delivery device also may include one or more septa.

Furthermore, the elements recited are not limited to possessing only the recited features. For example, the passageway closing structure may pivot about an axis that is centered within a portion of one of the fluid delivery passageways. As another example, an axis that is centered within or parallel to a portion of a passageway is one that is centered within or parallel to at least the portion, and may be centered within or parallel to the entire passageway. Similarly, a structure (e.g., a needle guide) "having" a portion positioned within a fluid delivery passageway has at least the portion positioned in the passageway, and may be positioned entirely within the passageway.

In any of the claims, the term "consisting of" or "consisting essentially of" may be substituted for any of the open-ended linking verbs recited above, in order to change the scope of a given claim from what it would otherwise be using the open-ended linking verb.

The terms "a" and "an" are defined as one or more than one unless this disclosure explicitly requires otherwise. The terms "substantially" is defined as at least close to (and includes) a given value or state (preferably within 10% of, more preferably within 1% of, and most preferably within 0.1% of).

The present fluid delivery devices may be used to deliver fluid to a living being for any of a variety of reasons. For example, some embodiments of the present fluid delivery devices may be used to deliver insulin to the subcutaneous tissue of a person with diabetes. However, embodiments of the present fluid delivery devices also may be used to deliver other fluids, such as saline, medication other than insulin, chemicals, enzymes, antigens, hormones, vitamins or the like, into subcutaneous tissue or other types of tissue, such as the epidermis, dermis, and different types of sub-dermal tissue such as muscle. The embodiments of the present fluid delivery devices shown in the figures are adapted for use with humans; however, those of ordinary skill in the art will, in light of this disclosure, understand that other embodiments may be adapted for use with animals.

The present fluid delivery devices may be characterized as ports, fluid delivery ports, injection ports, injection aides, infusion ports or infusion devices. The present fluid delivery systems may be characterized as injection systems or infusion systems.

FIG. 1 is a perspective view of one embodiment of the present fluid delivery devices. Fluid delivery device 100 includes a multi-piece body 20, an insertion device 70 that is coupled to body 20 at a first location, and a needle guard 80 that is coupled to body 20 at a second location. Device 100 also includes a generically-depicted adhesive layer 30 (which may include a protective backing sheet). Adhesive layer 30 may include a pad having two opposing, adhesive-coated sides, one of which is attached to the relevant portion of the bottom surface of body 20 and the other of which will be attached to a user's body (e.g., once a backing sheet has been removed). Alternatively, one of the two opposing sides may be welded (e.g., ultrasonically welded) to the bottom surface of body 20 instead of being attached via an adhesive. As opposed to using an adhesive layer, a portion (e.g., all) of the bottom surface of body 20 may be configured to adhere directly to a living being's skin, such as by making the bottom surface material from a material that chemically reacts with and adheres to skin. Adhesive layer 30 is one example of an adhesive portion (of a fluid delivery device) that is configured to adhere directly to a living being's skin. The cannula of device 100 (see cannula 60 in FIG. 3) is example of a cannula having a portion extending from the adhesive portion.

Figure 2A:
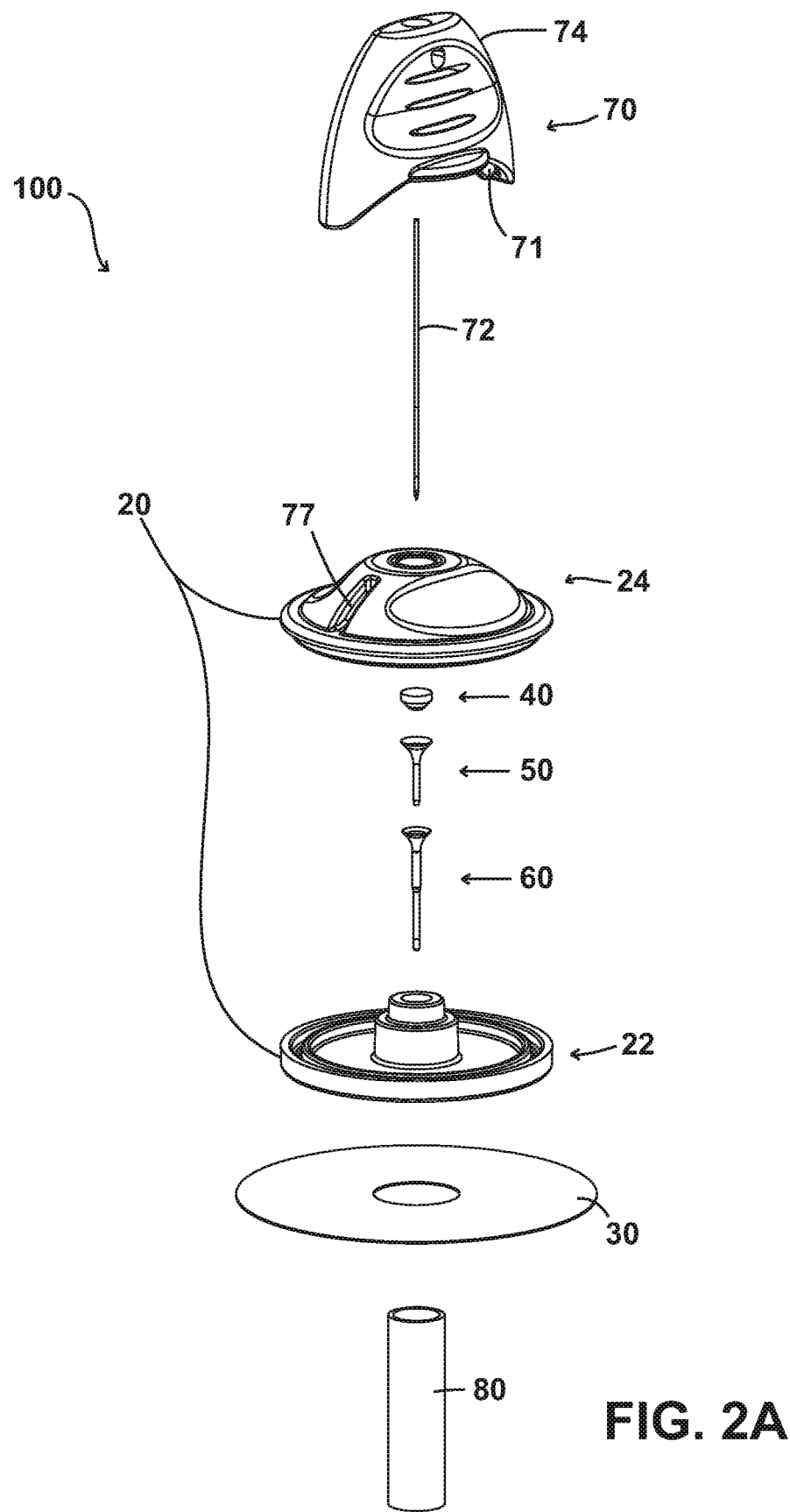
FIGS. 2A and 2B are exploded views of the fluid delivery device show in FIG. 1. The views are taken from different perspectives.
Figure 2B:
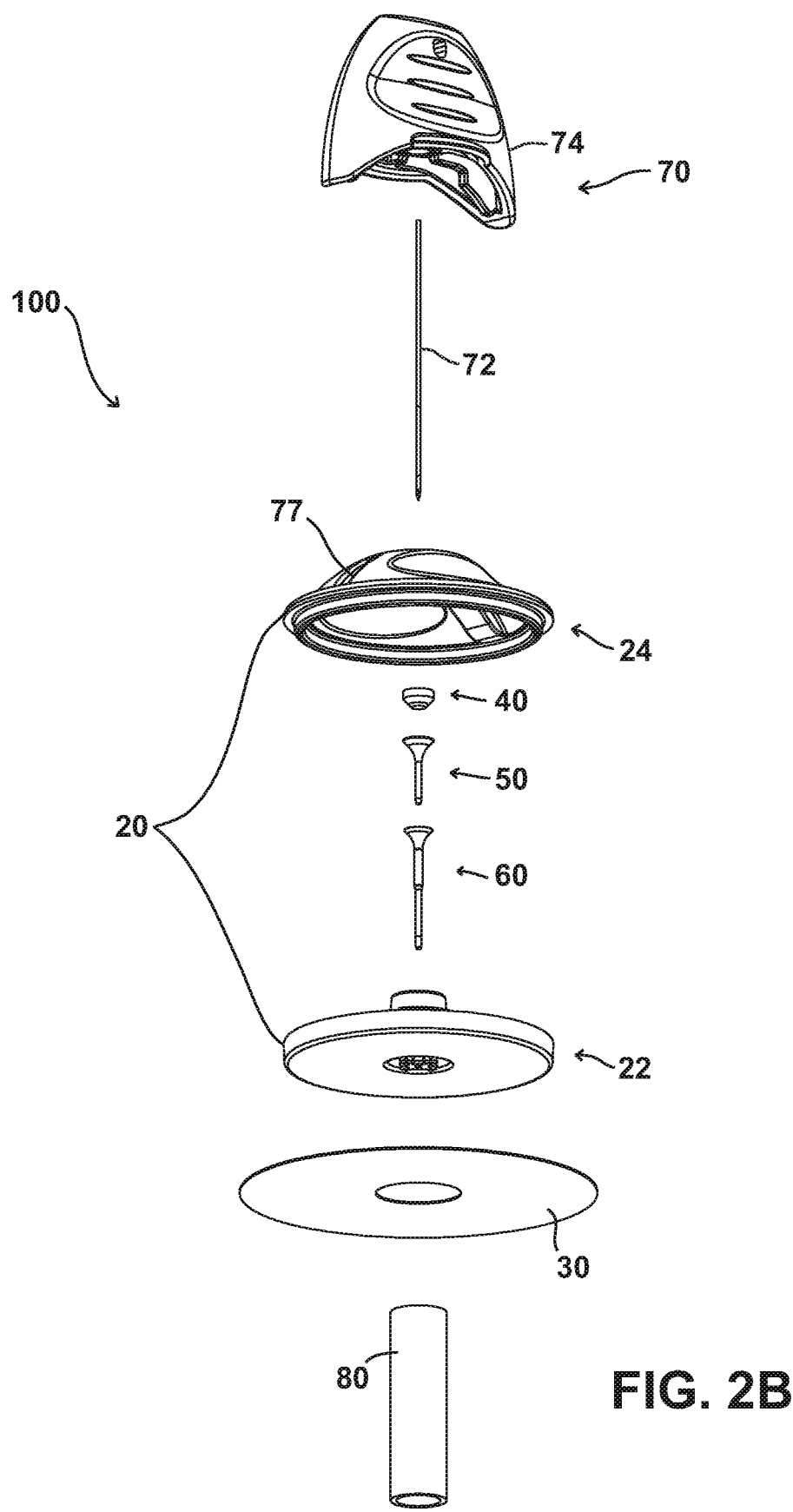

FIGS. 2A and 2B are exploded perspective views of the components of one embodiment of fluid delivery device 100. As these figure show, body 20 may include a first element 22 (which may be characterized as a base element) and a second element 24 (which may be characterized as a top element or a cap element). Device 100 also may include a septum 40, a needle guide 50, and a cannula 60. Septum 40 is one type of sealing mechanism.

Figure 3:
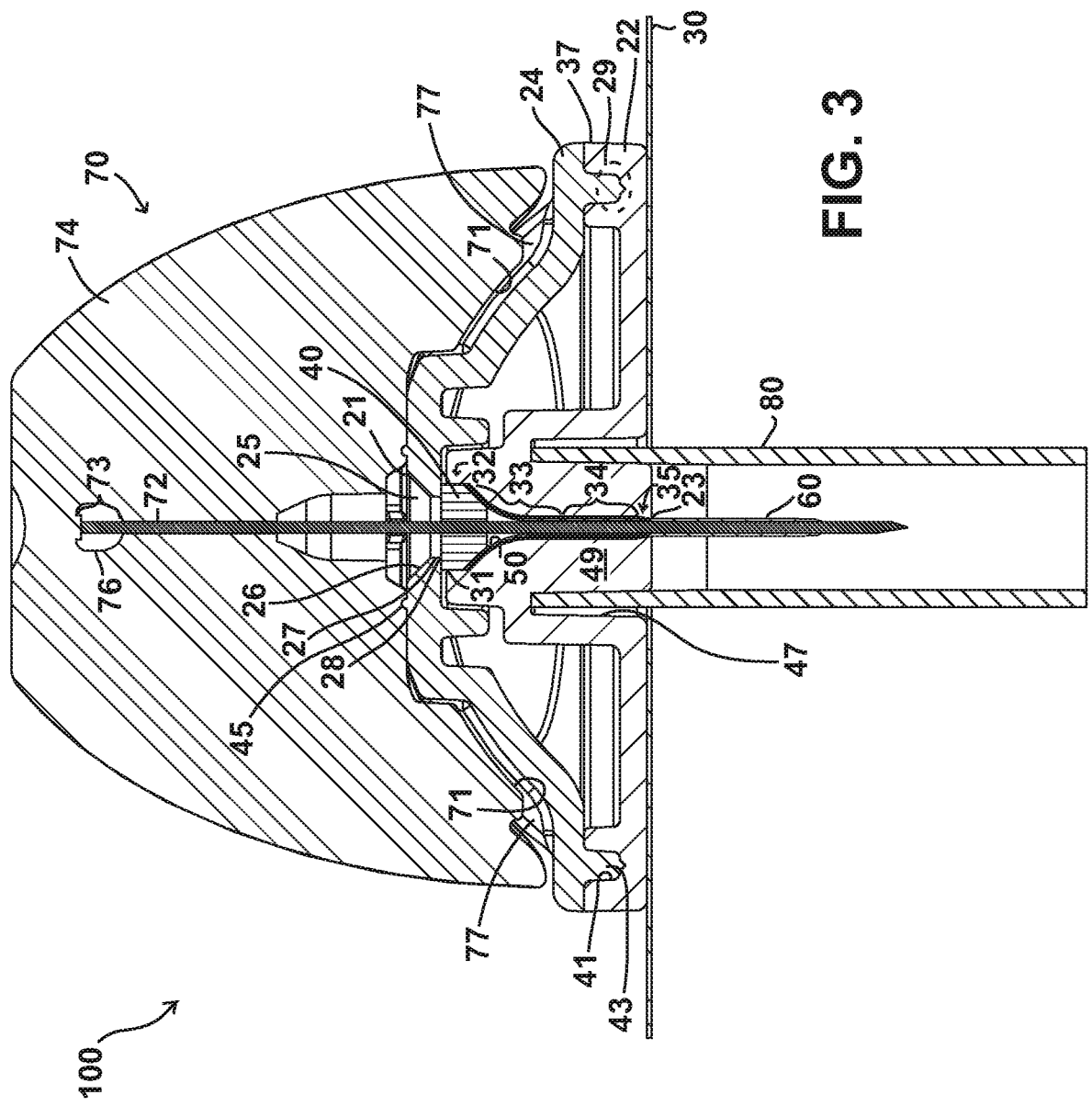
FIG. 3 is a cross-sectional view of the fluid delivery device shown in FIG. 1, taken along a plane that intersects the middle of both rotation-restricting recesses of the base element of the body.

Insertion device 70 comprising an insertion needle 72 connected to an insertion device hub 74. As shown in FIG. 3, a portion 73 of insertion needle 72 is located above the bottom surface of body 20 and is exposed when insertion device 70 is fully inserted in body 20. One manner in which this exposure is accomplished is by providing insertion device hub 74 with an insertion needle access region 76 that allows access to portion 73 when insertion device 70 is fully inserted in body 20. In other embodiments, insertion needle 72 could be configured such that portion 73 extends outwardly to a side of hub 74, such that no access region is needed. Still other embodiments that allow access to a portion of insertion needle 73 are possible. In the embodiment shown in the figures, the insertion needle access region comprises an opening that extends from one side of the hub to the other. In other embodiments involving an access region, the access region comprises a recess that extends from one side of the hub to (but not beyond) a portion of the insertion needle. The access region may be located anywhere along the hub, and need not be closer to the top of hub 74 than the bottom of hub 74 (as is the depicted access region).

Body 20 and insertion device 70 may be configured such that insertion device 70 cannot rotate with respect to body 20 when fully inserted in body 20. One manner of achieving this configuration comprises providing hub 74 with rotation-restricting protrusions 71, which extend in a downstream or downward direction from the main portion of insertion device hub 74, and by providing cap element 24 of body 20 with rotation-restricting recesses 77. When insertion device 70 is fully inserted in body 20, as shown in FIG. 3, at least a portion of each protrusion 71 extends into each recess 77 such that the recess side walls interfere with the protrusions to prevent rotation of the insertion device relative to body 20. Although the embodiment shown includes two protrusions and two recesses, other embodiments may include fewer or greater numbers of each.

Body 20 includes a fluid delivery passageway 25, which extends from entrance opening 21 (which also may be characterized as inlet port 21, or inlet 21) in cap element 24 through exit opening 23 in base element 22. Cap element 24 includes a portion 26 that tapers inwardly, or in a downstream direction, and extends from entrance opening 21 to a straight-walled portion 27 ("straight" meaning that, in this embodiment, the portion has no bend and a constant diameter), which extends to the bottom surface of cap element 24 and terminates at cap element exit opening 28. The portion of cap element 24 that overlaps an outer portion of septum 40 may be characterized as a sealing mechanism-retaining shoulder, or a septum retaining shoulder. Base element 22 includes a base element entrance opening 31 from which a straight-walled portion 32 extends. Straight-walled portion 32 ends at tapered wall portion 33, which extends into another straight-walled portion 34. Straight-walled portion 34 extends into a tapered portion 35 that ends at exit opening 23. Fluid delivery passageway 25 is characterized by all of these portions and openings.

FIG. 3 shows that cap element 24 is permanently attached to base element 22 at a location 29 that is closer to the outer perimeter 37 of body 20 than to the center of the body (which is not numbered, but which runs through the center of insertion needle 72). Location 29 is where the portions of cap element attachment protrusion 43 and base element attachment recess 41 are joined together as a result of the permanent attachment. If ultrasonic welding is used, which is one suitable technique, the bottom of the protrusion 43 and the lowest part of the recess 41 comprise location 29. The energy director that is shown in FIG. 3 proximate location 29 is eliminated by the ultrasonic welding. Two elements, or pieces, that are "permanently attached" to each other are attached such that a user of the device will not be able to separate them without destroying or significantly impairing the usefulness of the device. An alternative way to achieve this type of permanent attachment is through the use of an adhesive or adhesives. Other welding techniques that may be used include but are not limited to laser welding, hot plate welding, vibration welding, and friction welding.

In this embodiment, location 29 lies in a plane (not shown) that is substantially perpendicular to an axis (not shown) that is parallel to a portion of fluid delivery passageway 25. (The axis also is parallel to a portion of the cannula passageway of cannula 60.) The plane also may be characterized as being, in this embodiment, parallel to the bottom surface of body 20. The plane may be referred to as a device plane, and it is a plane in which the two body elements—cap element 24 and base element 22—may be assembled.

FIG. 3 shows that body 20, and more specifically cap element 24, may include a fluid delivery passageway identification feature 45 that is positioned near entrance opening 21 of body 20. Such an identification feature may help a user to locate the inlet port of the body more quickly, especially if the identification feature stands out in some way from the remainder of the body, such as by its color, by being a protrusion (as in the embodiment of the identification feature in the figures), or by being recessed. The identification feature can encircle entrance opening 21, as shown, or it may not. As FIG. 3 shows, insertion device hub 74 may be provided with a complimentary identification feature configuration (e.g., a recess, as shown, but not labeled) that compliments or otherwise fits with identification feature 45.

FIG. 3 shows one way that body 20 and needle guard 80 may be coupled to each other. Base element 22 may include a needle guard holding recess 47 that is configured to accept a top portion of needle guard 80 such that needle guard 80 may be held to body through a friction fit, or any other suitable means of engagement.

Cannula 60 of fluid delivery device 100 has a portion (specifically, an upper portion in the depicted embodiment) positioned within fluid delivery passageway 25. Cannula 60 has a portion that is substantially coaxial with a portion of fluid delivery passageway 25. More specifically, in the depicted embodiment, cannula 60 is coaxial with fluid delivery passageway 25. Needle guide 50 has a portion (specifically, all in the depicted embodiment) positioned within fluid delivery passageway 25 and also within cannula 60 (or the cannula passageway of cannula 60). Needle guide 50 has a portion that is substantially coaxial with a portion of fluid delivery passageway 25. More specifically, in the depicted embodiment, needle guide 50 is coaxial with fluid delivery passageway 25. Needle guide 50 also has a portion that is substantially coaxial with a portion of cannula 60. More specifically, in the depicted embodiment, needle guide 50 is coaxial with cannula 60 (or the cannula passageway).

FIG. 4 shows a cross-sectional view of fluid delivery device 100 installed to a living being. The "installation" of one of the present fluid delivery devices to a living being or a user refers to the process by which a portion of the cannula is inserted below the outer surface of the skin. The device, and more specifically the bottom surface (unnumbered) of adhesive layer 30, comprises an engagement surface that engages, or is in contact with, the skin of a living being when the device is installed to a living being. This figure shows that at least a portion (and, in this embodiment, all) of fluid delivery passageway 25 (as characterized by an axis (not shown) running through it from inlet port 21 to exit opening 23) is substantially perpendicular to the engagement surface of the device.

This figure, like FIG. 3, also shows that the end of insertion needle 72 extends slightly below the end of cannula 60 because the insertion needle is responsible for piercing the user's body tissue, which includes epidermis 92, dermis 94 and subcutaneous tissue 96. The portion of cannula 60 that is downstream of the end of needle guide 50 fits snugly around insertion needle 72 for the purpose of reducing the likelihood that the cannula will buckle, crimp or bend as the fluid delivery device is installed to a user. The friction between the lower portion of the cannula passageway and the outer surface of insertion needle 72 contributes to the reduction in that likelihood. That friction may be increased by grit blasting the insertion needle using any suitable material. Although not shown, the lowermost end of cannula 60 may terminate coincident with insertion needle 72 and be configured with the same angle of taper as insertion needle 72 to further the reduction in that likelihood. As FIG. 4 shows, cannula 60 is positioned such that any portion of it that is above the user's skin when fluid delivery device 100 is used (or is inserted into the living being) is positioned within outer perimeter 37 of body 20. If the bottom of central portion 49 stopped above epidermis 92 instead of resting against epidermis 92, cannula 60 would be positioned such that any exposed portion of it that is above the user's skin when fluid delivery device 100 is used (or is inserted into the living being) would be positioned within outer perimeter 37 of body 20. Stated another way, body 20 is configured and cannula 60 is positioned such that any portion (e.g., any exposed portion) of cannula 60 that is above the user's skin when fluid delivery device 100 is used (or is inserted into the living being) is positioned within outer perimeter 37 of body 20.

Figure 5A:
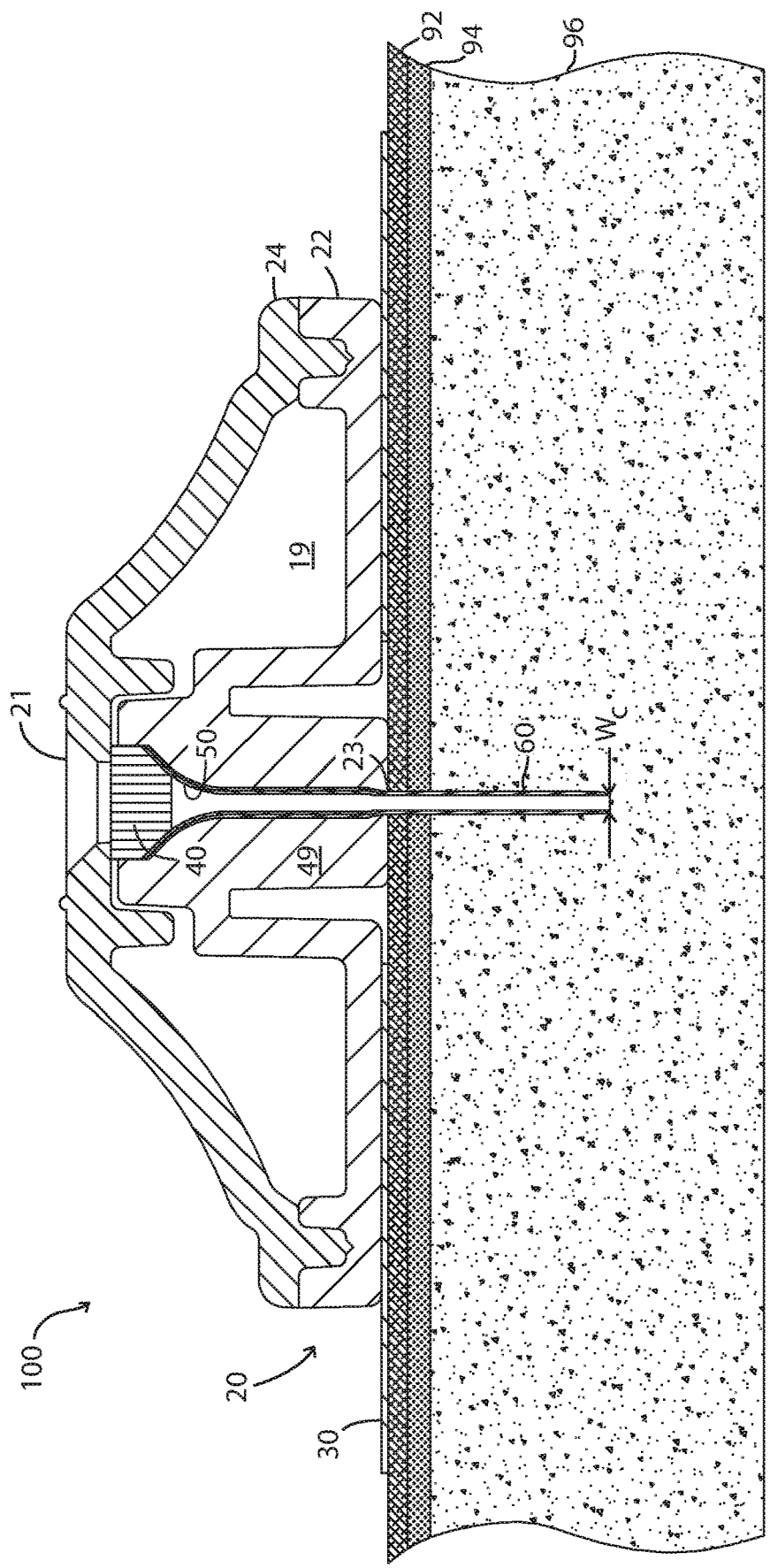
FIG. 5A is a cross-sectional view of the fluid delivery device shown in FIG. 1, taken along a plane that is perpendicular to the plane along which the FIG. 3 and FIG. 4 cross sections were taken, showing the device installed to a user and the insertion device removed.

FIG. 5A shows an embodiment of fluid delivery device 100 installed to a living being. Insertion device 70 has been removed. FIG. 5A also shows that fluid delivery device 100 is configured such that fluid exiting fluid delivery device 100 and into a living body must exit fluid delivery device 100 through cannula 60. Although there is a small gap visible in this and other figures between cap element 24 and base element 22 near septum 40, the small gap is effectively eliminated when the cap element 24 is permanently attached to base element 22 and septum 40 is compressed.

FIG. 5A shows that in some embodiments of the present fluid delivery devices, the bottommost portion of the septum located within the fluid delivery passageway (bottom surface 44 of septum 40, in the depicted embodiment) is closer to the inlet port than to the bottom surface of the body. More specifically, FIG. 5A shows an embodiment of the present fluid delivery devices in which the bottommost portion of the septum located within the fluid delivery passageway is closer to the plane (not shown) in which the inlet port is positioned than to the bottommost portion (or the plane (not shown) in which the bottommost portion is positioned) of the body, which bottommost portion comprises the bottom of central portion 49 of base element 22 in the depicted embodiment.

FIG. 5A also shows that in some embodiments of the present fluid delivery devices, the bottommost portion of the septum located within the fluid delivery passageway is closer to the inlet port than the exit port (exit opening 23, in this embodiment) of the body. More specifically, FIG. 5A shows an embodiment of the present fluid delivery devices in which the bottommost portion of the septum located within the fluid delivery passageway is closer to the plane (not shown) in which the inlet port is positioned than to the plane (not shown) in which the exit port of the body is positioned. A space (e.g., open space) or a structure (e.g., a portion of a structure such as a septum or a needle guide) can be within a fluid delivery passageway even though there is a structure or structures (e.g., a needle guide and/or a cannula) in between the space/structure and the material defining the fluid delivery passageway.

As shown in FIGS. 3-5A, body 20 includes a cavity within cap element 24 and base element 22 comprising open space 19. Body 20 is sealed against fluid entering this open space by virtue of the permanent attachment between the two elements at location 29 and the compression seal that each element creates with septum 40. Open space 19 may be characterized as non-fluid delivery passageway open space within body 20.

Figure 5B:
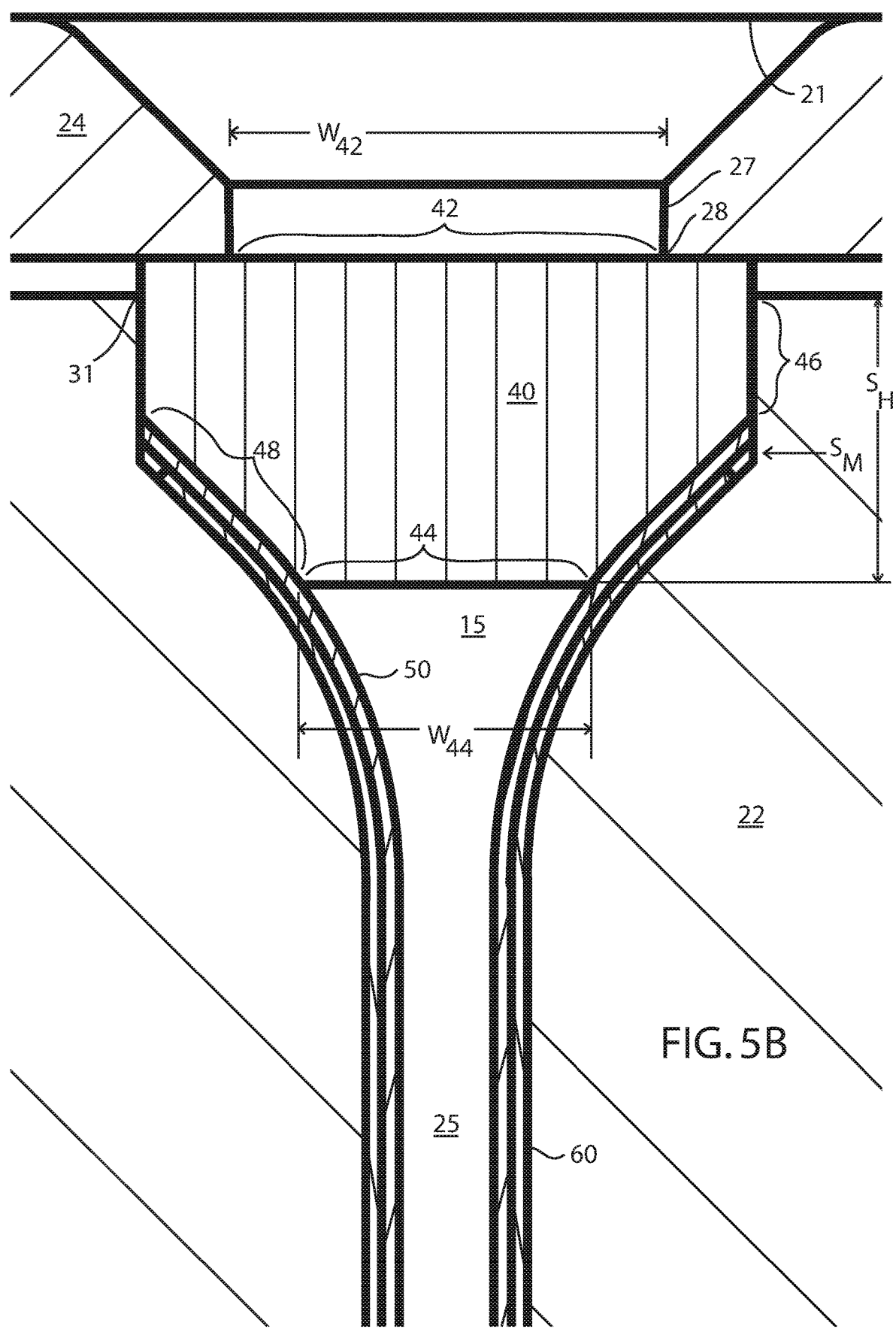
FIG. 5B is an enlarged detail view of a portion of the FIG. 5A view, showing aspects of one of the present septa.
Figure 5C:
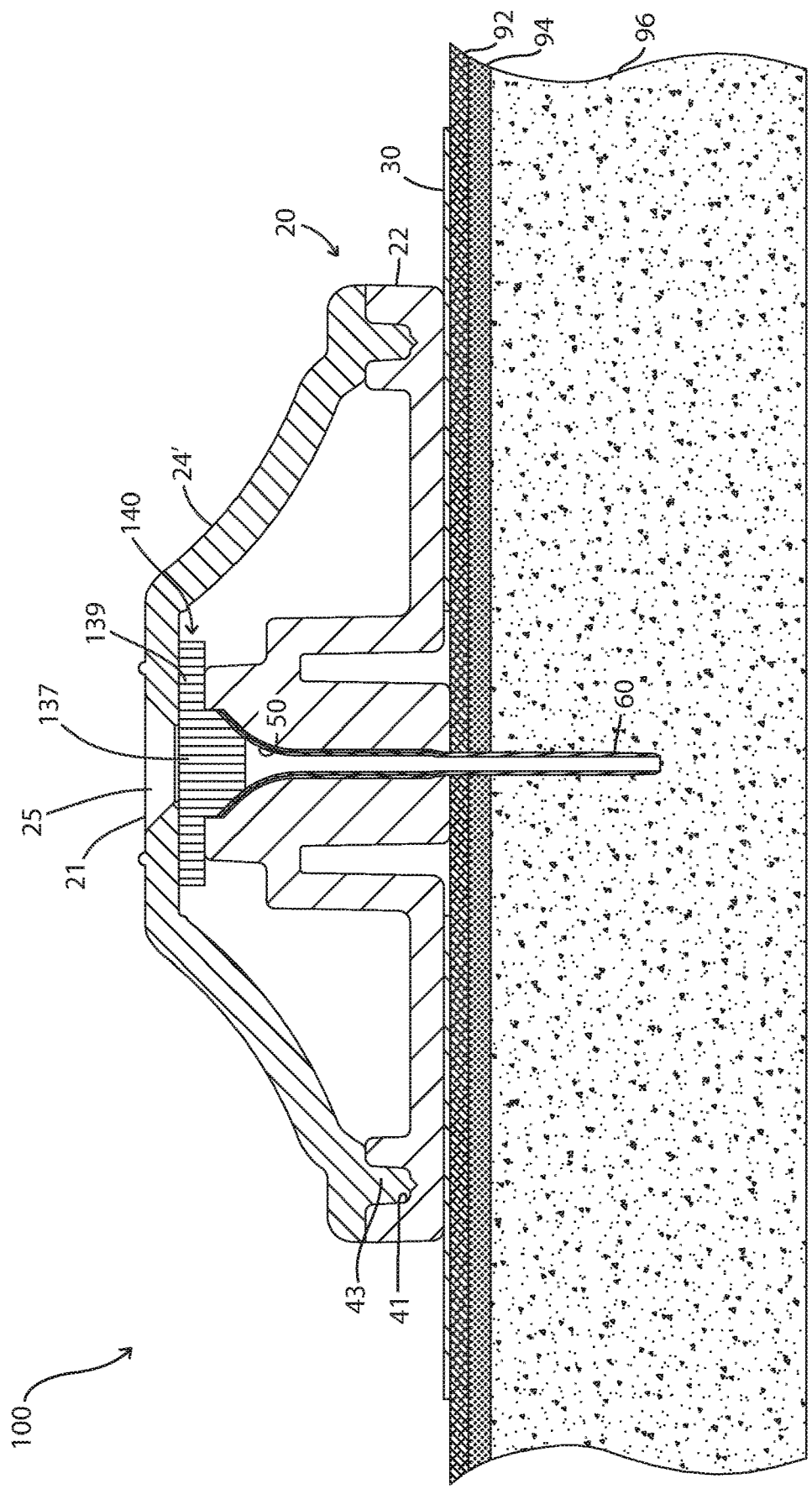
FIG. 5C is a cross-sectional view of an embodiment of the FIG. 1 fluid delivery device that includes a septum having a retention flange.
Figure 5D:
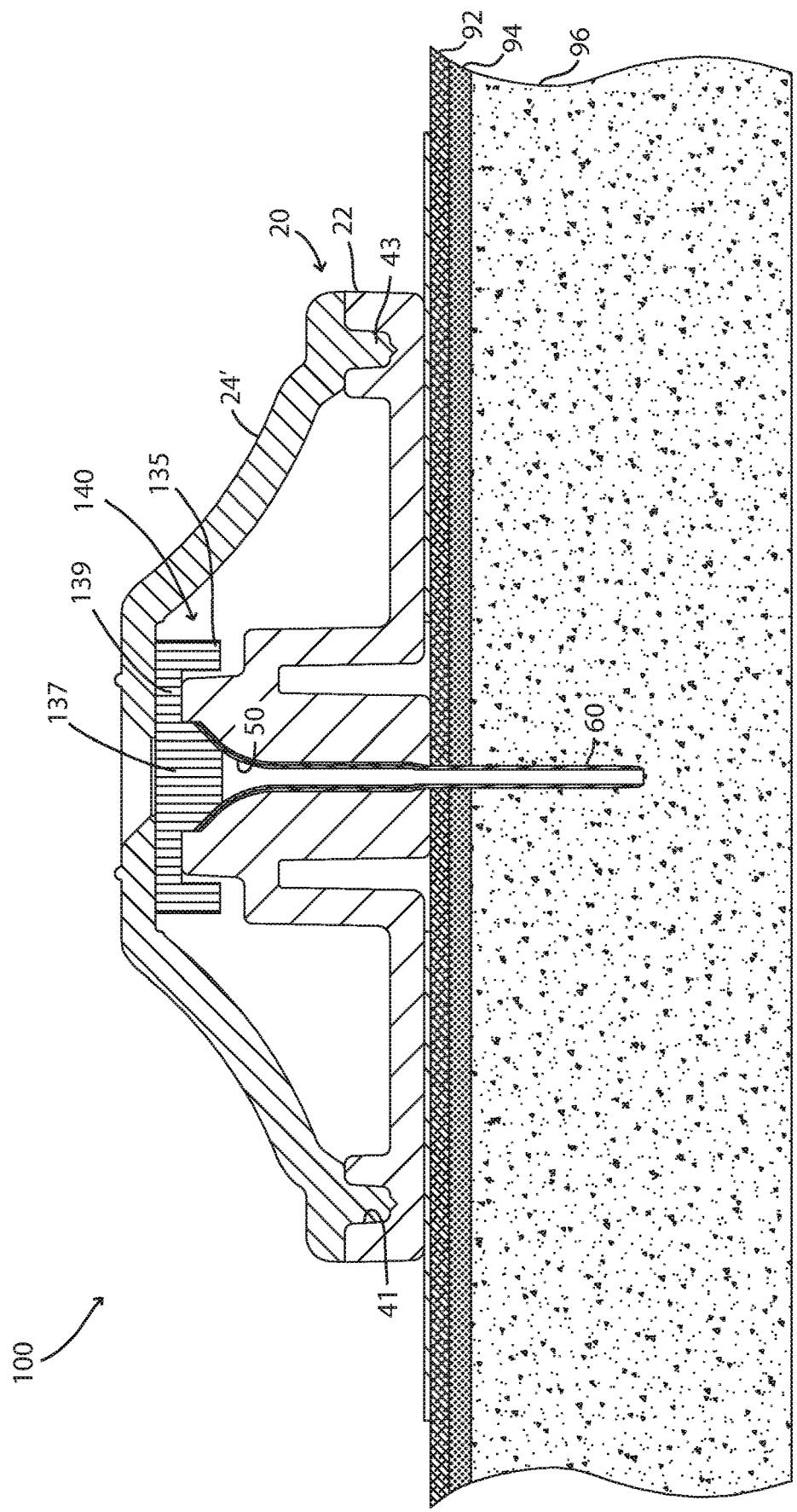
FIG. 5D is a cross-sectional view of another embodiment of the FIG. 1 fluid delivery device that includes a septum having a retention flange and a retention collar extending perpendicularly from the retention flange.

FIG. 5B is a detail view of a portion of fluid delivery device 100 around septum 40, and illustrates some of the features of the depicted embodiment of fluid delivery device 100. The depicted embodiment of septum 40 includes an accessible surface portion 42 (or, an "accessible portion") that is positioned downstream (or below, in this embodiment) of inlet port 21 and that is accessible to an injection structure such as an injection needle during normal use of the fluid delivery device ("normal use" does not include accessing the septum with an injection needle by somehow inserting the injection needle through the septum retaining shoulder of cap element 24). In this embodiment, accessible surface portion 42 is a portion of the top surface of the septum. The outer surface of septum 40 includes the top surface (of which accessible surface portion 42 is a part), a side wall 46 extending downstream from the top surface, a portion 48 that is tapered inwardly (or in a downstream direction), and a bottom surface 44 that, in this embodiment, is substantially parallel with the top surface. In this embodiment, the side wall is straight and parallel to an axis (not shown in this figure, but see axis 103 in FIG. 5E) that is centered within a portion (and, in the embodiment, all) of fluid delivery passageway 25. The majority of side wall 46 is in contact with (and may be radially compressed by) a surrounding portion or portions of the fluid delivery device. More specifically, the majority of side wall 46 is in contact with a surrounding portion of the body. In the depicted embodiment, portion 48 has an upstream section that is tapered at a constant angle and a downstream section with a concave taper that matches the corresponding convex taper of a portion of needle guide 50. The downstream section of portion 48 also may be characterized as having a taper of non-constant angle because, in the downstream direction, the material defining that section is curved (not flat). Similarly, the corresponding portion of needle guide 50 also may be characterized as tapering at a non-constant angle, the tapering being inwardly or in a downstream direction.

Accessible surface portion 42 has a perimeter, which is defined by cap element exit opening 28. The perimeter has a greatest width $W_{42}$, which comprises the greatest distance between any two points along the perimeter that are connected by a straight line. In this embodiment, the perimeter is circular in shape, and greatest width $W_{42}$ comprises the diameter of the circle. Other embodiments of the present fluid delivery devices may have cap element exit openings, and therefore accessible portions of the septa, that have different shapes. Bottom surface 44 of septum 40 has a perimeter that, in the depicted embodiment, is circular. The perimeter has a greatest width $W_{44}$, which comprises the greatest distance between any two points along the perimeter that are connected by a straight line. In this embodiment, greatest width $W_{44}$ comprises the diameter of the circle defined by bottom surface 44, although in other embodiments the bottom surface may be shaped differently. Bottom surface 44 may be more broadly characterized as a portion of the exterior surface of septum 40 (a "surface portion") that is adjacent to open space 15 that is downstream of the surface portion and within fluid delivery passageway 25.

As FIG. 5B shows, the perimeter of bottom surface 44 is smaller than the perimeter of accessible surface portion 42. This means that the linear distance represented by the perimeter of bottom surface 44 (which, for this embodiment, is a circumference) is smaller than the linear distance represented by the perimeter of accessible surface portion 42 (which also is a circumference, in this embodiment). Greatest width $W_{44}$ also is less that greatest width $W_{42}$. This relationship between the size of the perimeters of the two surface portions (accessible surface portion 42 and bottom surface 44) may be true of the septa used with other embodiments, such as any of the septa used with the multi-inlet embodiments described below.

Cannula 60 has a smallest internal width $W_c$ (see FIG. 5A), which is the width of the smallest portion of the material forming the cannula passageway. In this embodiment, greatest width $W_{42}$ is at least twice as great as the smallest internal width $W_c$ of cannula 60.

FIG. 5B also shows that septum 40 has a height $S_H$, which runs in a direction parallel to the axis described above, and a middle SM that is one-half of the height. The middle, in this embodiment, is in contact with a surrounding portion of fluid delivery device 100. The surrounding portion may be body material (as shown), or it may be needle guide material or cannula material in other embodiments. The middle also may be radially compressed by the material surrounding it.

Septum shapes other than the one shown, for example, in FIGS. 1-5B may be used for septum 40. For example, FIG. 5C shows another embodiment of fluid delivery device 100 that includes a septum 140, which has a lower portion that is similar in shape to the lower portion of septum 40, but that includes a septum retention flange 139 extending from the septum's central portion 137. Septum 140 has a shape in this embodiment that is symmetrical about the axis (not shown) that is centered within fluid delivery passageway 25. The surface area of septum 140 that is in contact with cap element 24' is greater than the surface area of the septum's exposed portion (see FIGS. 5E and 5F for a description of a septum's "exposed" portion). Septum retention flange 139 is oriented parallel to the engagement surface of the device and is perpendicular to the intended direction of insertion of the device. The flange is configured to help prevent upstream and downstream movement of septum 140 that might otherwise occur as a needle (e.g., an insertion or injection needle) is inserted through or withdrawn from the septum. FIG. 5D shows another septum embodiment—septum 140'—that includes a septum retention collar 135 protruding in a downstream direction from the septum retention flange 139. Collar 135 may help prevent lateral septum movement (or movement that includes a directional component that is perpendicular to the intended direction of insertion of the device) that might otherwise occur during needle insertion or withdrawal.

Furthermore, some or all of a given septum (e.g., the portion of septum 40 that includes accessible surface portion 42) may be artificially-colored (e.g., by adding a coloring agent to the material that forms the septum). This may enhance the contrast between the septum and the remainder of the fluid delivery device.

Figure 5E:
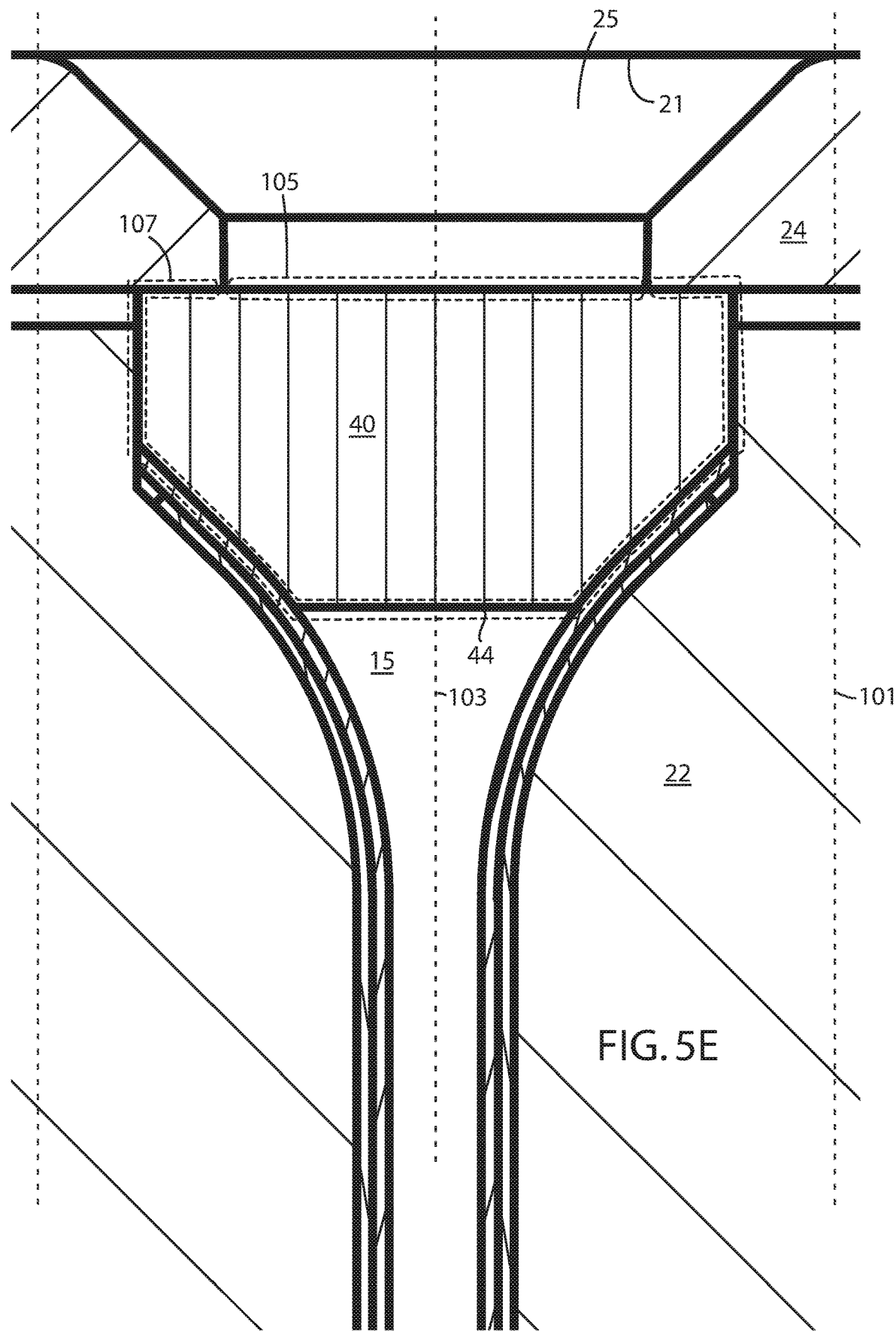
FIG. 5E is an enlarged detail view of a portion of the FIG. 5A view, showing aspects of one of the present fluid delivery devices.

FIG. 5E, which depicts the same detail shown in FIG. 5B, highlights certain aspects of the embodiment of fluid delivery device 100 shown in FIG. 1. FIG. 5E shows that the body has a boundary 101 (also described as a "first inlet boundary" and an "inlet boundary") extending upstream and downstream of inlet port 21 (or inlet 21) parallel to an axis 103 centered within a portion (and, in the depicted embodiment, all) of fluid delivery passageway 25. FIG. 5E also shows that the outer surface of septum 40 includes an exposed portion located within boundary 101 and a remaining non-exposed portion. The exposed portion is encircled by the dashed line labeled 105. The remaining non-exposed portion, which comprises all of the outer surface of septum 40 other than exposed portion 105, is encircled by the dashed line labeled 107. Although an injection needle is not shown in this figure, one can see that an injection needle that enters exposed portion 105 in a downstream direction and exits septum 40 through part of remaining non-exposed portion 107 that is substantially perpendicular to axis 103 (the part can be any part of bottom surface 44 in this embodiment) will exit septum 40 into a portion of open space 15 that will be within fluid delivery passageway 25 and downstream of the part through which the injection needle exited. Thus, the embodiment of the present fluid delivery devices shown in FIGS. 1-5B and 5E is an example of one that is configured such that an injection needle that enters the exposed portion of the septum (which is within the boundary) in a downstream direction and exits the septum (a) through part of the remaining non-exposed portion that is substantially perpendicular to an axis that is centered within a portion of the fluid delivery passageway or (b) through part of the remaining non-exposed portion that has a tangent that is not parallel to the axis, exits the first sealing mechanism into open space that is (c) within the first fluid delivery passageway and (d) downstream of the part through which the injection needle exited.

Figure 5F:
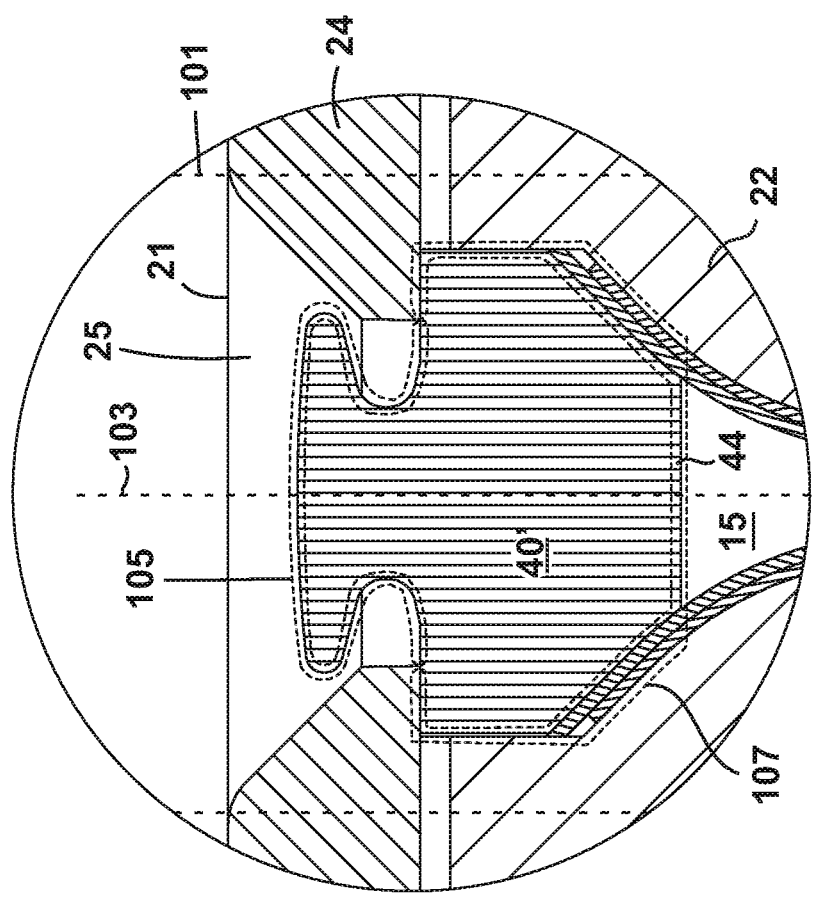
FIG. 5F is an enlarged detail view showing aspects of another embodiment of the present fluid delivery devices, and more specifically another of the present septa.

FIG. 5F depicts another embodiment of the present fluid delivery devices that has this configuration. FIG. 5F shows another configuration of exposed portion 105 of one of the present septa: septum 40'.

Figure 5G:
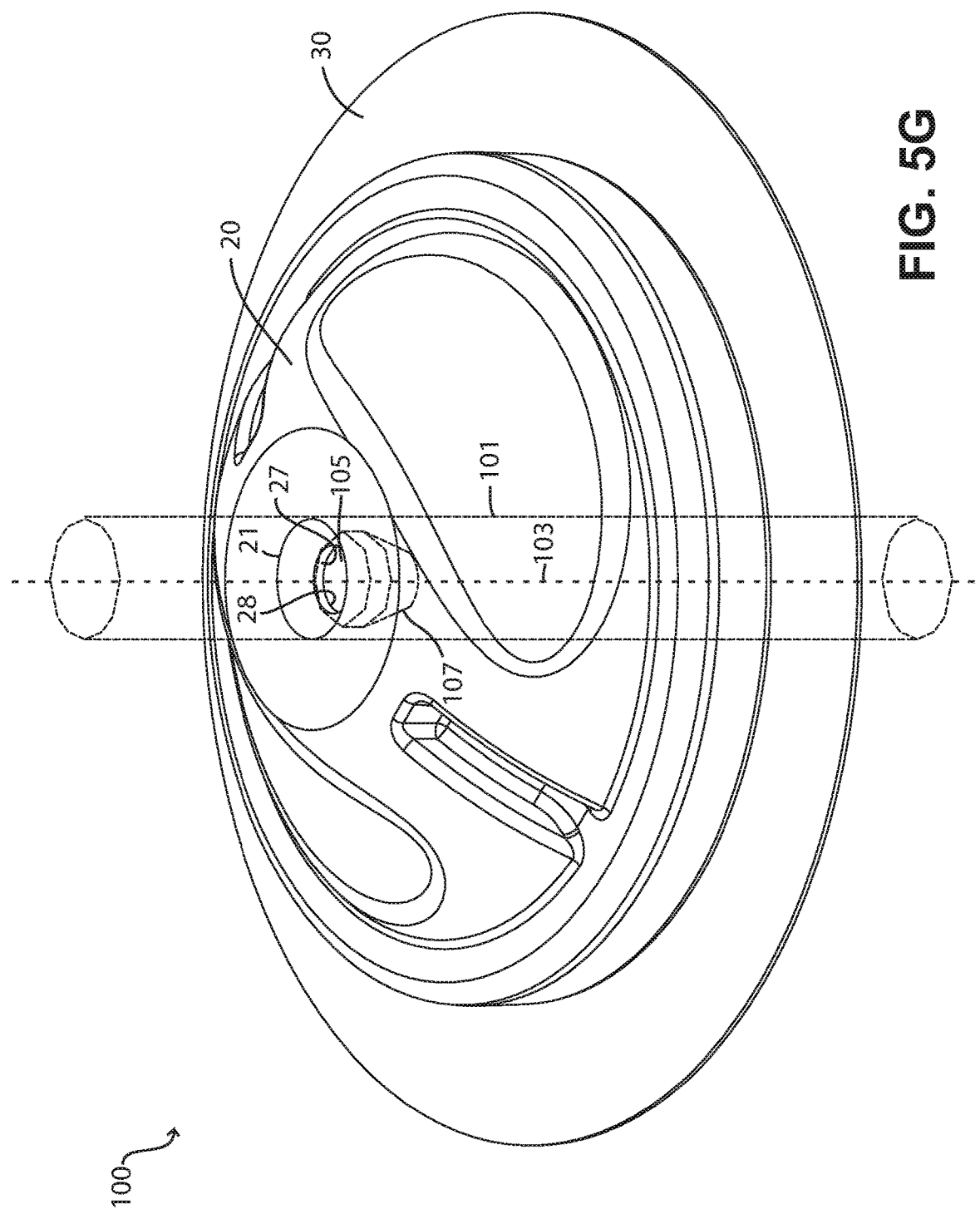
FIG. 5G shows the boundary illustrated in FIG. 5E in perspective.

FIG. 5G shows how boundary 101 looks in perspective.

Figure 5H:
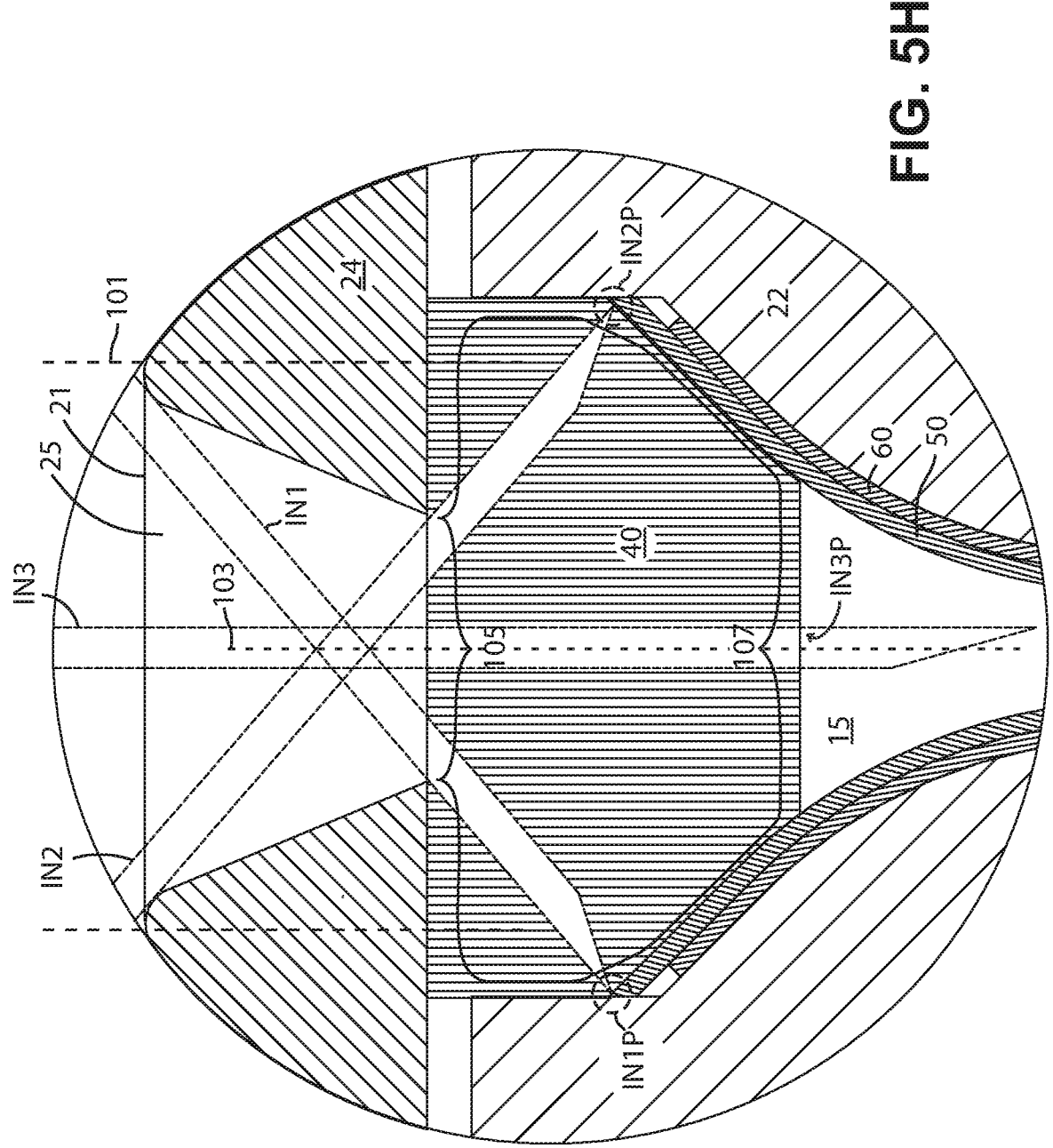
Figure 5J:
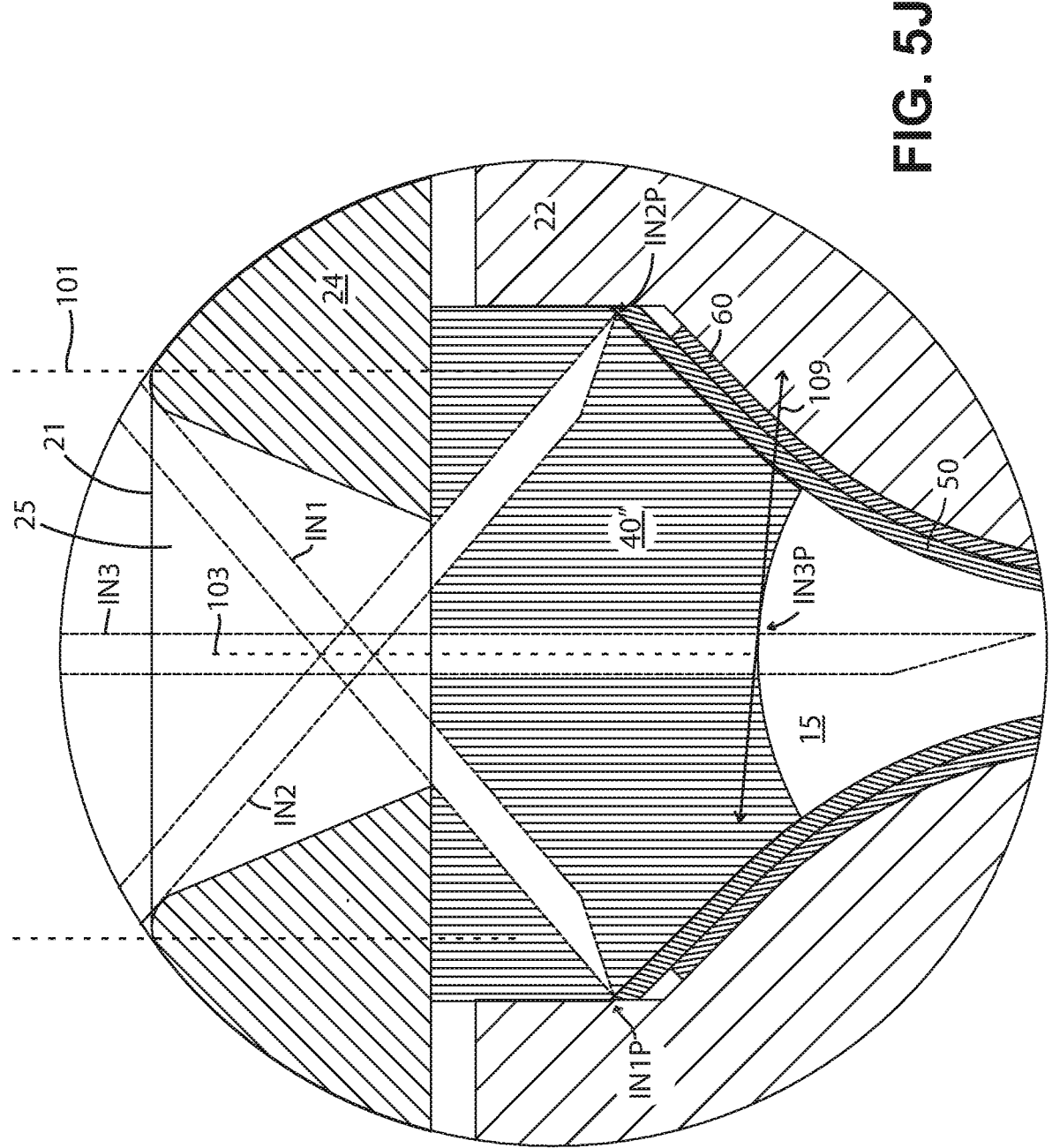

Each of FIGS. 5H-5J depicts an embodiment of the present fluid delivery devices that is configured such that an injection needle that enters the exposed portion of the septum (which is within the boundary) in a downstream direction and exits the septum (a) through part of the remaining non-exposed portion that is substantially perpendicular to an axis that is centered within a portion of the fluid delivery passageway or (b) through part of the remaining non-exposed portion that has a tangent that is not parallel to the axis, exits the septum into open space that is (c) within the fluid delivery passageway and (d) downstream of the part through which the injection needle exited. Each of FIGS. 5H-5J also depicts an embodiment of the present fluid delivery devices that is configured such that an injection needle that enters the exposed portion of the septum (which is within the boundary) in a downstream direction and exits the septum through part of the remaining non-exposed portion that is not parallel to the axis either (a) exits the septum into open space that is (i) within the fluid delivery passageway and (ii) downstream of the part, or (b) contacts a portion of the fluid delivery device that is tapered inwardly.

In FIG. 5I, for example, injection needles IN1 and IN2, shown in phantom, have each entered exposed portion 105 of septum 40 in a downstream direction and have exited the septum through part (IN1P and IN2P, respectively) of remaining non-exposed portion 107 that is not parallel to axis 103 and contacted a portion of the fluid delivery device (in this embodiment, a portion of needle guide 5B0) that is tapered inwardly. Injection needle IN3, shown in phantom, has entered exposed portion 105 of septum 40 in a downstream direction and has exited the septum through part (IN3P) of remaining non-exposed portion 107 that is not parallel to axis 103, the exiting being into open space (a central portion of open space 15) that is within fluid delivery passageway 25 and downstream of part IN3P. Furthermore, as FIG. 5I shows, injection needle IN3 has entered exposed portion 105 of septum 40 in a downstream direction and exited septum 40 through part (IN3P) of remaining non-exposed portion 107 that is substantially perpendicular to axis 103, the exiting being into open space that is within fluid delivery passageway 25 and downstream of part IN3P.

In FIG. 5I, injection needles IN1 and IN2 have each entered the exposed portion (not labeled) of septum 40″ in a downstream direction and have exited the septum through part (IN1P and IN2P, respectively) of the remaining non-exposed portion (not labeled) that is not parallel to axis 103 and contacted a portion of the fluid delivery device that is tapered inwardly. Injection needle IN3, shown in phantom, has entered the exposed portion of septum 40″ in a downstream direction and has exited the septum through part (IN3P) of the remaining non-exposed portion that is not parallel to axis 103, the exiting being into open space (a central portion of open space 15) that is within fluid delivery passageway 25 and downstream of part IN3P. Furthermore, as FIG. 5I shows, injection needle IN3 has entered the exposed portion of septum 40″ in a downstream direction and exited septum 40″ through part (IN3P) of the remaining non-exposed portion that has a tangent 109 that is not parallel to axis 103, the exiting being into open space that is within fluid delivery passageway 25 and downstream of part IN3P.

In FIG. 5J, injection needles IN1 and IN2 have each entered exposed portion 105 of septum 40‴ in a downstream direction and have exited the septum through part (IN1P and IN2P, respectively) of remaining non-exposed portion 107 that is not parallel to axis 103 and contacted a portion of the fluid delivery device (in this embodiment, portion 33) that is tapered inwardly. Injection needle IN3, shown in phantom, has entered exposed portion 105 of septum 40‴ in a downstream direction and has exited the septum through part (IN3P) of remaining non-exposed portion 107 that is not parallel to axis 103, the exiting being into open space (a central portion of open space 15) that is within fluid delivery passageway 25 and downstream of part IN3P. Furthermore, as FIG. 5J shows, injection needle IN3 has entered exposed portion 105 of septum 40‴ in a downstream direction and exited septum 40‴ through part (IN3P) of remaining non-exposed portion 107 that has a tangent 109 that is not parallel to axis 103, the exiting being into open space that is within fluid delivery passageway 25 and downstream of part IN3P.

The septa shown in each of FIGS. 3-5B and 5E-5J include a portion that is positioned within fluid delivery passageway 25. In the depicted embodiments, the portion comprises all of the respective septa. Each of the septa depicted in these figures also includes a portion positioned within needle guide 50 (or, more specifically, the needle guide passageway (unnumbered) of needle guide 50). In the depicted embodiments, this portion comprises a lower portion of the depicted septum, specifically portion 48 (see FIG. 5B). Some of portion 48 is also positioned within cannula 60, or, more specifically, the cannula passageway (unnumbered) of cannula 60.

Figure 6:
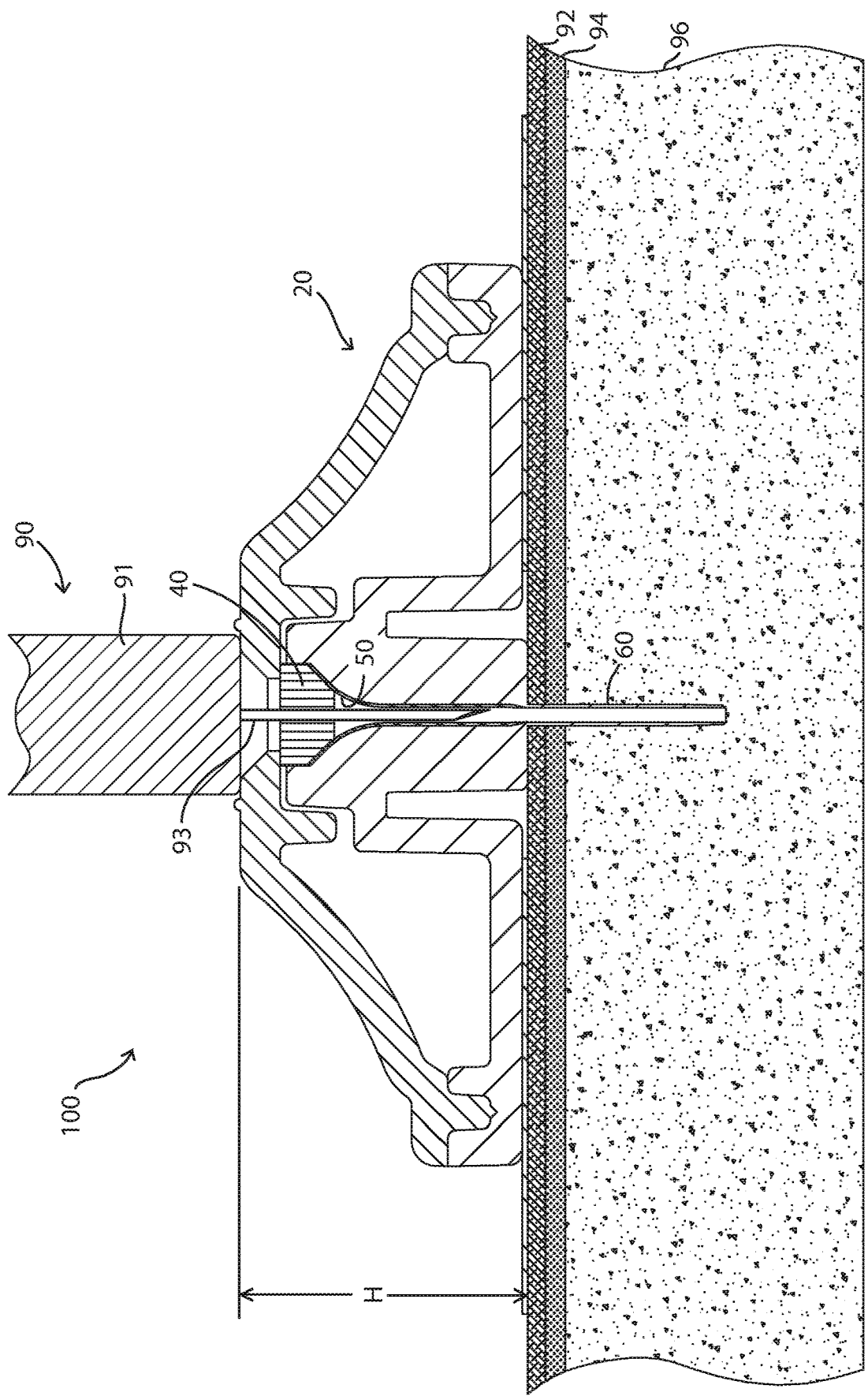
FIG. 6 is a cross-sectional view of the fluid delivery device shown in FIG. 1, taken along the same plane as FIG. 5A, showing an injection needle inserted into the device.

FIG. 6 depicts an injection device 90 fully inserted into fluid delivery device 100. The injection device may be used to inject fluid (e.g., insulin) into the subcutaneous tissue of a user. The depicted embodiment of injection device 90 comprises a standard syringe that includes a generically-depicted plunger portion 91 and an injection structure 93 that comprises, in this embodiment, a standard syringe needle. Other injection devices may be used with embodiments of the present fluid delivery devices to deliver fluid to a user. Fluid delivery device 100 includes a needle control portion that is configured to prevent a needle (e.g., injection needle 93) sized to inject fluid through the fluid delivery device and into a living being from piercing cannula 60 during normal fluid injection. In this embodiment, normal fluid injection involving an injection needle involves inserting the injection needle through the accessible surface portion 42 of septum 40. In this embodiment, the needle control portion comprises needle guide 50, which protects the inner wall of cannula 60 (which defines the cannula passageway) from being contacted by the injection needle, and which includes a shaft portion having a sufficiently small inner diameter such that any injection needle sized to deliver fluid to a living being through the device will not be able to tilt enough to pierce any portion of the cannula that is accessible to the injection needle downstream of the end of the needle guide. In this embodiment, injection needle 93 terminates above the lowermost end of needle guide 50. Needle control portions other than a needle guide may be used in other embodiments. For example, although not shown in the figures, a portion of the opening in cap element 24, such as straight-walled portion 27, could be configured to define a portion of the fluid delivery passageway that is sufficiently small enough to perform the function of the shaft portion of needle guide 50.

Generally, FIG. 6 shows that the depicted embodiment of fluid delivery device 100 is an example of a fluid delivery device that is configured such that a needle sized to inject fluid through the fluid delivery device (which may involve the fluid only being in contact with a lower portion of the device, such as the lower portion of cannula 60) and into a living being cannot pierce the cannula during normal fluid injection. Furthermore, as FIG. 6 shows, the depicted embodiment of fluid delivery device 100 is one that is configured such that, when properly installed to a living being, a needle inserted through the septum to deliver fluid to the living being (e.g., injection needle 93) will not puncture the living being's skin. These configurations are achieved in this embodiment through choosing the height H of fluid delivery device 100 to be greater than the length of injection needle 93 and by configuring needle guide 50 to overlap all portions of cannula 60 that would otherwise be exposed to an injection needle inserted properly through septum 60.

Figure 7B:
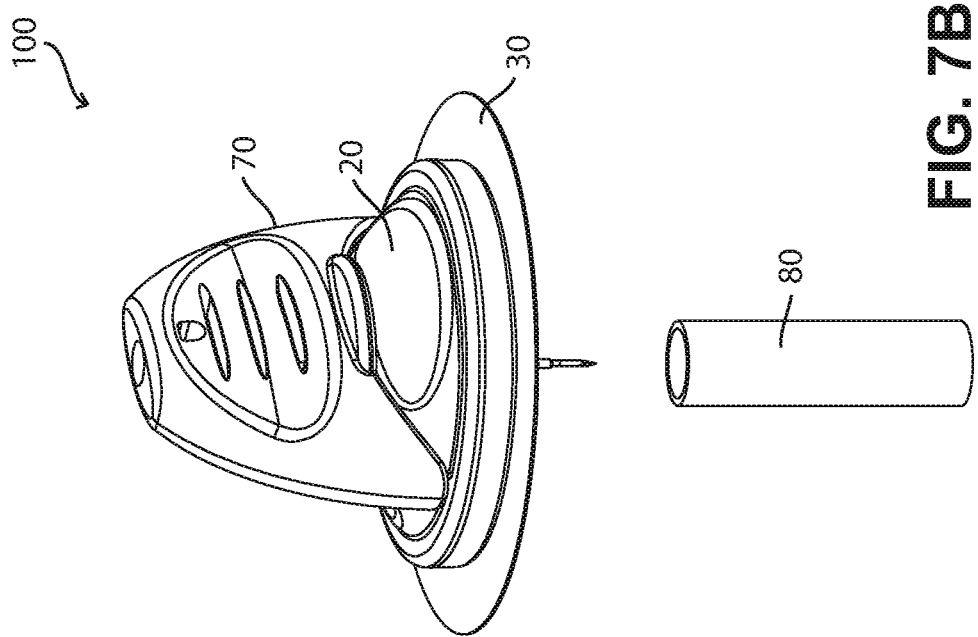
FIGS. 7A and 7B are perspective views of the FIG. 1 fluid delivery device, showing the result of trying to decouple the insertion device and needle guard from the body using equal and opposite forces: the needle guard uncouples first.
Figure 7A:
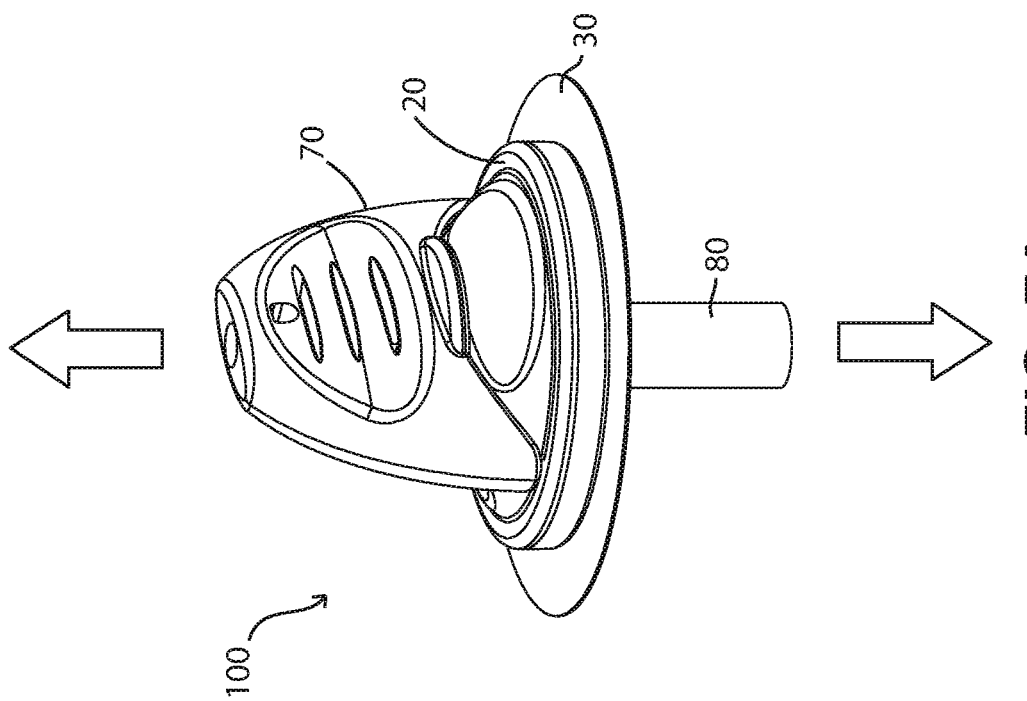

FIGS. 7A and 7B illustrate that the depicted embodiment of fluid delivery device 100 is configured such that pulling insertion device 70 and needle guard 80 in opposite directions (as indicated by the two arrows in FIG. 7A) with equal force to uncouple them from body 20 causes needle guard 80 to uncouple from body 20 first. This configuration may be achieved in different ways. For example, in the depicted embodiment, the friction force between insertion device 70, which is fully inserted in body 20, and septum 40 is greater than the friction force between body 20 and needle guard 80. Septum 40 may be a non-split septum, which adds to the friction force between it and insertion needle 72 of insertion device 70. In other embodiments, septum 40 may be split, or otherwise configured to produce less friction force against the withdrawal of an insertion needle, and insertion device hub 74 and body 20 (more specifically, cap element 24) may be configured to engage one another (e.g., through a friction fit or interlocking parts) in a way that (a) makes it necessary to use more force to uncouple insertion device 70 from body 20 than it takes to uncouple needle guard 80 from body 20, or (b) makes it not possible to uncouple insertion device 70 from body 20 by pulling on insertion device 70 and needle guard 80 in equal and opposite directions without first manipulating insertion device 70 relative to body 20 (e.g., by twisting insertion device 70 to unlock it from body 20).

Figure 8:
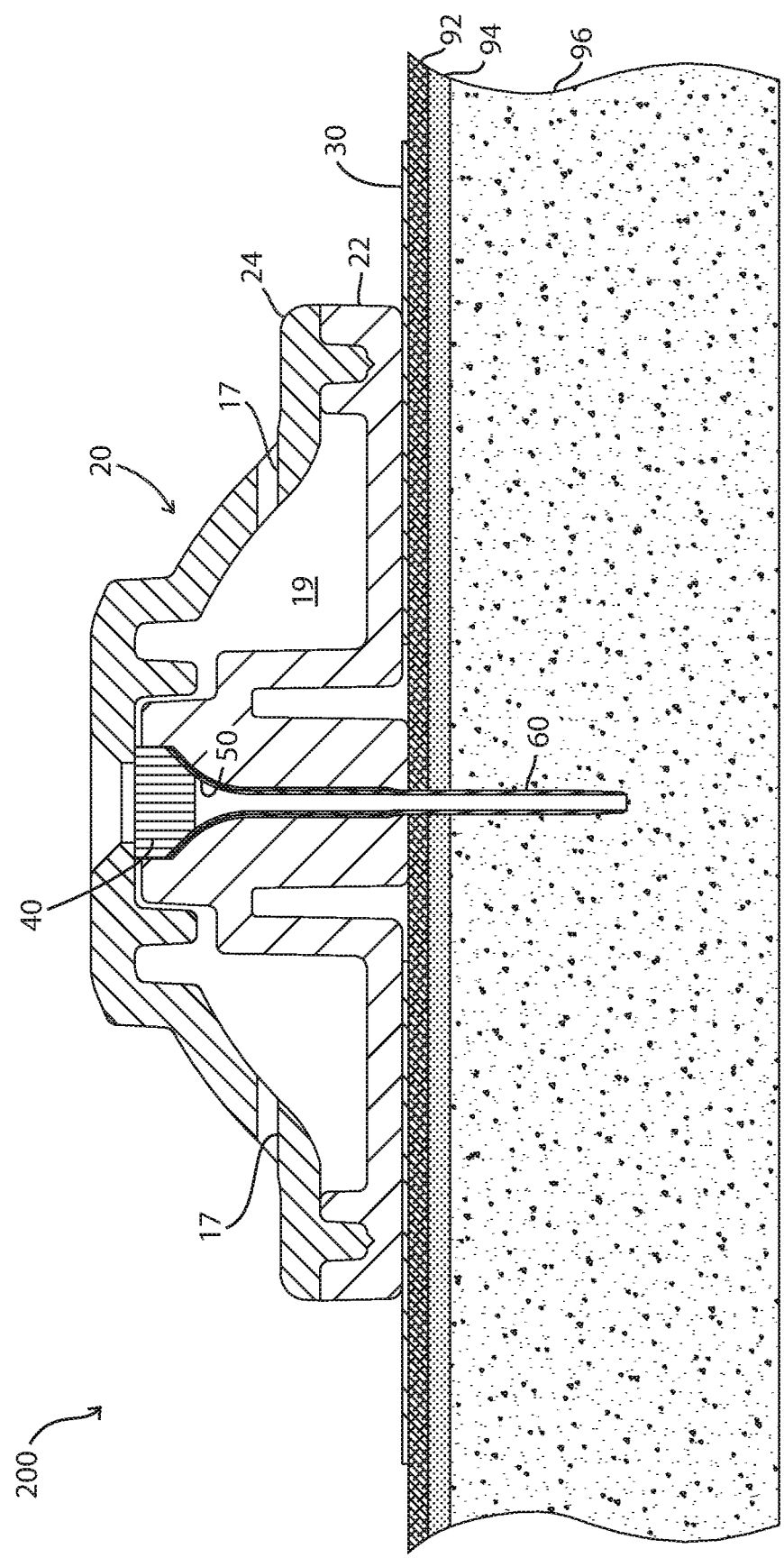
FIG. 8 is a cross-sectional view of an embodiment of the present fluid delivery devices that includes a body cavity that is in fluid communication with the exterior of the device through at least one opening in a sidewall of the device.

FIG. 8 shows another embodiment of the present fluid delivery devices. Fluid delivery device 200 is similar to fluid delivery device 100. However, body cavity 19 of body 20 of fluid delivery device 200 is open to the exterior of body 20 by virtue of a body cavity opening. More specifically, body 20 includes at least two body cavity openings 17 that are positioned in cap element 24 and that are in fluid communication with body cavity 19. Body cavity 19 in both fluid delivery device 200 and fluid delivery device 100 will not contact fluid that is being delivered through the fluid delivery passageway of body 20 to a living being (meaning that the body cavity will not contact the fluid as it is delivered through the body to a living being). However, if the otherwise sealed condition of body 20 is breached (e.g., around septum 40 or location 29), and fluid gets into body cavity 19, that fluid can drain out of body cavity 19 through one or more of body cavity openings 17.

When the fluid delivery device is made from two or more pieces or elements, there are many suitable configurations for those elements. FIGS. 1-8, for example, show some examples of suitable configurations for cap element 24 and base element 22 of body 20. Another suitable configuration of these elements is shown in FIG. 9.

Figure 9:
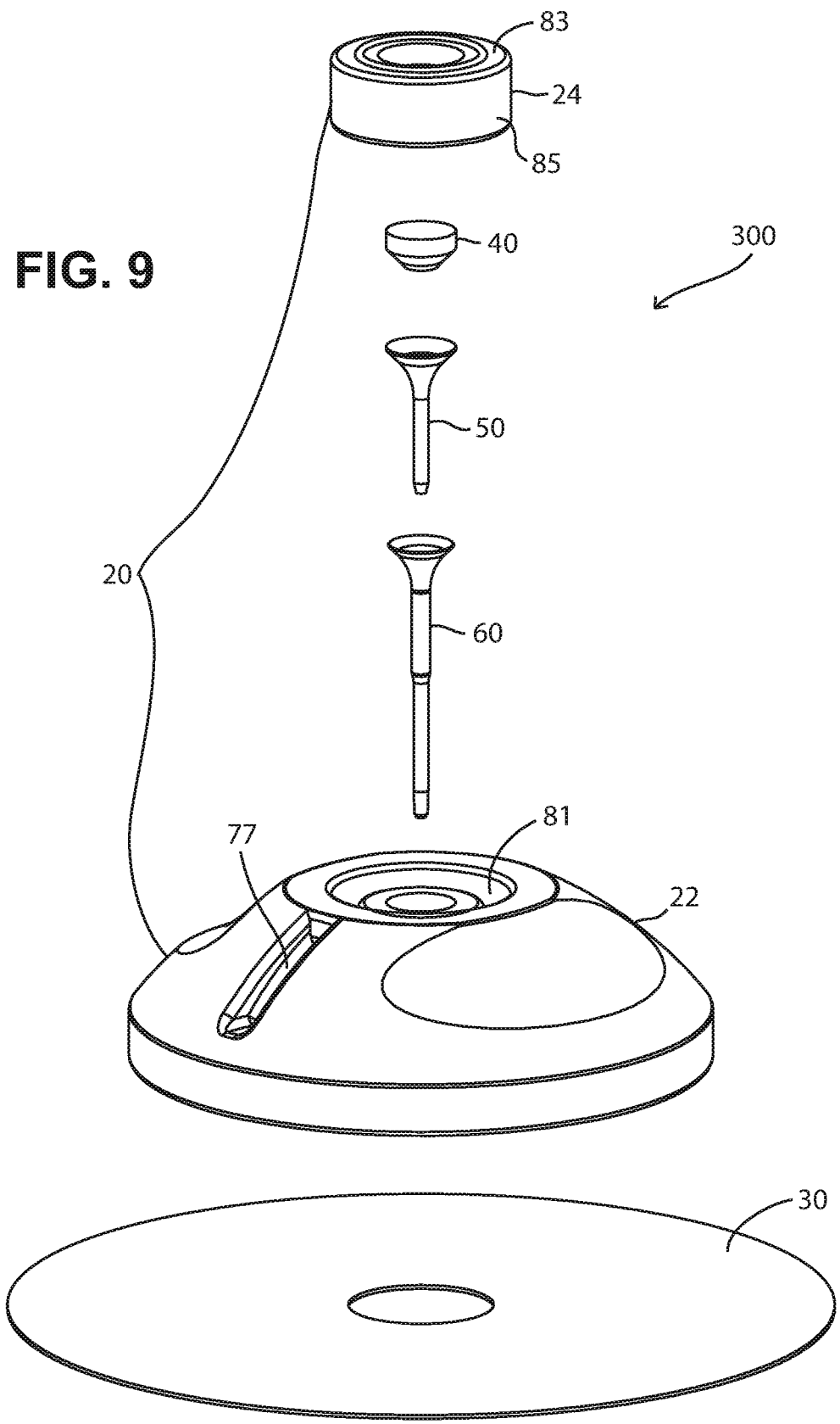
FIG. 9 is a perspective exploded view of another embodiment of the present fluid delivery devices.

FIG. 9 is an exploded perspective view of fluid delivery device 300, which includes a body 20 having cap element 24 (which may also be described as a septum cap) and base element 22 (which may also be described as a base), septum 40, needle guide 50, cannula 60 and adhesive layer 30. An insertion device and a needle guard may be coupled to body 20 of fluid delivery device 300 in similar fashion to how they are coupled to fluid delivery device 100. Base 22 of this embodiment includes rotation-restricting recesses 77. Base 22 also includes cap recess 81 that comprises, in this embodiment, an annular groove that is parallel with fluid delivery passageway 25. Cap 24 includes a top portion 83 and a base-engaging section 85 extending downstream from top portion 83. At least a portion of base-engaging section 85 is complimentary in shape to a portion of cap recess 81. Cap 24 may be coupled to base 22 in any suitable manner. In one embodiment, cap 24 may be permanently attached to base 22 using ultrasonic welding or any other suitable permanent attachment technique, such as those described above.

Figure 10:
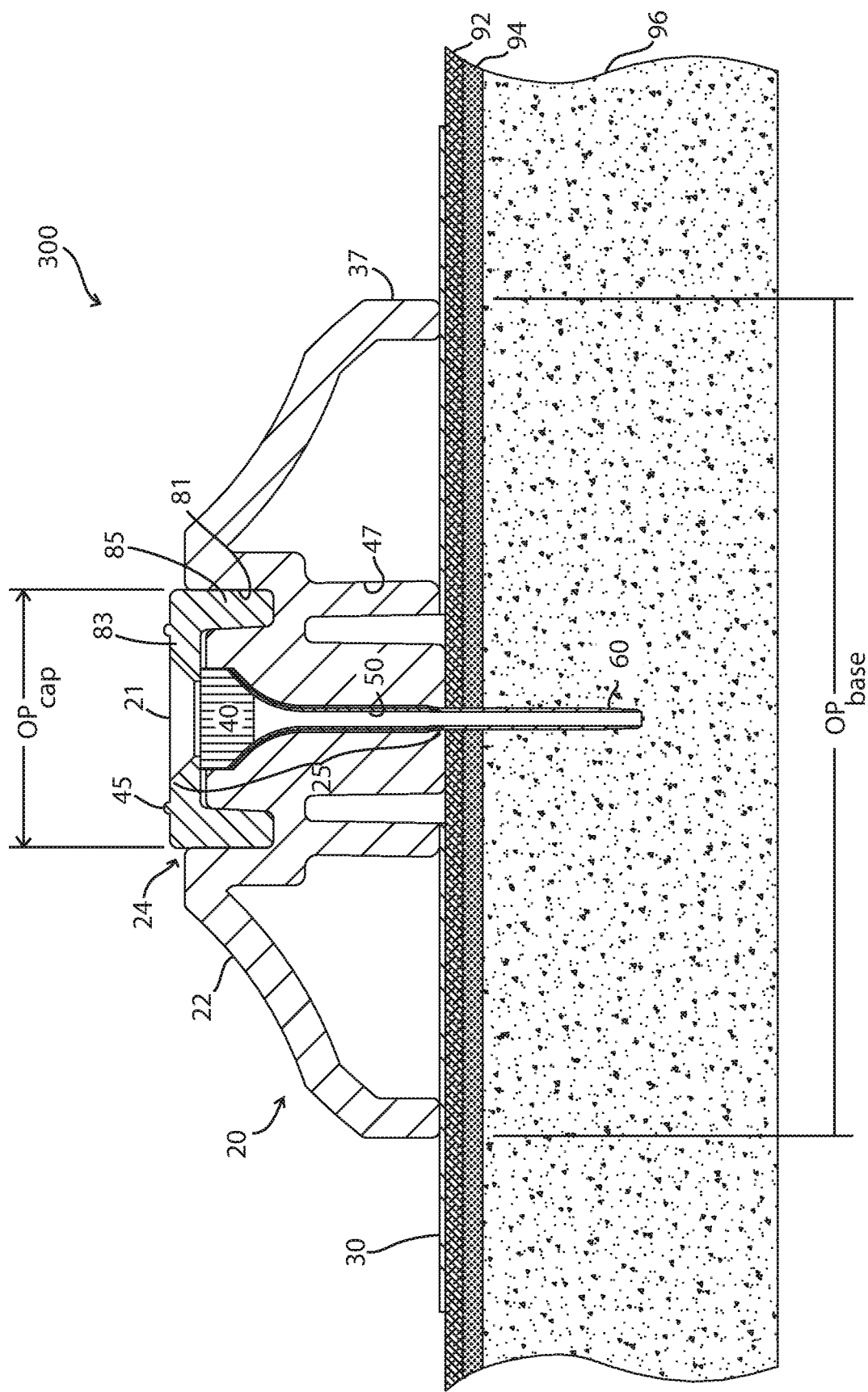
FIG. 10 is a cross-sectional view of the fluid delivery device shown in FIG. 9, taken along a plane that does not intersect either rotation-restricting recess of the base element of the body, showing the device installed to a user and the insertion device removed.

FIG. 10 is a cross-sectional view of fluid delivery device 300 inserted in a living being, and shows that fluid delivery passageway 25 of this embodiment may comprise the same openings and portions as the embodiment of fluid delivery device 100 shown, for example, in FIGS. 3 and 4. FIG. 10 also shows that cap 24 has an outer perimeter $OP_{cap}$, base 22 has an outer perimeter $OP_{base}$, and $OP_{base}$ is greater than $OP_{cap}$. In this embodiment, the outer perimeter of base 22 is also the same as the outer perimeter 37 of body 20.

Figure 11:
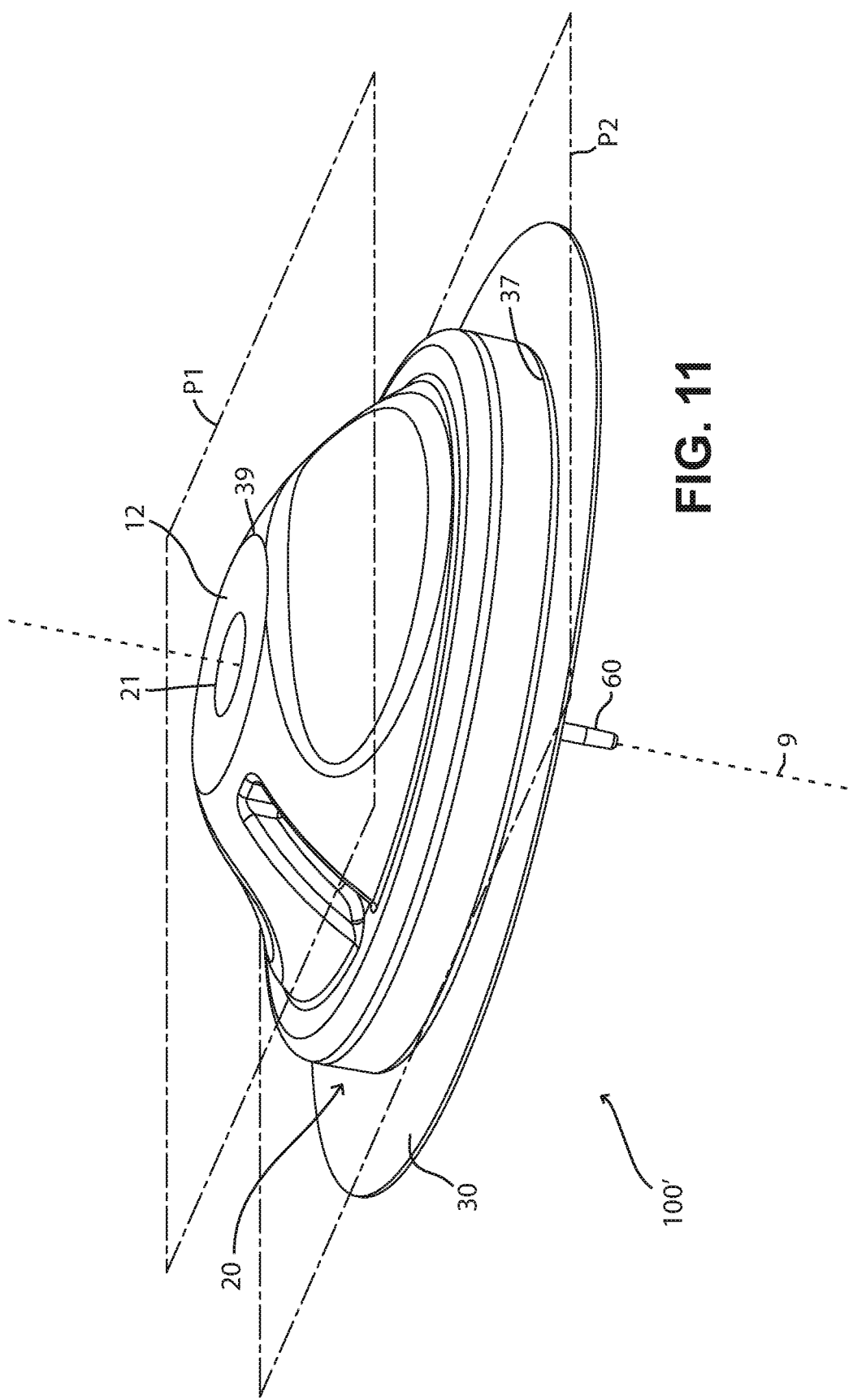
FIG. 11 is a perspective view showing the position of different perimeters of one of the present fluid delivery devices, the different perimeters being positioned in different planes that intersect the device.

FIG. 11 shows fluid delivery device 100', which is similar to fluid delivery device 100 except for lacking identification feature 45. This figure illustrates that body 20 has a first perimeter 39 at top 12 and a second perimeter (which, in this embodiment, comprises outer perimeter 37) that is close to the bottom surface of the body (which is the bottom surface of the base element). First perimeter 39 is positioned in a first plane P1, which is perpendicular to axis 9 that is centered within the fluid delivery passageway of the body (and that is, therefore, parallel to a portion of the fluid delivery passageway). Second perimeter 37 is positioned in a second plane P2, which is parallel to and downstream of first plane P1. As FIG. 11 shows, second perimeter 37 is greater than first perimeter 39. This means that the linear distance represented by second perimeter 37 is larger than the linear distance represented by first perimeter 39.

Figure 12:
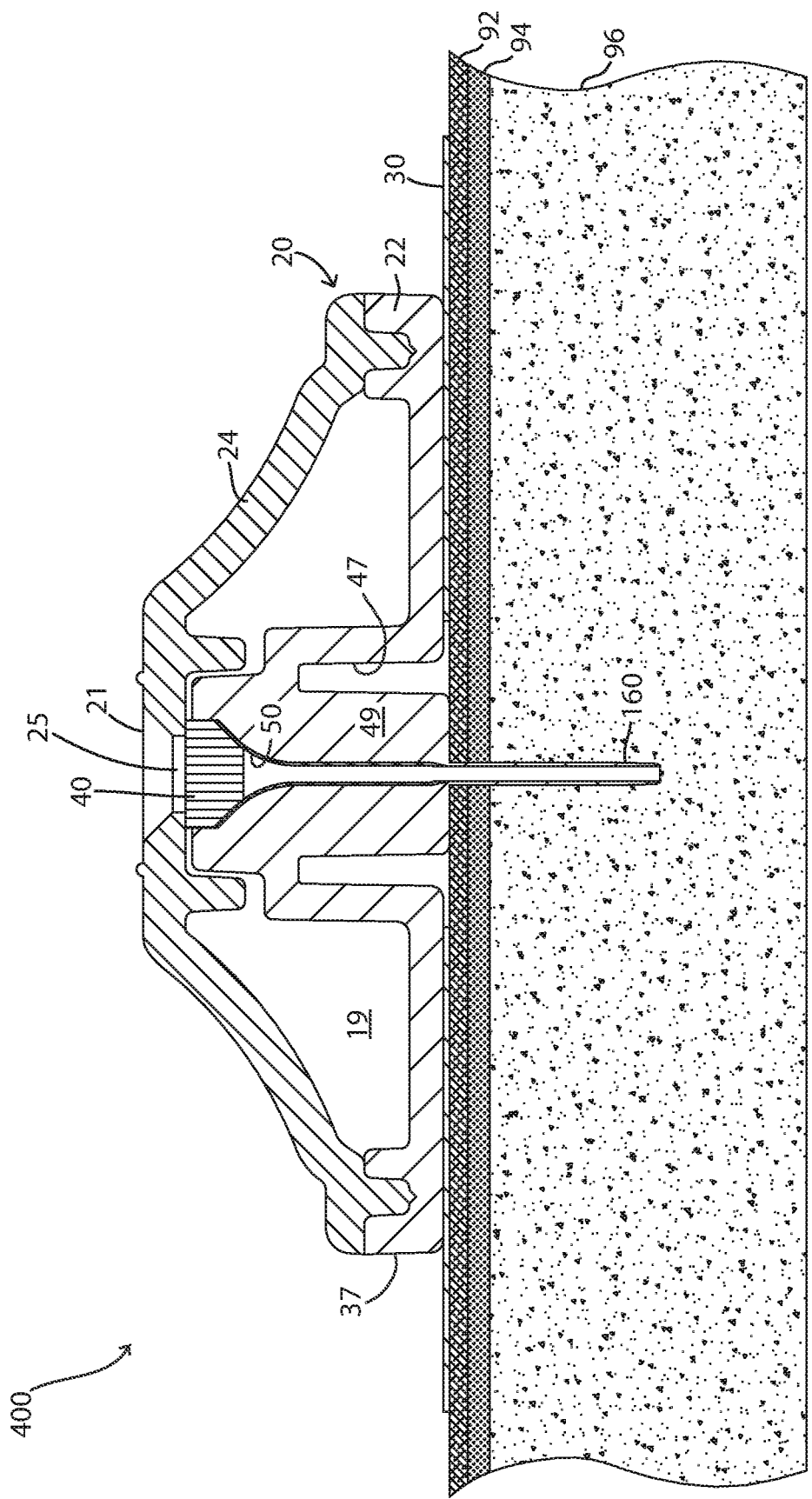
FIG. 12 is a cross-sectional view of a fluid delivery device having a cannula integral with the body.
Figure 13A:
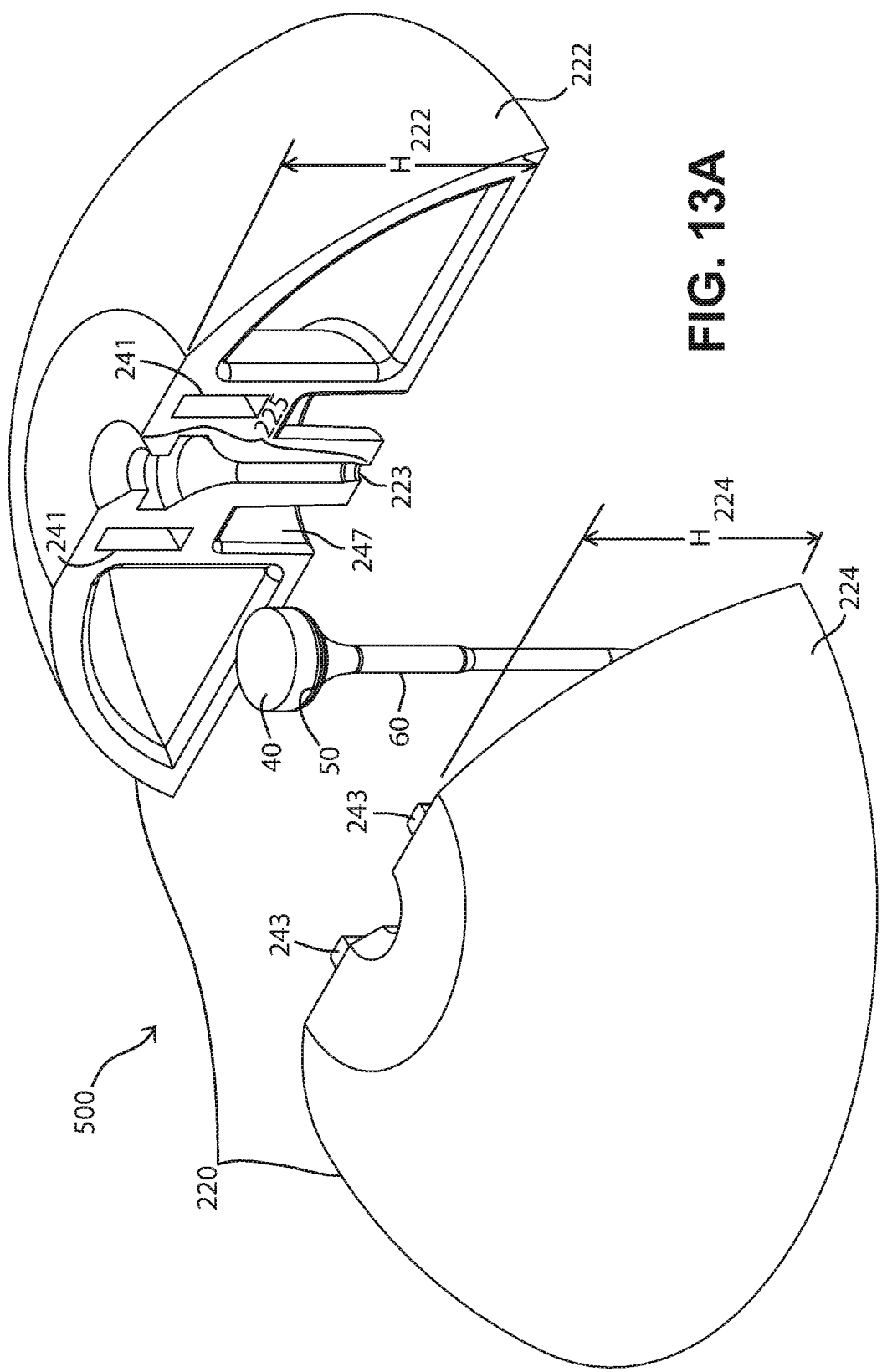
FIGS. 13A and 13B are exploded views of an embodiment of a fluid delivery device that is assembled from at least two body pieces, or elements, of substantially equal height. The views are taken from different perspectives.
Figure 13B:
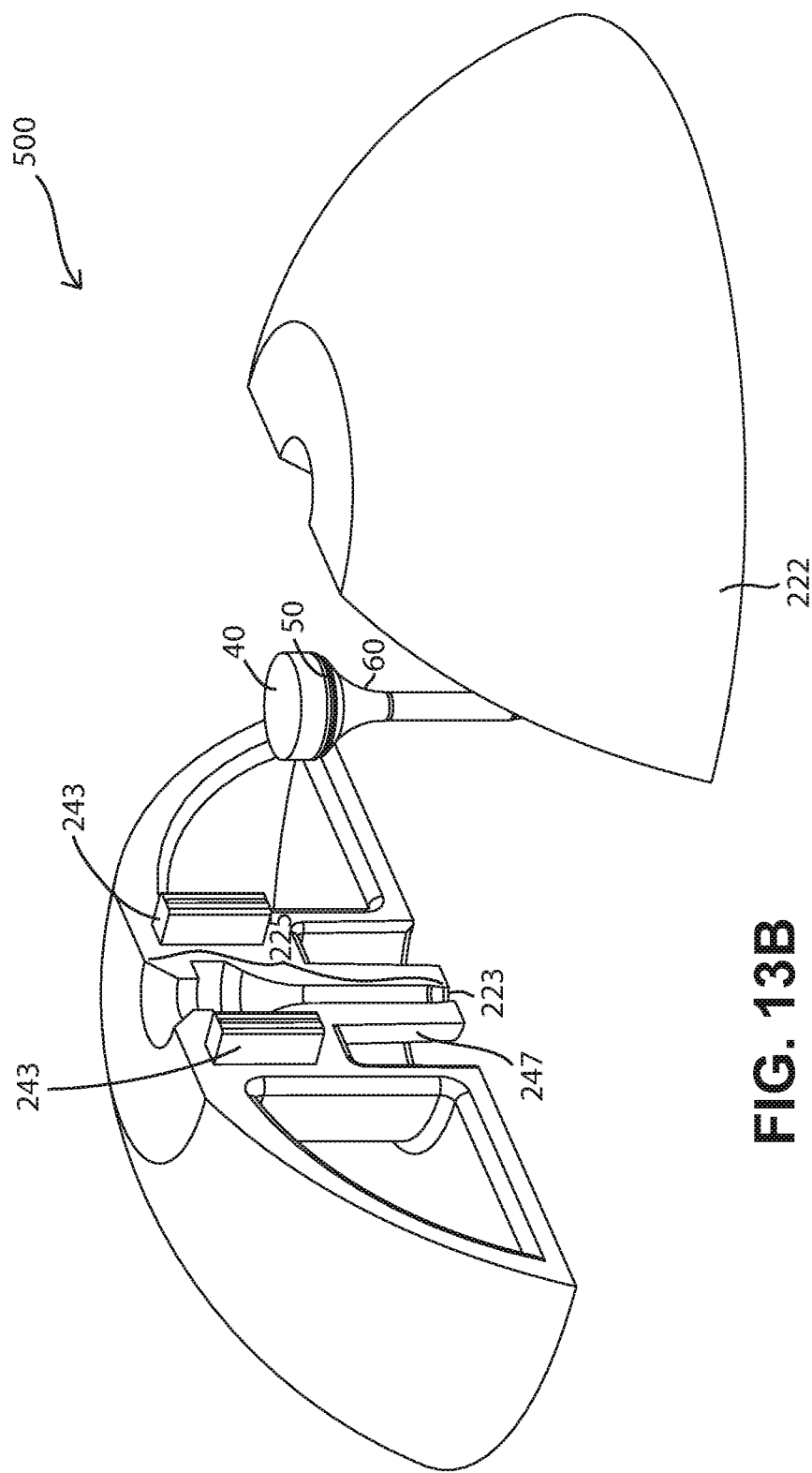

The cannulas shown in the figures described above are separate from the body of the depicted fluid delivery devices. In some other embodiments, the cannula may be integrally formed with the body. An example of such an embodiment is fluid delivery device 400, shown in FIG. 12. Fluid delivery device 400 includes cannula 160 that is integral with (or integrally formed with), and extends from, body 20. In this embodiment, needle guide 50 is in direct contact with a portion of the body material forming fluid delivery passageway 25.

Multi-piece or multi-element bodies other than those shown in FIGS. 1-12 are possible. For example, FIGS. 13A-17 show aspects of an embodiment that assembles in a plane that is substantially parallel to an axis of at least a portion of the fluid delivery passageway. In the depicted embodiment, the assembly plane is parallel to the axis of the fluid delivery passageway. These figures also show an example of a body that comprises multiple body elements of substantially equal height assembled in at least one device plane that is substantially parallel to an axis of a portion of the fluid delivery passageway. The phrase "an axis of a portion of [a/the] fluid delivery passageway" means an axis that is centered within and running parallel to the portion in question. Such an axis does not intersect the fluid delivery passageway wall portion that defines the portion in question.

Fluid delivery device 500 is similar in some respects to the previously-depicted embodiments. It includes a body 220, a septum 40, a needle guide 50 and a cannula 60. Body 220, however, comprises two elements 222 and 224 that assembly in a device plane that, in this embodiment, is parallel to fluid delivery passageway 225. Body 220 also includes needle guard holding recess 247 that is configured to accept a top portion of a needle guard such that the needle guard may be held to body through a friction fit, or any other suitable means of engagement. Elements 222 and 224 have substantially the same height. More specifically, height 11222 and 11224 (see FIG. 13A, not labeled in FIG. 13B) are equal in this embodiment.

Figure 14:
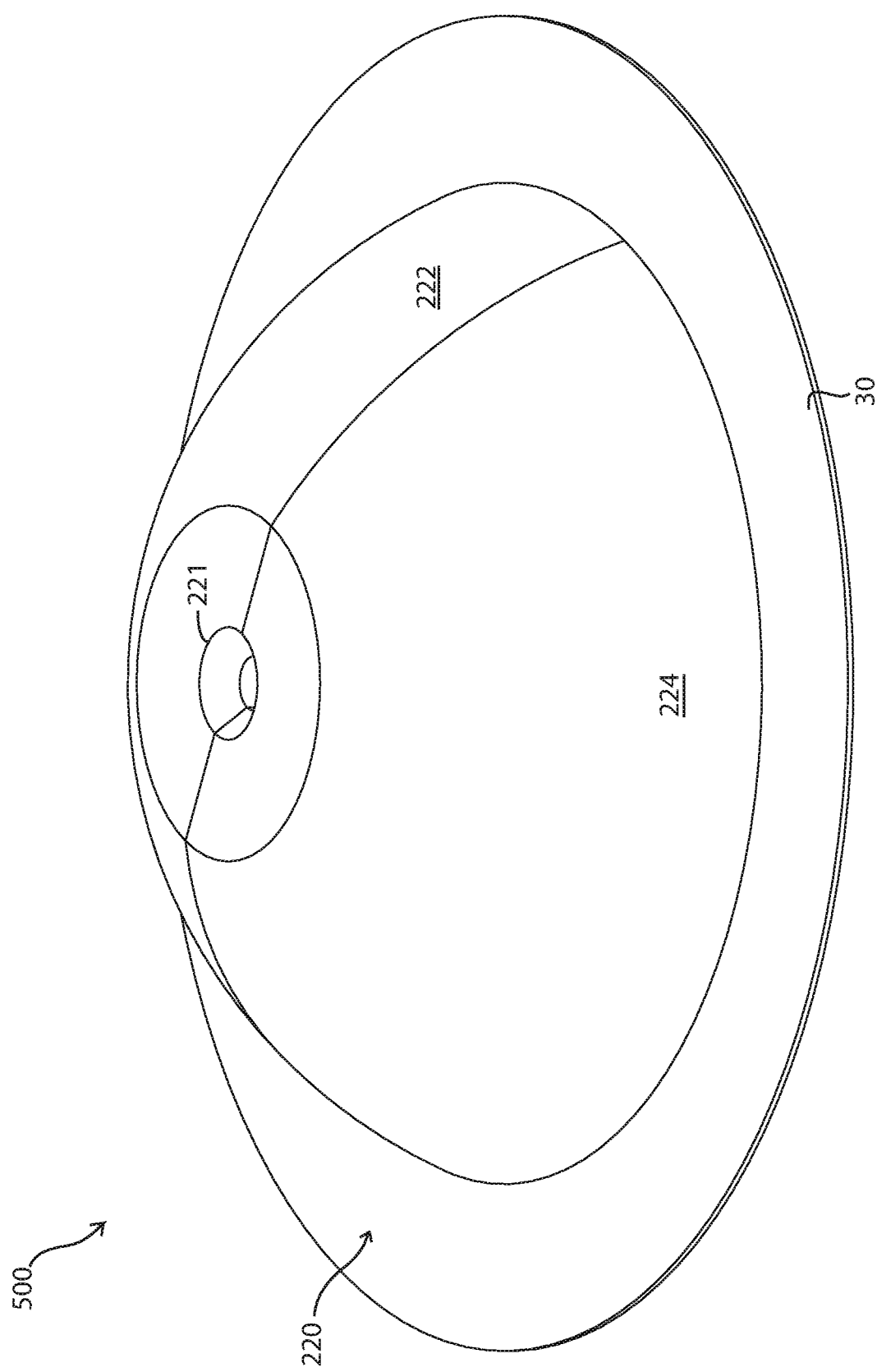
FIG. 14 is a perspective view of the assembled version of the fluid delivery device shown in FIGS. 13A and 13B.
Figure 15:
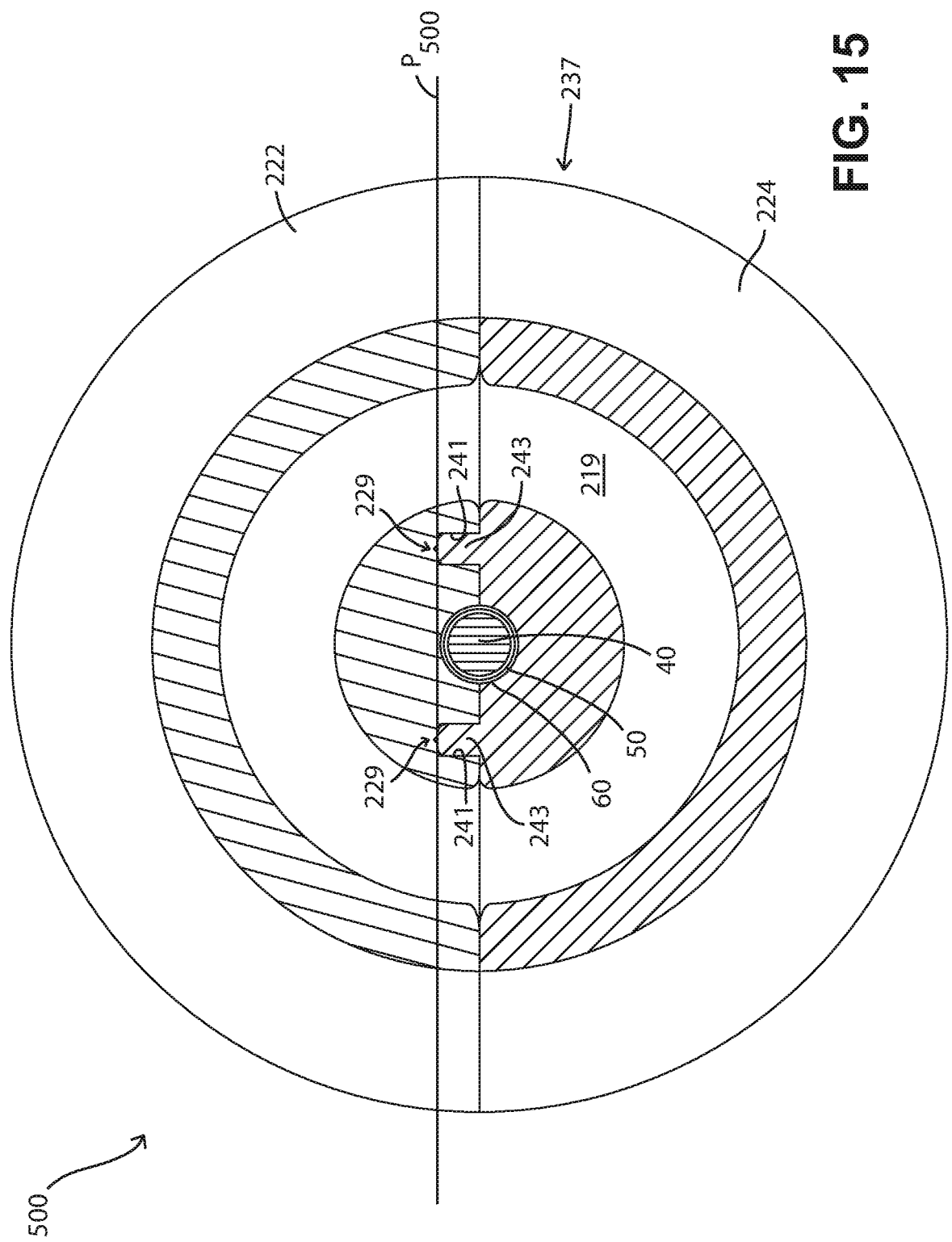
FIG. 15 is a cross-sectional view of the FIGS. 13A and 13B embodiment, taken along line 15-15 shown in FIG. 16.
Figure 16:
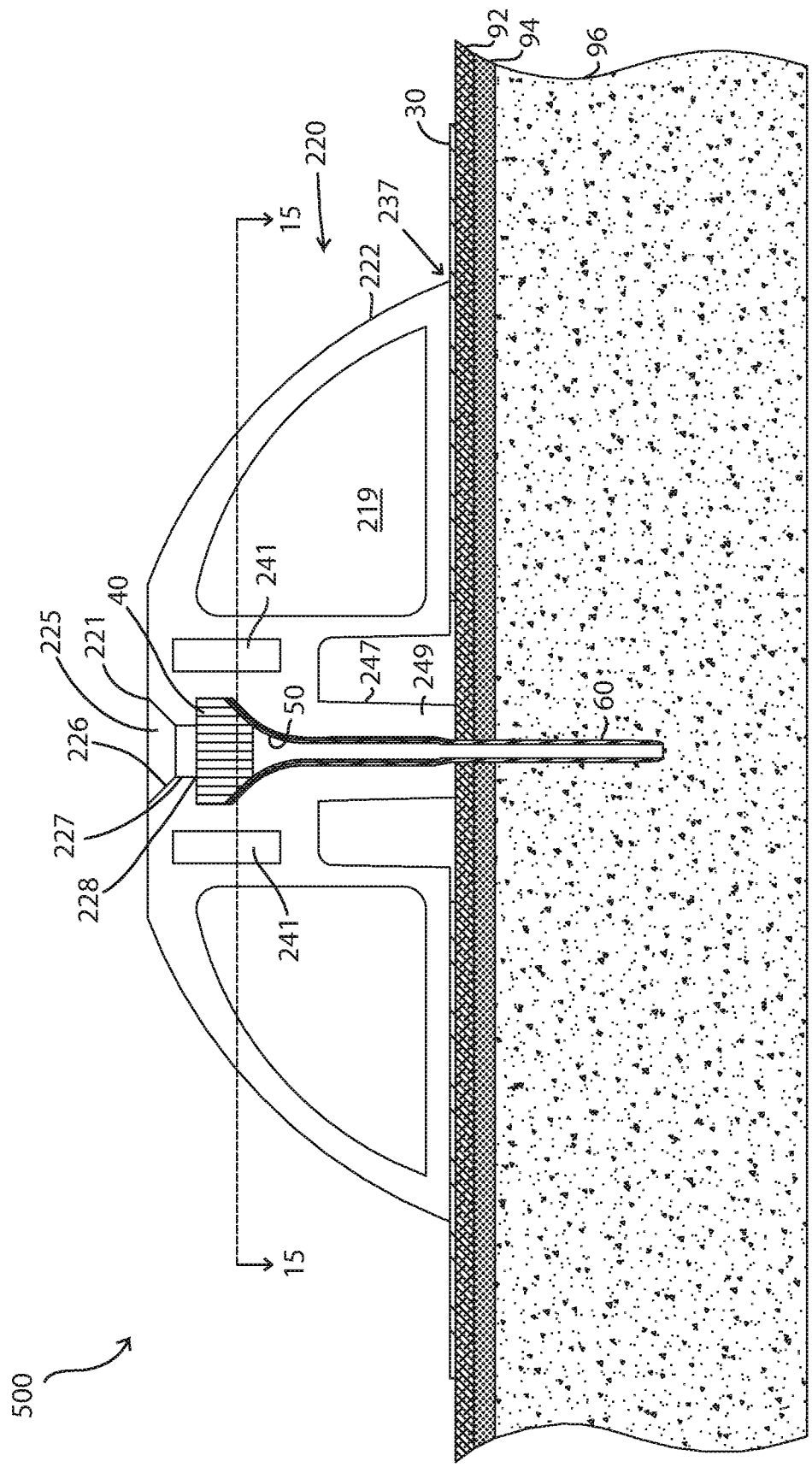
FIGS. 16 and 17 are cross-sectional views, respectively, of the two different elements that comprise the body of the FIGS. 13A and 13B fluid delivery device, taken along the plane at which the front surfaces of each element meet.
Figure 17:
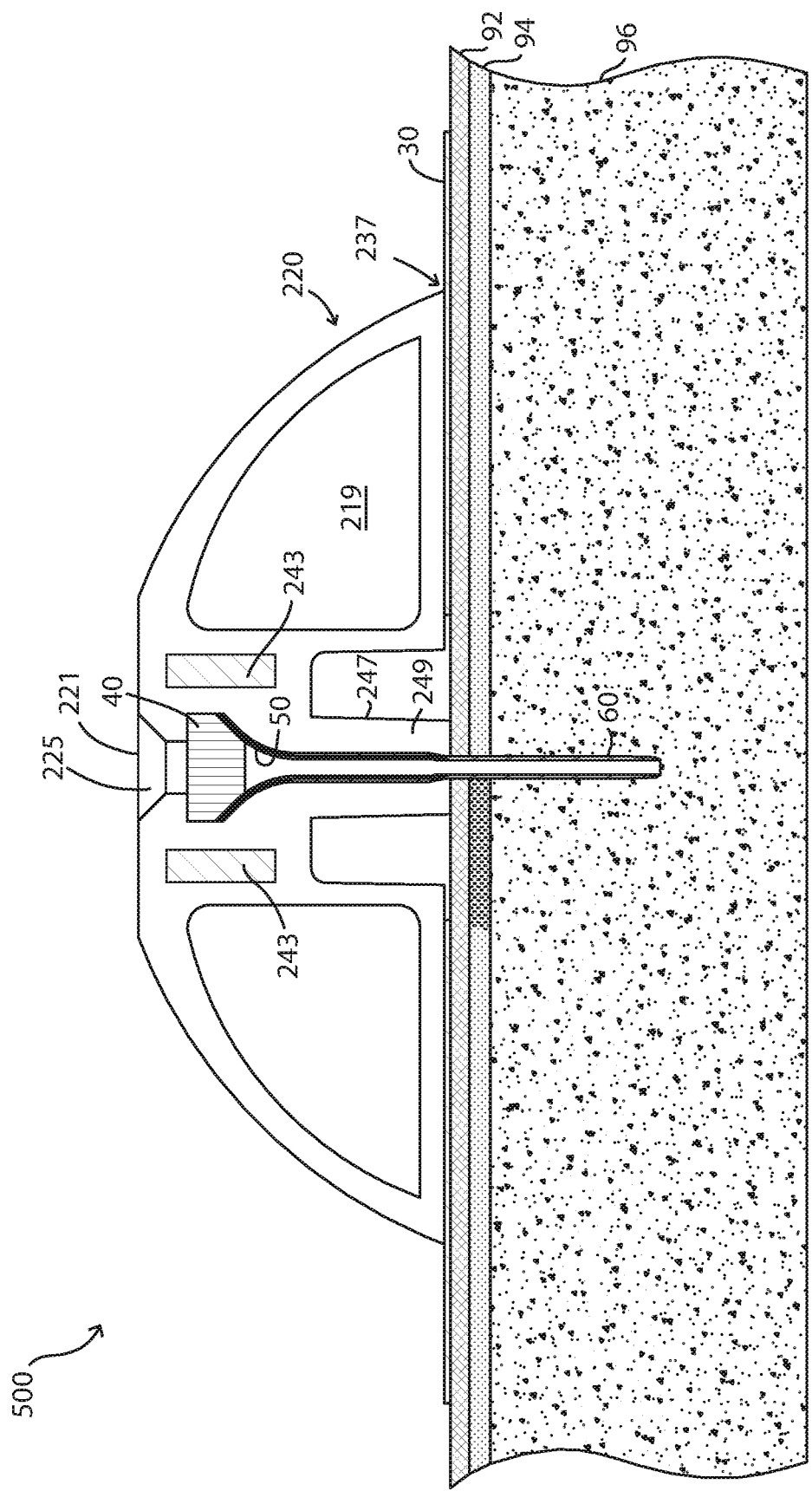

FIG. 14 shows fluid delivery device 500 in its assembled state. Elements 222 and 224 may be coupled to each other using any suitable attachment method, including any of those discussed above. For example, element 224 may include one or more male engagement members 243 that fit at least partially into female engagement recesses 241 of element 222, and ultrasonic welding may be used to permanently attach the two elements together at the location where the male engagement members meet the female engagement recesses. The members and recesses meet in the device plane $P_{500}$ shown in FIG. 15, which is taken along line 15-15 shown in FIG. 16.

The features of body 220 are similar in function to those of body 20, and thus have been numbered as they are for body 20 except for a 200 added to the number. Thus, inlet port 221 is similar in shape and function and to inlet port 21. Some of the features of body 220 are labeled in FIGS. 16 and 17. Although an identification feature is not shown as part of this embodiment, it may be provided in other embodiments. Although body 220 does not include any body cavity openings in fluid communication with body cavity 219, one or more body cavity openings similar to body cavity openings 17 from body 20 may be provided in other embodiments.

Figure 18:
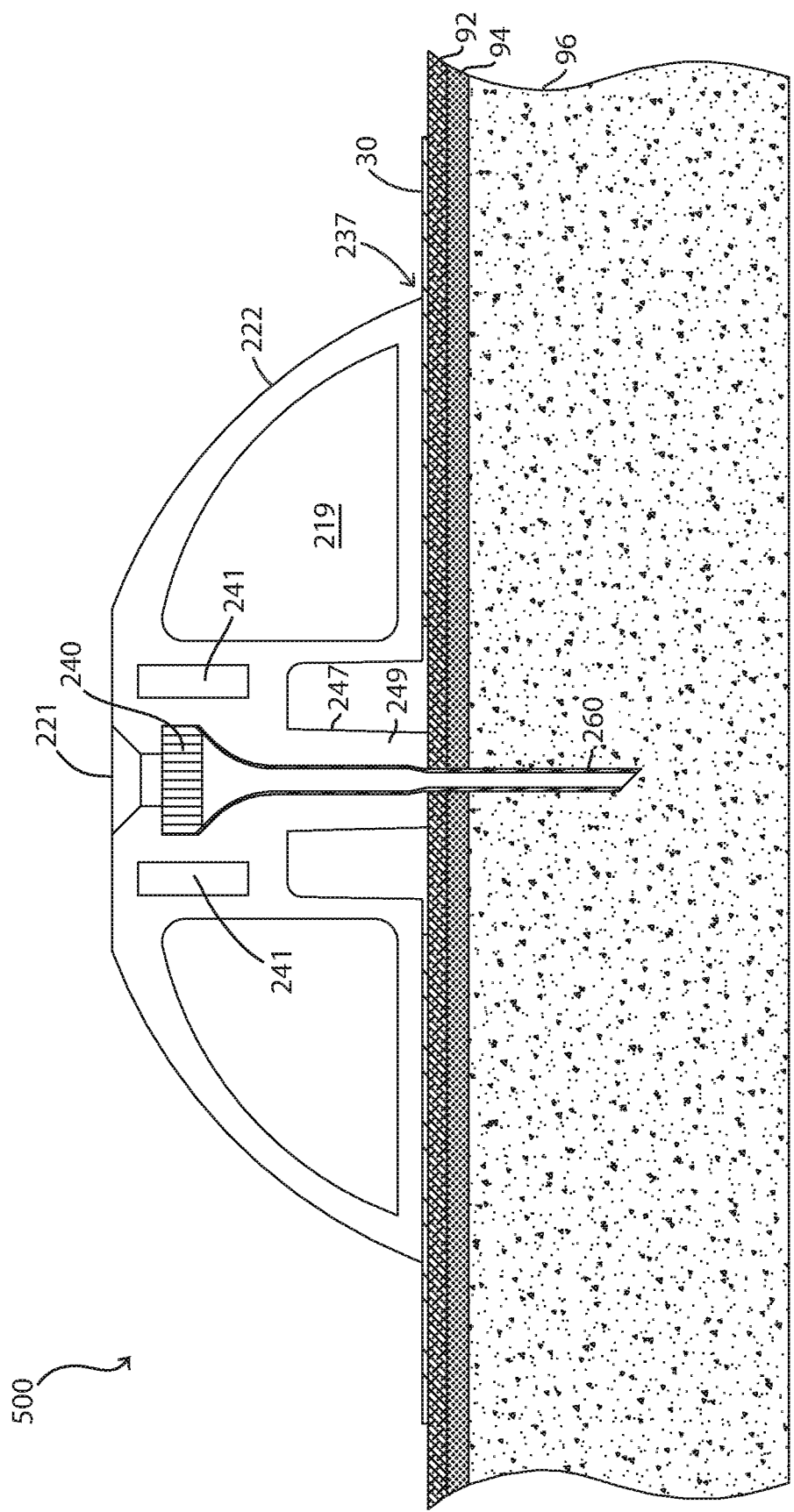
FIG. 18 shows an embodiment of a fluid delivery device similar to the one depicted in FIGS. 13A and 13B, but having a rigid cannula with a sharp end.
Figure 19:
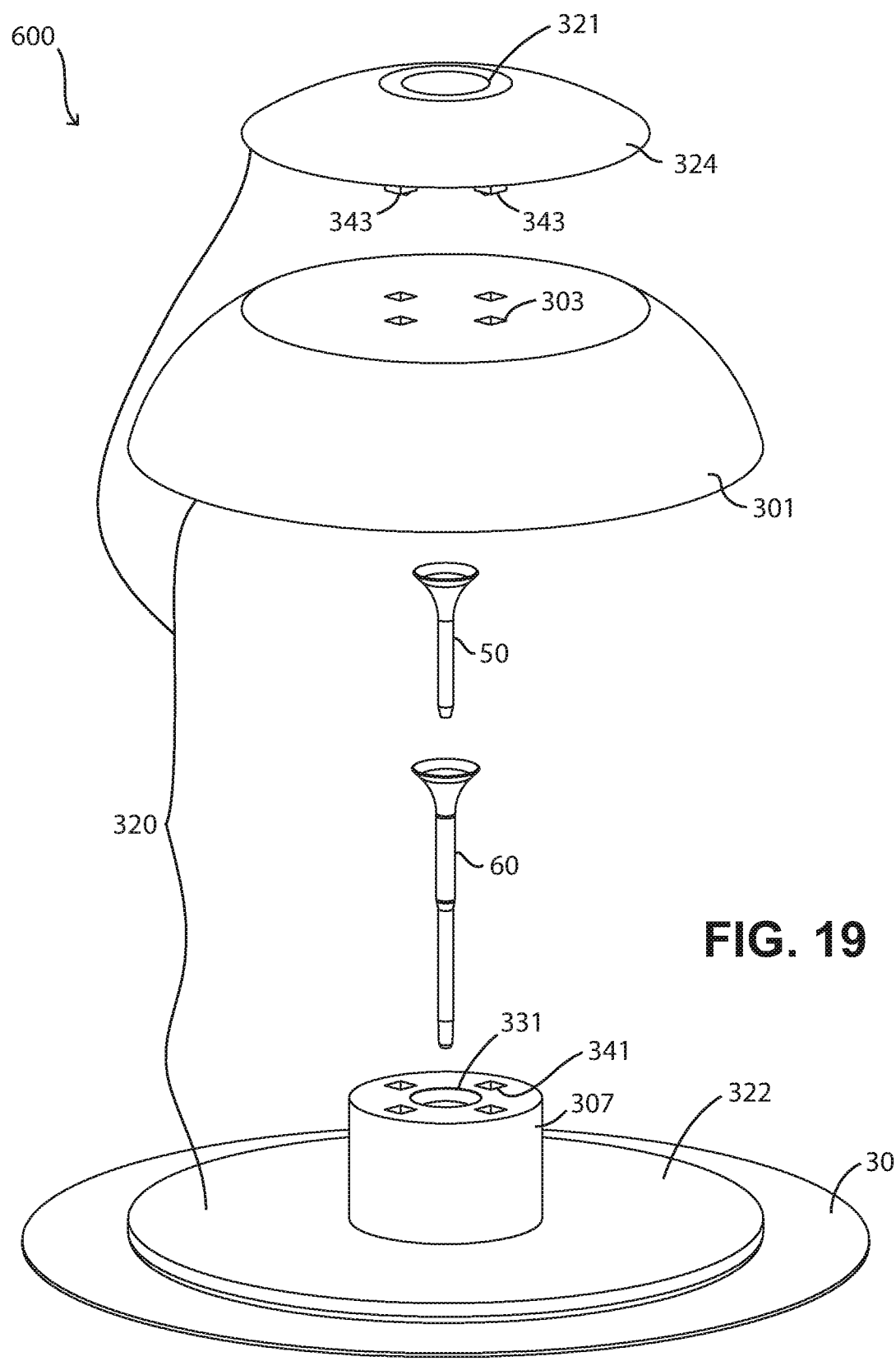
FIG. 19 is an exploded perspective view of an embodiment of the present fluid delivery devices that includes a body made from a majority (volumetrically) of septum material.
Figure 20:
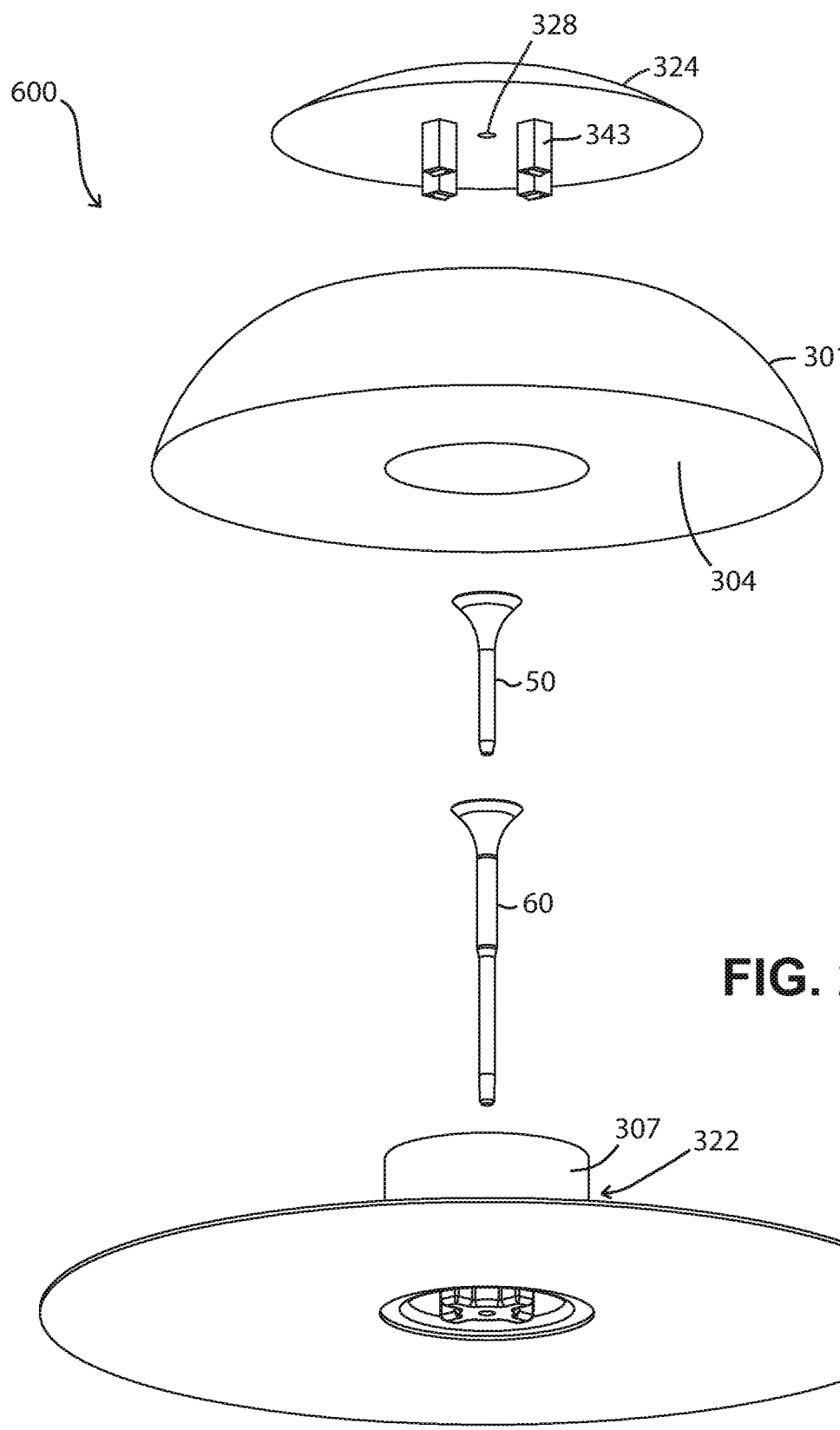
FIG. 20 is an exploded view of the FIG. 19 fluid delivery device, shown from the bottom perspective looking toward the top.
Figure 21:
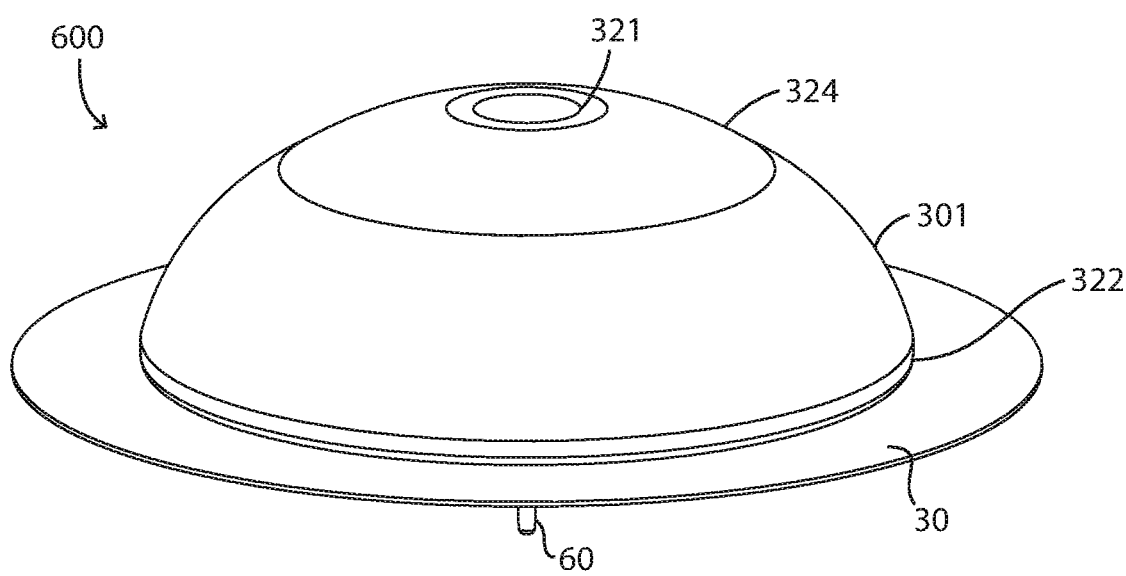
FIG. 21 is a perspective view of the assembled version of the fluid delivery device shown in FIG. 19.

Some embodiments of the present fluid delivery devices may use a cannula having a sharp end, which may be a centerpoint end or a beveled end (as shown) and which in some embodiments may be characterized as having a "tipped" end. Such a cannula may be open at one end, as shown in FIG. 18, or it may be closed at one end and have an opening somewhere along its shaft, upstream of the end. Such a cannula may be sufficiently rigid that its lower portion can be inserted into a living being without using an insertion needle, such as insertion needle 72 shown in FIG. 3. FIG. 18 depicts an embodiment of fluid delivery device 500 that includes such a cannula 260 and a septum 240. Septum 240 is shaped differently from septum 40 of fluid delivery device 100. A cannula and septum like those shown in FIG. 18 may be substituted for the cannula, needle guide and septum combinations of any of the present fluid delivery devices, such as cannula 60, needle guide 50 and septum 40 in the embodiment of fluid delivery device 100 depicted in FIGS. 1 and 2. Cannula 260 is illustrated as having a tapered portion at the exit opening of the body. In other embodiments, no such tapered portion exists (the same is true of cannula 360 show in FIG. 24, discussed below).

Figure 22:
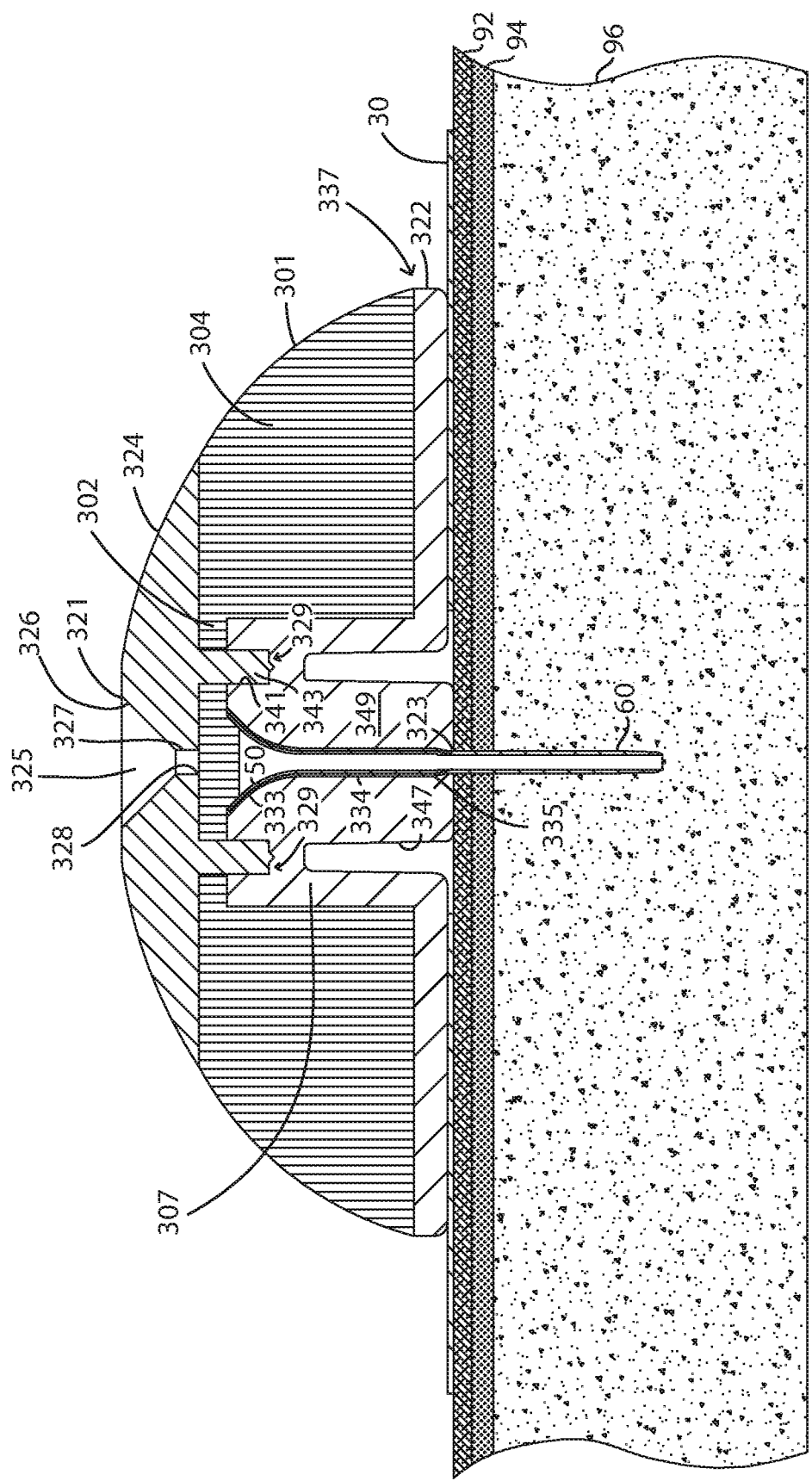
FIG. 22 is a cross-sectional view of the FIG. 19 fluid delivery device, taken along a plane that intersects two of the four cap element attachment protrusions of the base element of the depicted embodiment.

FIGS. 19-22 depict another of the present fluid delivery devices that has a multi-element body. Fluid delivery device 600 includes body 320, needle guide 50, cannula 60 and adhesive layer 30. Body 320 includes a base element 322, a cap element 324, and an intermediate element 301. Intermediate element 301 may be made from the same material (e.g., a self-sealing material such as an elastomeric material) as any of the present septa, and it may be sized relative to base element 322 and cap 324 such that a volumetric majority of body 320 is a self-sealing body material. The volumetric majority may be determined by any suitable test, including any suitable water displacement test. As FIG. 22 shows, a portion of the material from which intermediate element 301 may be formed comprises, or forms, a septum for the fluid delivery passageway of the device.

Cap element 324 may define an upper portion of the fluid delivery passageway 325. Specifically, cap element 324 includes entrance opening 321 (or inlet port 321, or inlet 321) of the device, a portion 326 that tapers inwardly, or in a downstream direction, and extends from entrance opening 321 to a straight-walled portion 327, which extends to the bottom surface of cap element 24 and terminates at cap element exit opening 328. Cap element 324 also includes cap element attachment protrusions 343 (four of them in this embodiment) that can be positioned in base element attachment recesses 341 of base element 322. The locations 329 at which the protrusions and recesses meet after attachment (through, e.g., ultrasonic welding) defines a device plane that is substantially perpendicular to an axis centered within a portion of fluid delivery passageway 325.

Intermediate element 301 includes multiple openings 303 sized to allow cap element attachment protrusions 343 to pass through them. As FIG. 22 shows, intermediate element 301 also includes an inner portion 302 and an outer portion 304. Inner portion 302 has a thickness, or a height, that is suitable for a septum. A central section of inner portion 302 is positioned in fluid delivery passageway 325, and acts as a septum for the passageway that substantially prevents fluid from flowing through the passageway (until an injection needle or the like is inserted through the septum).

Base element 322 may define a lower part of fluid delivery passageway 325. Base element 322 includes a base element entrance opening 331 from which a tapered wall portion 333 extends. Tapered wall portion 333, which may include an upper portion having a inward, or downstream, taper of constant angle and a lower portion that tapers, but not at a constant angle. Tapered wall portion 333 extends into straight-walled portion 334, which extends into another tapered portion 335 that terminates at exit opening, or exit port, 323. An inner portion 307 of base element 322 fits within the recess defined by the inner wall of outer portion 304 and the bottom of inner portion 302. Inner portion 307 includes inner central portion 349 and needle guard holding recess 347.

Figure 23:
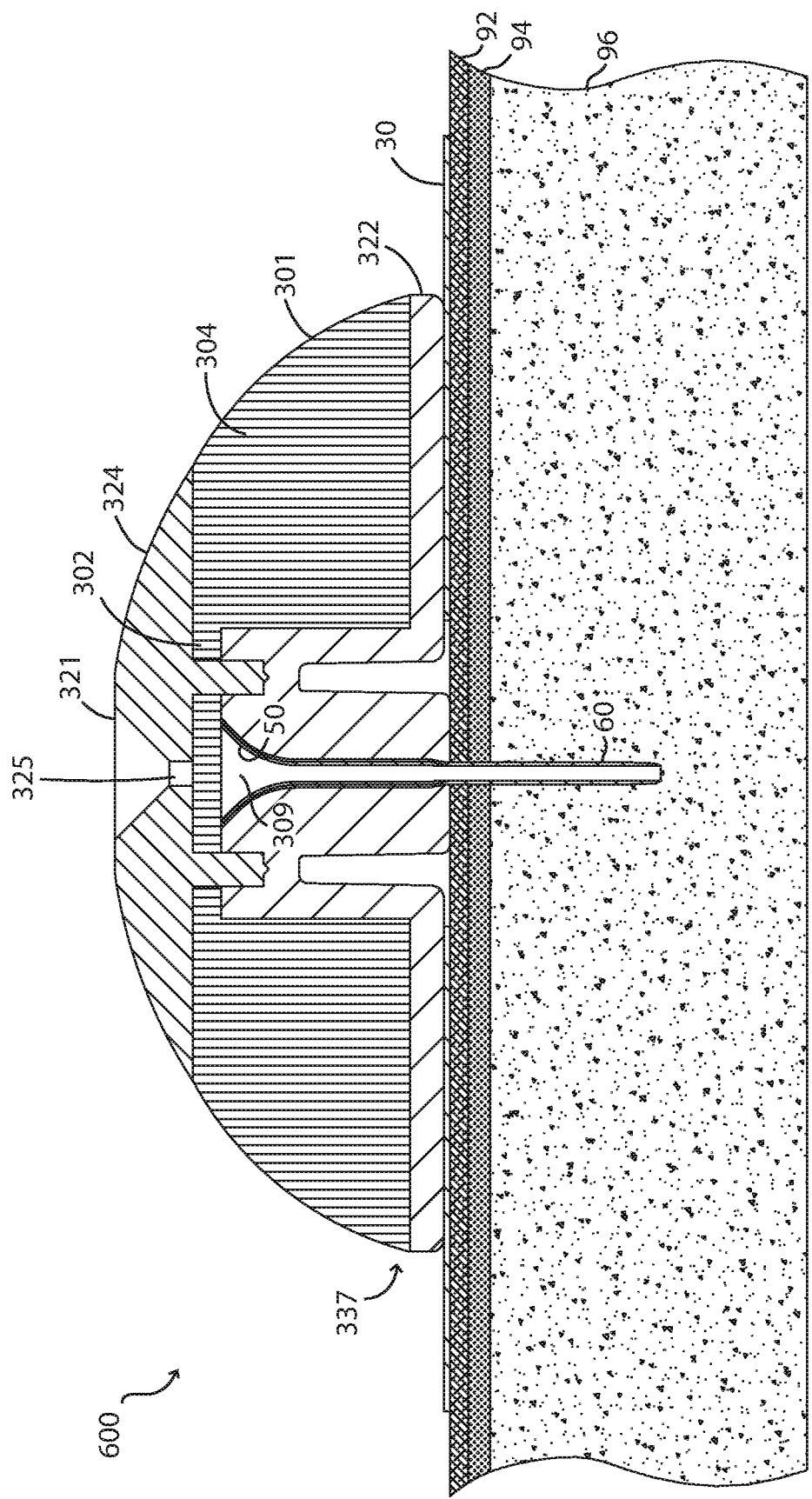
FIG. 23 is a cross-sectional view of a version of the FIG. 19 fluid delivery device that includes a septum extension that is positioned within the needle guide and cannula passageways.
Figure 24:
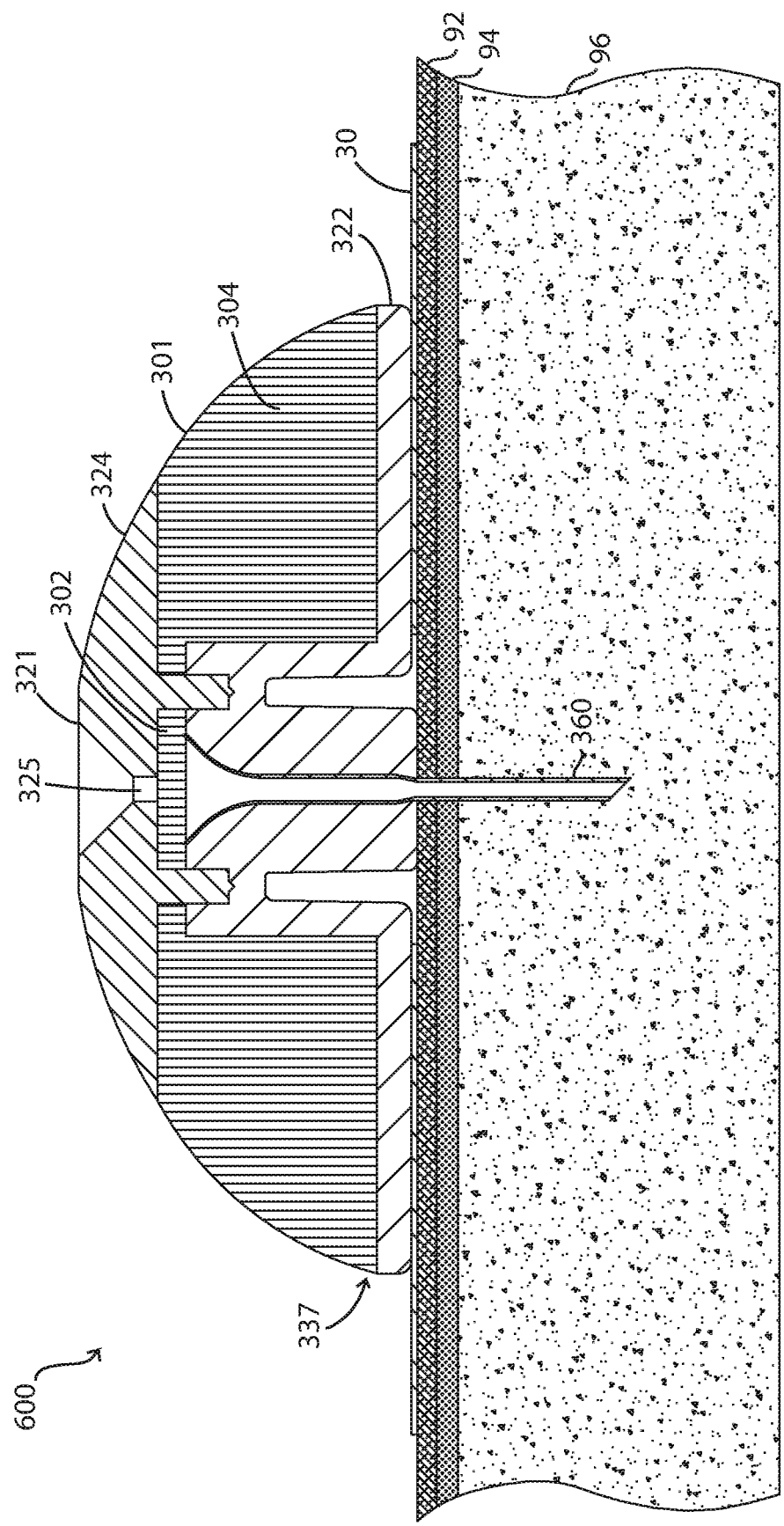
FIG. 24 is a cross-sectional view of a version of the FIG. 19 fluid delivery device that includes a rigid cannula having a sharp end.
Figure 25:
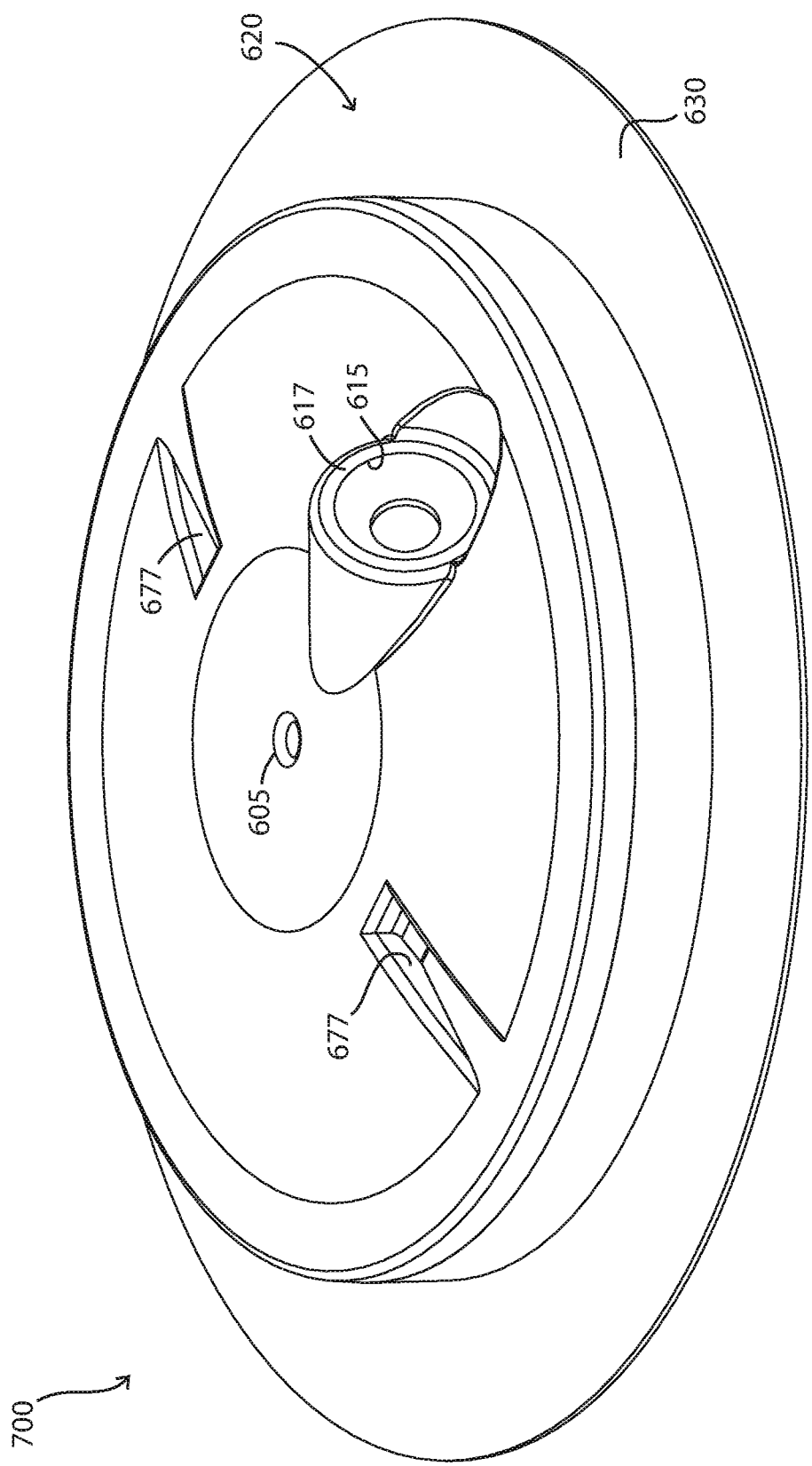
FIG. 25 is a perspective view of an embodiment of the present fluid delivery devices that includes a fluid delivery passageway having at least a portion that is oriented at an angle that is not parallel with the normal direction of insertion of the device.

Needle guide 50 extends up to and contacts an outer surface (a portion of the bottom surface, in this embodiment) of inner portion 302 of intermediate element 301. In this embodiment, the portion of the intermediate element 301 acting as the septum for the fluid delivery passageway does not include any material that is positioned within needle guide 50 or cannula 60. However, in other embodiments, inner portion 302 may include a septum protrusion positioned to fit within a portion of the needle guide (and, more specifically, the needle guide passageway) and the cannula (and, more specifically, the cannula passageway). The embodiment of fluid delivery device 600 shown in FIG. 23 includes such a protrusion: septum extension 309. FIG. 24 shows an example of a version of fluid delivery device 600 that includes a rigid cannula 360 having a sharp end.

Fluid delivery device 600 is another embodiment of a fluid delivery device having an outer perimeter (outer perimeter 337) and a cannula positioned such that any portion of the cannula that is above a user's skin when the device is used is positioned within the outer perimeter of the device. In this embodiment, a portion (more specifically, a majority) of the outer surface of body 320 has a convex shape.

Multi-Inlet Fluid Delivery Devices

Some embodiments of the present fluid delivery devices comprise multiple inlets, a fluid delivery passageway extending from each inlet, and a septum for each passageway where the septa are not in contact with each other. One of the fluid delivery passageways may be oriented at a non-zero angle to another of the passageways. One fluid delivery passageway may extend into another. Some multi-inlet embodiments comprise only one outlet. FIGS. 25-28 illustrate an example of an embodiment fitting each of these characterizations.

Fluid delivery device 700 includes a body 620 and an adhesive layer 630 attached to the body. As with all of the present fluid delivery devices, device 700 may also include an insertion device (not shown) and a needle guard 680. Body 620 includes rotation-restricting recesses 677, which function like the rotation-restricting recesses described above. The insertion device hub of any insertion device used with body 620 may be provided with complimentary rotation-restricting protrusions that function like those described above. Body 620 also includes a needle guard holding recess 647, which functions like the needle guard holding recess described above. In this embodiment, needle guard holding recess 647 is not a generally cylindrical recess—it extends around the base element of body 620 less than 360 degrees. Needle guard 680 has a notch 681 corresponding to the non-recessed portion of the base element, as shown in FIG. 26.

Body 620 includes two inlet ports, 605 and 615. Inlet port 605 (also inlet 605 or entrance opening 605) is centered within the cap element of body 620. Inlet port 605 also is perpendicular to the normal direction that fluid delivery device 700 will be installed to a living being (that direction being substantially parallel to cannula 660, discussed below), and to an axis (not shown) centered within a portion of the fluid delivery passageway extending from it. Inlet 615 is not centered within the cap element of body 620. Inlet 615 is oriented at an angle between zero and ninety degrees to the axis centered within the central fluid delivery passageway and to the normal direction of insertion of the device.

Figure 26:
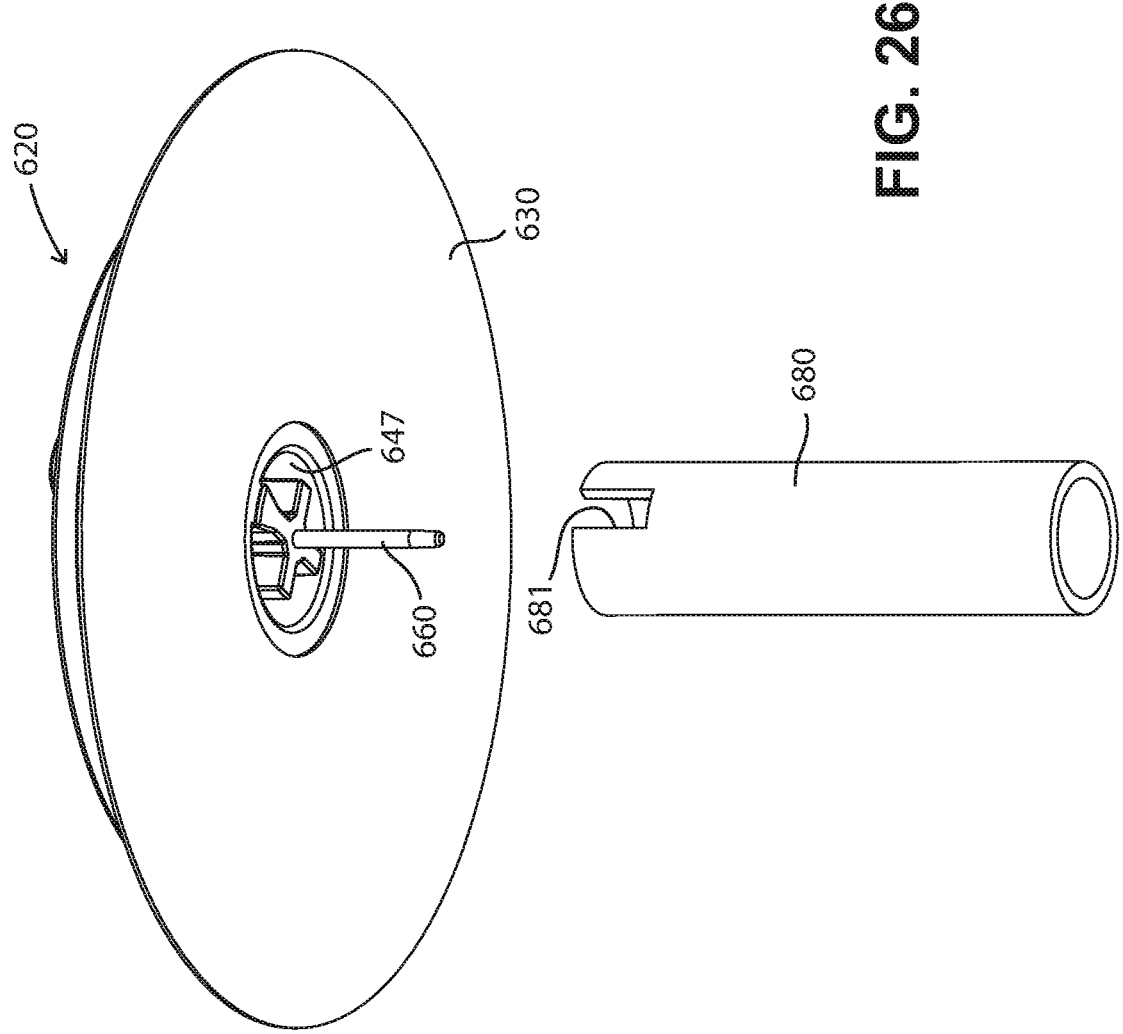
FIG. 26 is a perspective view from the bottom of the FIG. 25 fluid delivery device.
Figure 28:
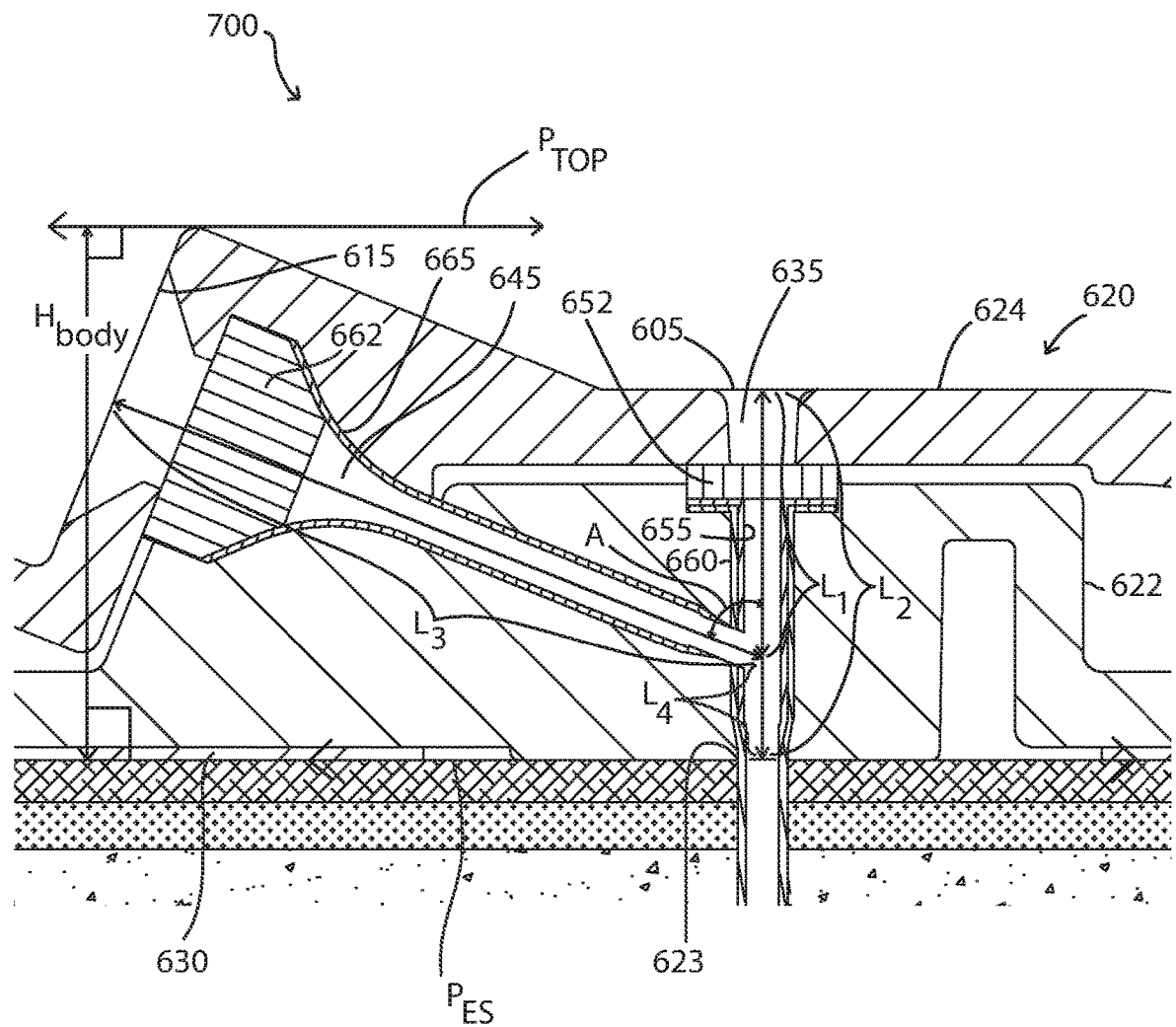
FIG. 28 is an enlarged detail of the FIG. 27 view.
Figure 29:
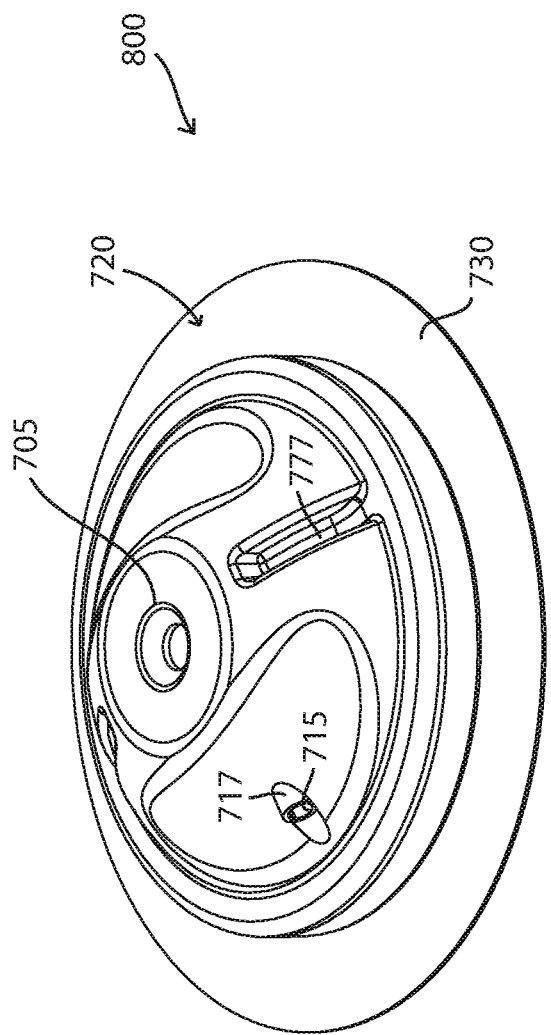
FIGS. 29 and 30 show different perspective views of a multi-inlet embodiment of one of the present fluid delivery devices that includes a passageway closing structure.
Figure 30:
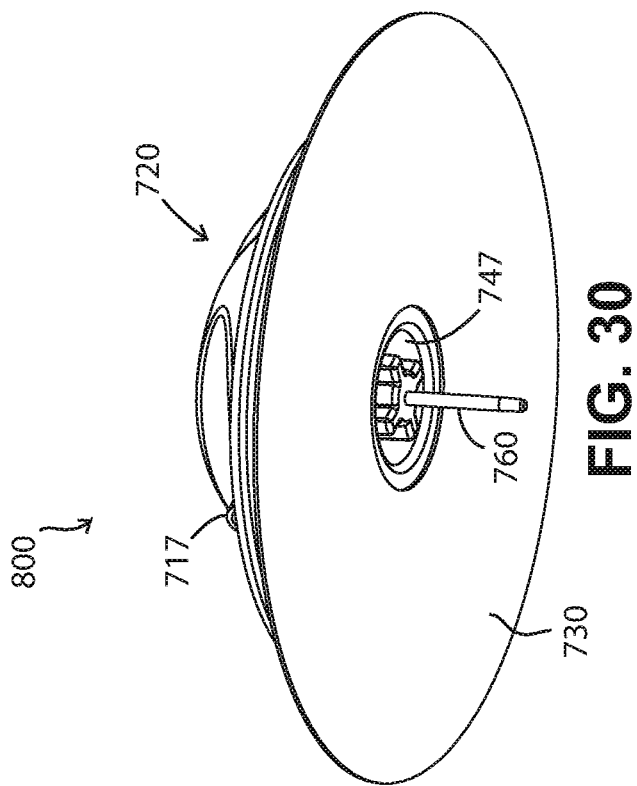

FIG. 26 shows that inlet 615 is bordered by an injection device shoulder 617 that is parallel to the plane in which inlet 615 lies. As FIG. 28 shows, injection device shoulder 617 may be configured such that a portion of an injection device, such as a portion of the plunger of a standard syringe, rests against it when an injection of fluid through inlet 615 takes place.

Figure 27:
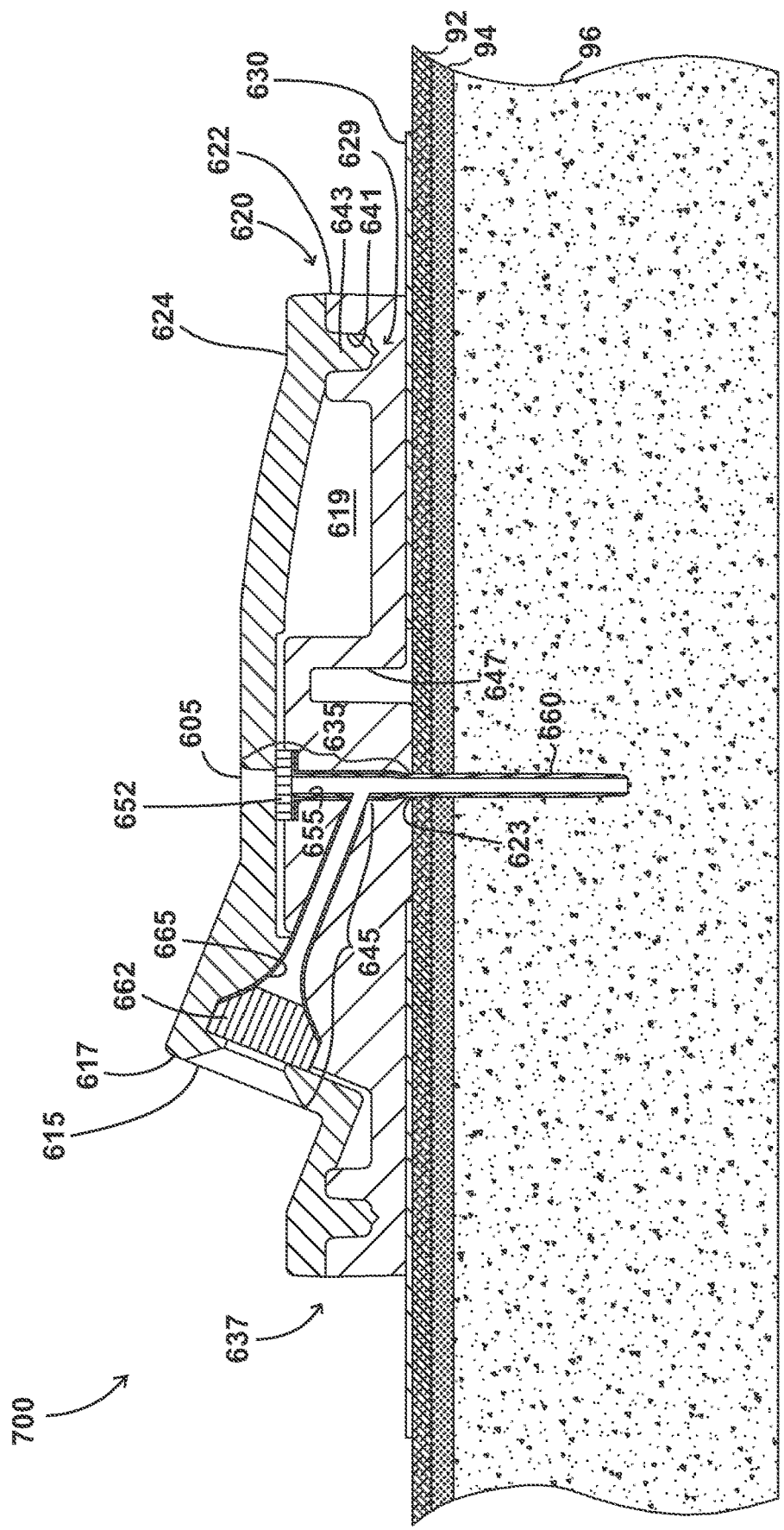
FIG. 27 is a cross-sectional view of the FIG. 25 fluid delivery device, taken along a plane that intersects the non-recessed portion of the bottom surface of the body.

FIG. 27 shows fluid delivery device 700 in cross section and installed to a living being. As this figure shows, body 620 includes a cap element 624 and a base element 622. Cap element 624 includes a cap element attachment protrusion 643, which functions like the cap element protrusion described above. Base element 622 includes a base element attachment recess 641, which functions like the base element attachment recess described above. The cap and base elements of this embodiment may be permanently attached to each other using any of the techniques described above. The two elements may be assembled in a device plane that is perpendicular to the central fluid delivery passageway's axis and to the normal insertion direction of the device. The device plane is defined by the location 629 where the base and cap elements are attached to each other.

Body 620 includes fluid delivery passageway 635 extending to exit opening 623 from inlet 605, and fluid delivery passageway 645 extending from inlet 615 into fluid delivery passageway 635 at a non-zero angle, such as an angle A (see FIG. 28) that is greater than zero and less than or equal to 90 degrees. As FIGS. 27 and 28 show, a portion of inlet 615 is downstream of inlet 605, and a portion of inlet 615 is upstream of inlet 605. Device 700 also includes a needle guide 665, which has a portion positioned within fluid delivery passageway 645. Needle guide 665 is coaxial with fluid delivery passageway 645 in this embodiment. Device 700 also includes a septum 662 positioned within fluid delivery passageway 645. Septum 662 has an accessible portion that is recessed downstream of inlet 615, and has a portion positioned within needle guide 665.

Fluid delivery device 700 includes another needle guide 655 that has a portion positioned within, and is coaxial with, fluid delivery passageway 635. Device 700 also includes a cannula 660 having a portion (in this embodiment, an upper portion) positioned within fluid delivery passageway 635. In this embodiment, fluid delivery passageway 635, needle guide 655 and cannula 660 are coaxial with each other. Device 700 also includes another septum 652, which is separate from septum 662, having a portion positioned within fluid delivery passageway 635, but no portion (in this embodiment) positioned within either needle guide 655 or cannula 660. Septum 652 is wedged between a portion of cap element 624 and a portion of base element 622 and helps to seal body cavity 619, as does septum 662. Both cannula 660 and needle guide 655 have a side opening (unnumbered) that allows fluid to enter fluid delivery passageway 635 from passageway 645. Body 620 is characterized by outer perimeter 637.

FIG. 28 is an enlarged detail of a portion of the FIG. 27 view, and shows that fluid delivery device 700 is an embodiment of a device in which the length of the fluid delivery passageway of the body of the device is greater than the height of the device above the device's engagement surface. This figure shows that the engagement surface of the device, which is the bottom surface of adhesive layer 630, lies in plane $P_{ES}$. When device 700 is used, the engagement surface may be curved to fit a user's skin, but in at least one orientation the engagement surface lies in plane $P_{ES}$. Fluid delivery passageway 645 is oriented at a non-perpendicular angle to (a) the engagement surface of device 700, and (b) the bottom surface of body 620, which is parallel to the engagement surface.

The topmost plane $P_{TOP}$ in which the top of device 700 lies is parallel to plane $P_{ES}$. The body has a height $H_{body}$ characterized by the distance between planes $P_{TOP}$ and $P_{ES}$ taken along a line extending perpendicularly between both planes. Fluid delivery passageway 635 has a length $L_2$ that comprises length $L_1$, which extends between inlet 605 and the location at which the axis centered within fluid delivery passageway 645 meets the axis centered within fluid delivery passageway 635, and length $L_4$, which extends from the end of $L_1$ to exit opening 623 of body 620. The longest fluid delivery passageway within body 620 comprises a combination of fluid delivery passageways 645 and 635, and has a length of $L_3$ (which extends from inlet 615 to the location defined by the downstream end of $L_1$) plus $L_4$.

Some embodiments of the multi-inlet fluid delivery devices may be configured for connection to an infusion pump, and may include a passageway closing structure that can be moved between positions. In one position, the passageway closing structure inhibits some fluid flow through one of the passageways while allowing it through another, and in another position the opposite effect may be achieved. The passageway closing structure may be biased to one of the positions. FIGS. 29-34 depict different aspects of such a fluid delivery device.

Fluid delivery device 800 is similar in some respects to the embodiment of fluid delivery device 100 depicted, for example, in FIGS. 1-2B. Fluid delivery device 800 includes a body 720 having two fluid delivery passageways, and an adhesive layer 730 attached to the body. Device 800 also may include an insertion device, like insertion device 70, and a needle guard, like needle guard 80. Body 720, and more specifically the cap element of the body, may include rotation-restricting recesses 777 that function like the rotation-restricting recesses described above. Any insertion device used with body 720 may be provided with complimentary rotation-restricting protrusions that function like those described above. Body 720 also includes a needle guard holding recess 747, which functions like the needle guard holding recesses described above.

Body 720 includes two inlet ports, 705 and 715. Inlet port 705 (also inlet 705 or entrance opening 705) is centered within the cap element of body 720. Inlet port 705 also is perpendicular to the normal direction that fluid delivery device 800 will be installed to a living being, and to an axis (not shown) centered within a portion of the fluid delivery passageway extending from it. Inlet 715 is not centered within the cap element of body 720. Inlet 715 is oriented at an angle of ninety degrees to the axis centered within the central fluid delivery passageway and to the normal direction of insertion of the device.

Body 720 also includes an inlet fitting 717 extending downstream from inlet 715. Inlet fitting 717 defines an outer portion of the laterally-oriented fluid delivery passageway of body 720, and may be adapted to be releasably coupled to an infusion pump connector fitting. For example, inlet fitting 717—which is depicted generically in FIGS. 29-34—may comprise a male or female Luer fitting that can be engaged with a complimentary female or male Luer fitting coupled to a pump through tubing. Inlet fitting 717 may have any configuration suited for being releasably coupled to an infusion pump connector fitting.

Figure 31:
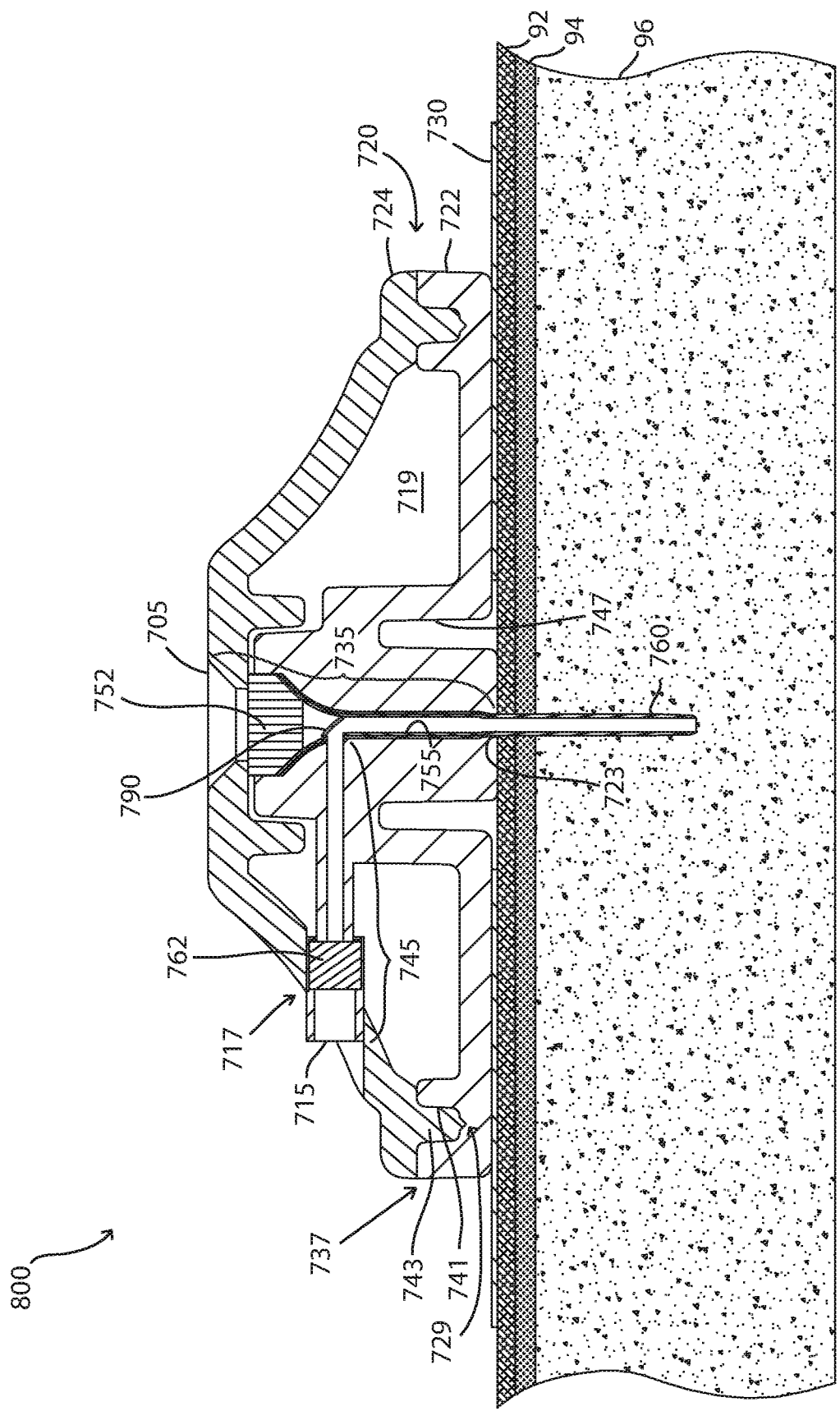
FIG. 31 is a cross-sectional view of the FIGS. 29 and 30 fluid delivery device, taken in a plane that intersects the middles of both inlets, and shows the passageway closing structure in its biased position.

FIG. 31 is a cross-sectional view of fluid delivery device 800 in an inserted position. As this figure shows, body 720 includes a cap element 724 and a base element 722. Cap element 724 includes a cap element attachment protrusion 743, which functions like the cap element protrusions described above. Base element 722 includes a base element attachment recess 741, which functions like the base element attachment recesses described above. The cap and base elements of this embodiment may be permanently attached to each other using any of the techniques described above. The two elements may be assembled in a device plane that is perpendicular to the central fluid delivery passageway's axis and to the normal insertion direction of the device. The device plane is defined by the location 729 where the base and cap elements are attached to each other.

FIG. 31 shows that body 720 includes fluid delivery passageway 735 extending from inlet 705 to exit opening 723, and fluid delivery passageway 745 extending from inlet 715 into fluid delivery passageway 735 at a non-zero angle (such as 90 degrees) that can be measured between an axis centered within a portion of fluid delivery passageway 735 and an axis centered within a portion of fluid delivery passageway 745. Device 800 also includes a septum 762 positioned within fluid delivery passageway 745. Septum 762 has an accessible portion that is recessed downstream of inlet 715. The size of septum 762 can be varied to suit the configuration or configurations of the infusion pump connector fittings with which device 800 works. Such infusion pump connector fittings generally include a septum-piercing element through which fluid flows, and the septum thickness and style (e.g., split vs. non-split) may be configured to work with a given septum-piercing element.

Fluid delivery device 800 includes needle guide 755 that has a portion positioned within, and is coaxial with, fluid delivery passageway 735. Device 800 also includes a cannula 760 having a portion (in this embodiment, an upper portion) positioned within and coaxial with fluid delivery passageway 735. In this embodiment, fluid delivery passageway 735, needle guide 755 and cannula 760 are coaxial with each other. Device 800 also includes another septum 752, which is separate from septum 762, having a portion positioned within fluid delivery passageway 735. Septum 752 is configured like septum 40 from the embodiment of fluid delivery device 100 shown, for example, in FIGS. 1-2B. Body 720 also includes a sealed body cavity 719.

Both cannula 760 and needle guide 755 have a side opening (unnumbered) that allows fluid to enter fluid delivery passageway 735 from passageway 745. Body 720 is characterized by outer perimeter 737.

FIGS. 31-34 show that fluid delivery device 800 also includes a passageway closing structure 790. In this embodiment, the passageway closing structure is disposed in fluid delivery passageway 735 (and, in this embodiment, within the needle guide passageway) and is coupled to needle guide 755. Passageway closing structure 790 in this embodiment is biased toward a first position, shown in FIG. 31, that at least partially blocks, or obstructs, fluid delivery passageway 735 while leaving fluid delivery passageway 745 substantially (and, in this embodiment, completely) unobstructed. As a result, when an infusion pump is coupled to device 800 via inlet fitting 717, fluid can flow from the pump and through fluid delivery passageway 745, into fluid delivery passageway 735, and through a lower portion of fluid delivery passageway 735. At the same time, passageway closing structure 790 prevents fluid from flowing unobstructed in a downstream direction through the portion of fluid delivery passageway 735 that is upstream of the junction location of the two passageways.

Passageway closing structure 790 may have any suitable shape. For example, it may have an edge that is curved to match the configuration of the portion of the inner wall of needle guide 755 that it contacts or approaches in the first position. Furthermore, if passageway closing structure 790 is structured to contact needle guide 755 (opposite its coupling location to needle guide 755) in order to at least partially block fluid flow through fluid delivery passageway 735, the passageway closing structure may be coated with a material that helps to increase the friction between it and needle guide 755 in order to help it maintain its first position. Passageway closing structure 790 may be made from any suitable material. For example, passageway closing structure 790 may be made from the same material as needle guide 755 in some embodiments, and from a different material in other embodiments. Passageway closing structure may be biased to the first position shown in FIG. 31 in any suitable fashion. For example, passageway closing structure 790 may be biased using a spring, superelastic or shape memory properties of a material, or magnetic forces. Other biasing techniques may be used. Furthermore, in other embodiments, passageway closing structure 790 may be biased to the second position shown in FIG. 32 such that it is moved to the FIG. 31 first position by fluid flowing into fluid delivery passageway 735 from fluid delivery passageway 745, such as fluid driven by a pump.

Figure 32:
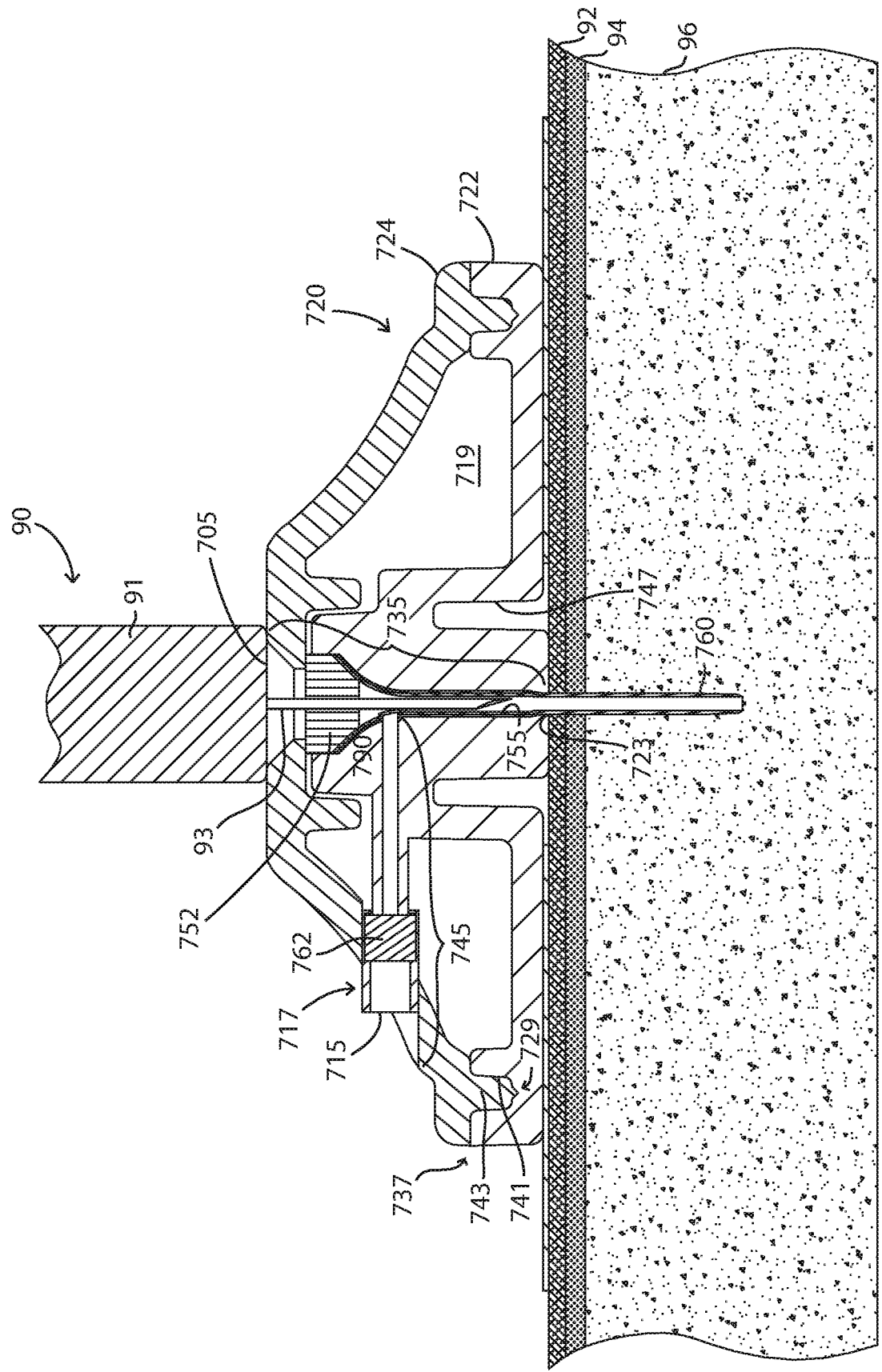
FIG. 32 is another cross-sectional view of the FIGS. 29 and 30 fluid delivery device, showing the passageway closing structure in another position.

FIG. 32 depicts the result of moving passageway closing structure 790 to a second position using an injection device (such as injection device 90) in which the passageway closing structure at least partially (more preferably substantially, and most preferably completely) blocks fluid from flowing through fluid delivery passageway 745, while allowing fluid to flow through fluid delivery passageway 735. More specifically, passageway closing structure 790 in the second position at least partially (more preferably substantially, and most preferably completely) blocks fluid from flowing through fluid delivery passageway 745 and out of body 720, while allowing fluid to flow through fluid delivery passageway 735 and out of body 720.

Figure 34:
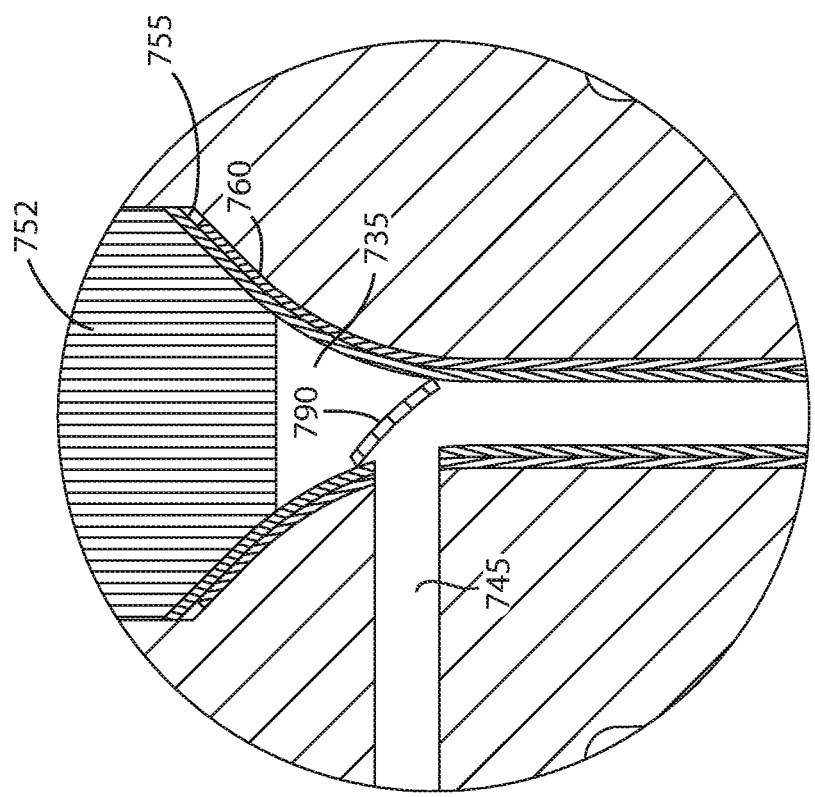
FIG. 34 is an enlarged view of a detail from FIG. 31, in which the passageway closing structure has returned to its normally-biased position after an injection needle has been removed.
Figure 33:
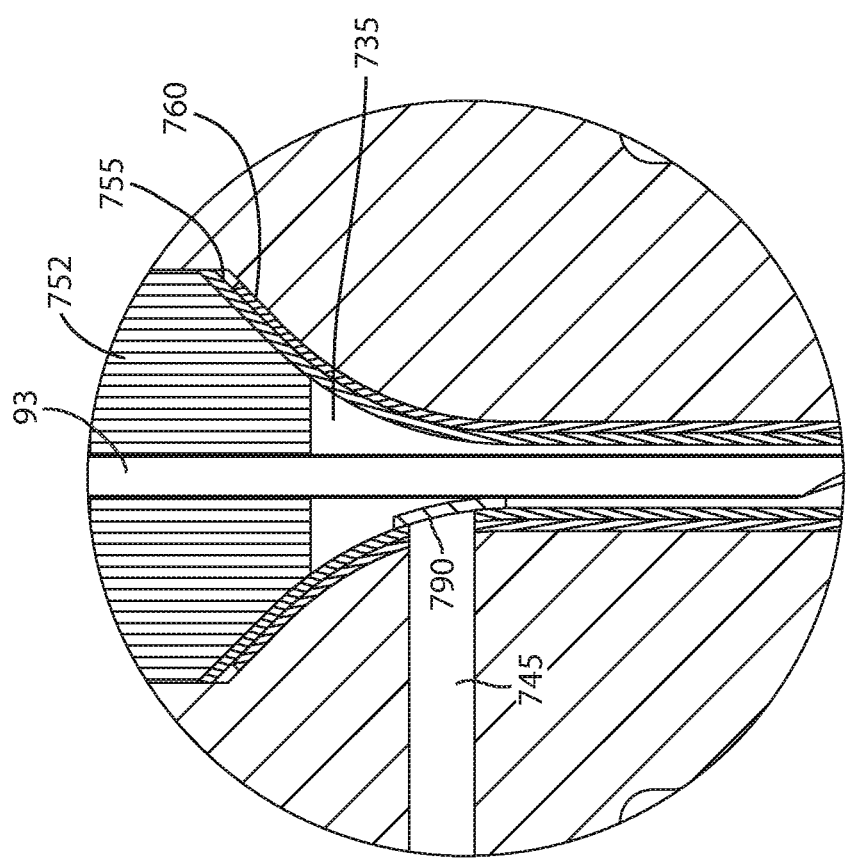
FIG. 33 is an enlarged view of a detail from FIG. 32.

FIGS. 33 and 34 are enlarged detail views of the cross-sections shown in FIGS. 31 and 32, respectively. They show close-ups of passageway closing structure 790 in the second position (FIG. 33) as a result of the force applied by injection needle 93, and in the first position (FIG. 34) again after the needle has been removed.

Figure 36:
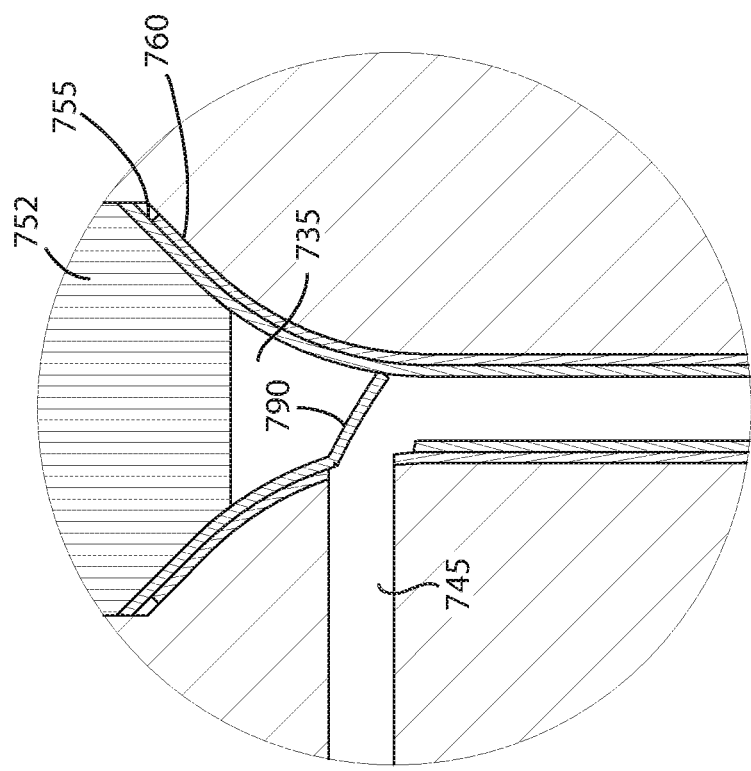
FIGS. 35 and 36 are enlarged detail views similar to FIGS. 33 and 34, and depict another embodiment of the present passageway closing structures.
Figure 35:
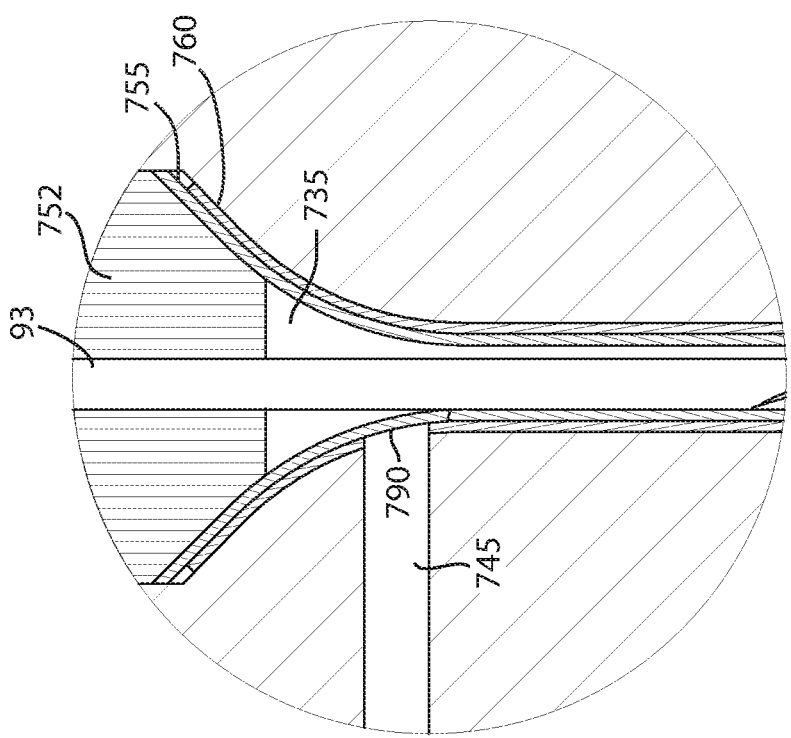
Figures 37, 38:
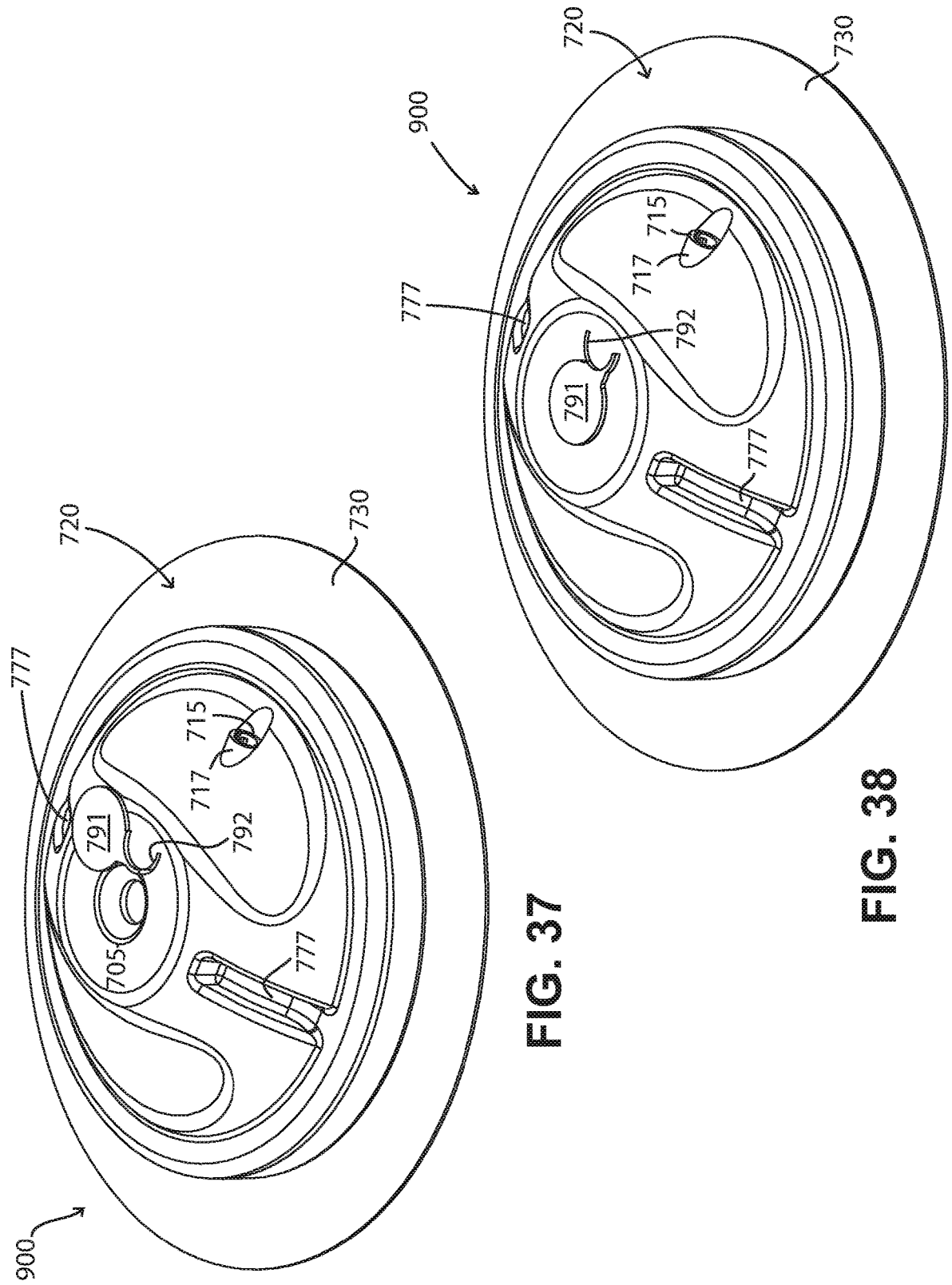
FIG. 37 is a perspective view of another multi-inlet embodiment of one of the present fluid devices that includes a passageway closing structure, showing the passageway closing structure in one position.
FIG. 38 is a perspective view of the FIG. 37 fluid delivery device, showing the passageway closing structure in another position.

FIGS. 35 and 36 show enlarged detail views of another embodiment of passageway closing structure 790. In this embodiment, passageway closing structure 790 is made from the same material as needle guide 755, and, more specifically, is cut from (stamped from, etc.) the needle guide material. In this embodiment passageway closing structure 790 is disposed in fluid delivery passageway 735. It also is disposed in the needle guide passageway in the first position (FIG. 36) but not the second position (FIG. 35). In this embodiment, needle guide 755 and passageway closing structure 790 may be made from a material, such as a nickel-titanium alloy, that is treated to have superelastic properties such that it can be biased (e.g., resiliently biased) in a first position, forced into a second position, and then returns substantially to the first position when the second position force is removed.

Another multi-inlet embodiment that includes a passageway closing structure is depicted in FIGS. 37-43. Fluid delivery device 900 is similar to fluid delivery device 800, except that device 900 includes passageway closing structure 791 instead of passageway closing structure 790. Passageway closing structure 791 may achieve the same result as passageway closing structure 790, but does so in a different way. The embodiments of cap element 724 and base element 722 of device 900 are similar to the embodiments of those elements in device 800, except that they are configured to work with passageway closing structure 791. As a result, both elements include a slot in which passageway closing structure 791 can slide.

Figure 39:
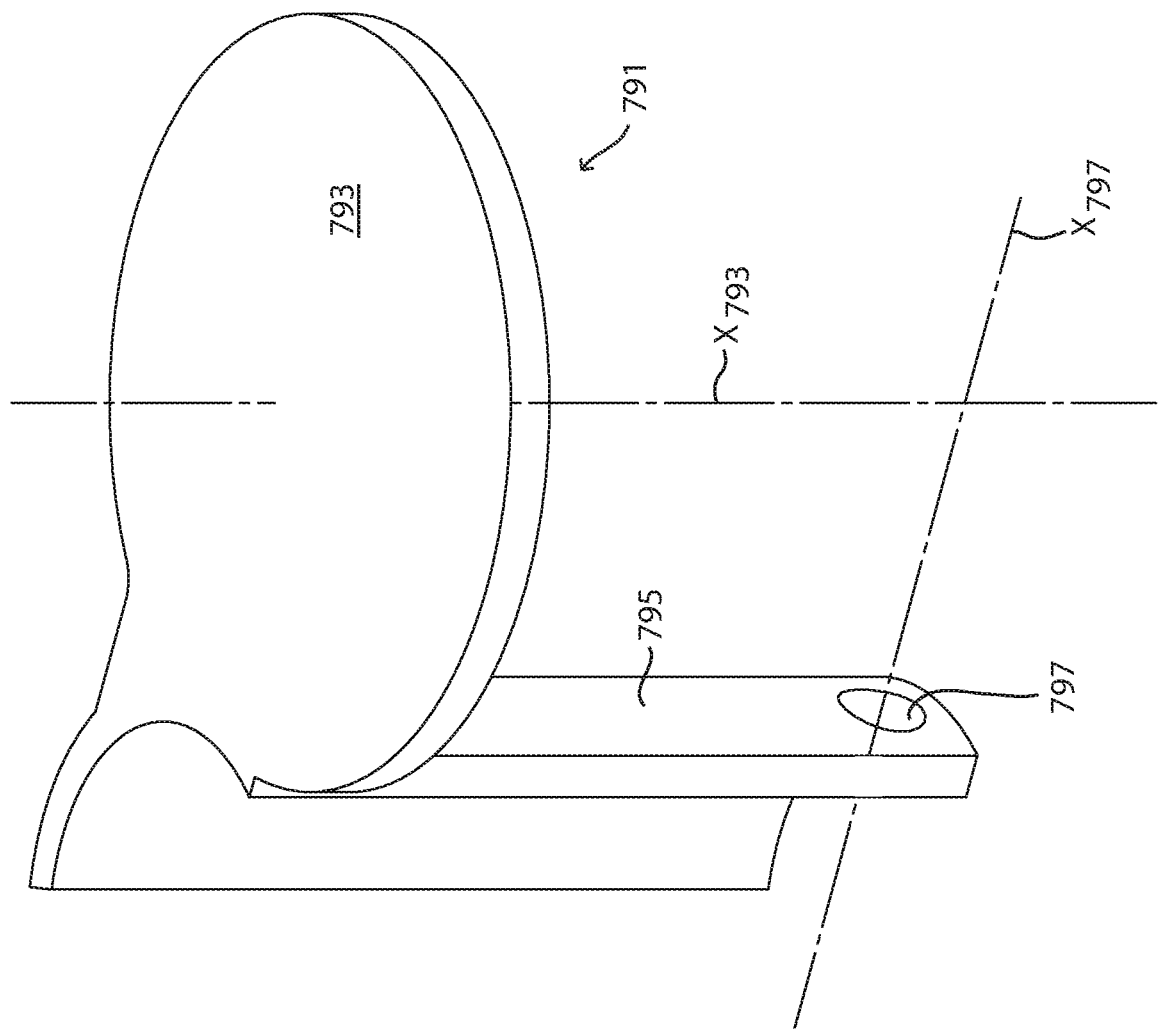
FIG. 39 is a perspective view of the passageway closing structure of the FIG. 37 fluid delivery device.

Passageway closing structure 791 is shown in perspective in FIG. 39. It includes a passageway blocking cap 793 that is configured to reside outside of fluid delivery passageway 735 in the first position, which at least partially (more preferably substantially, and most preferably completely) blocks fluid from flowing through fluid delivery passageway 735 and out of body 720. Cap 793 achieves this blocking because it is positioned to prevent fluid from entering fluid delivery passageway 735 through inlet 705 by covering inlet 705. Cap 793 is shaped like a partial disc that has a diameter greater than the diameter of inlet 705. Passageway blocking cap 793 is coupled to (and, in this embodiment, integrally formed with) passageway blocking section 795, which is shaped (in this embodiment) like part of a cylinder. Passageway blocking cap 793 is oriented substantially perpendicular to the axis about which section 795 pivots, or rotates. Passageway blocking section 795 includes an opening 797 through which fluid from fluid delivery passageway 745 can flow when passageway closing structure 791 is in its first position. As FIG. 39 shows, passageway closing structure 791 may be configured such that, when in its first position, an axis $X_{793}$ that runs through the center of cap 793 intersects an axis $X_{797}$ that runs through the center of opening 797.

Figure 40:
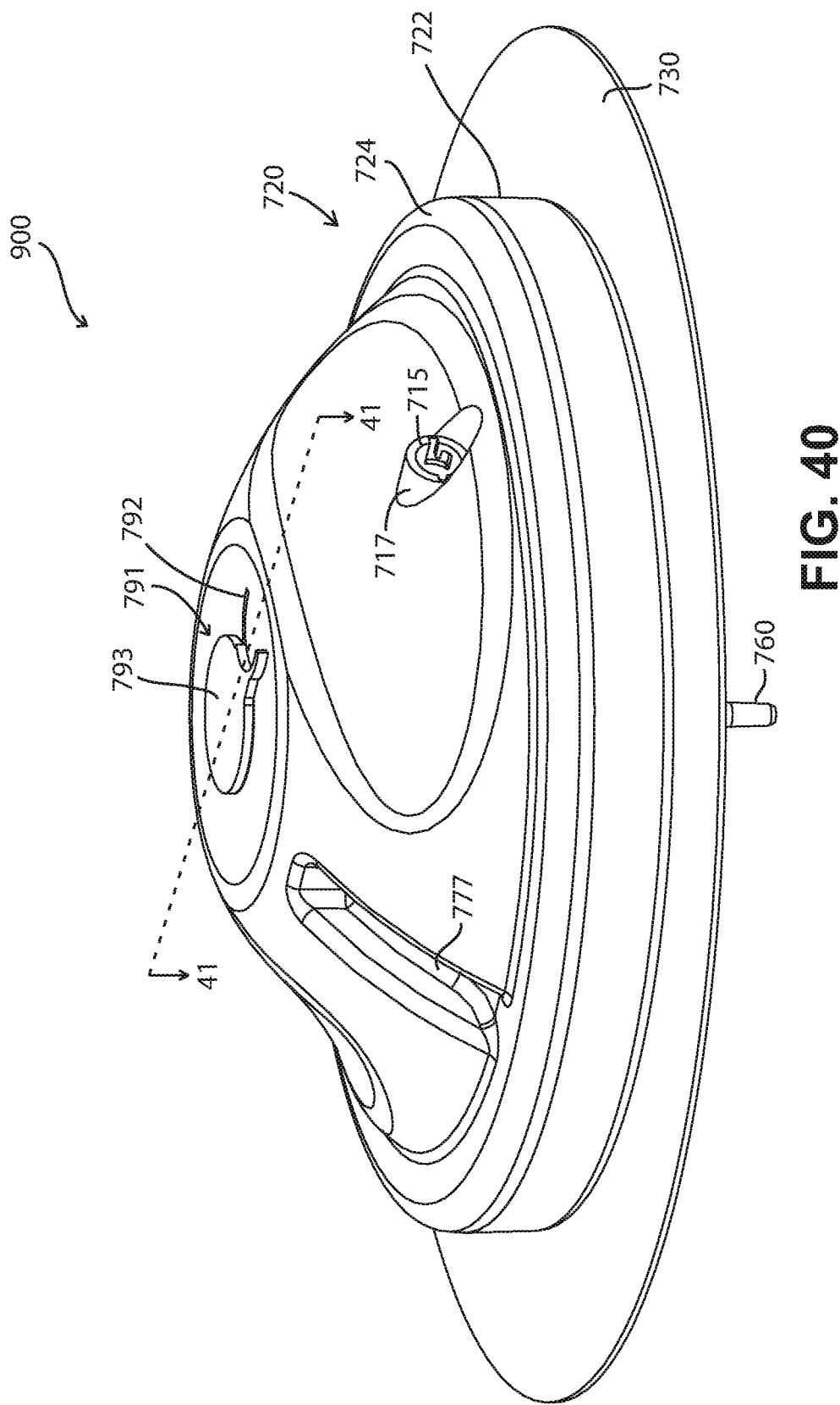
FIG. 40 is another perspective view of the FIG. 37 fluid delivery device, showing the passageway closing structure blocking flow into and through the centrally-oriented fluid delivery passageway.
Figure 41:
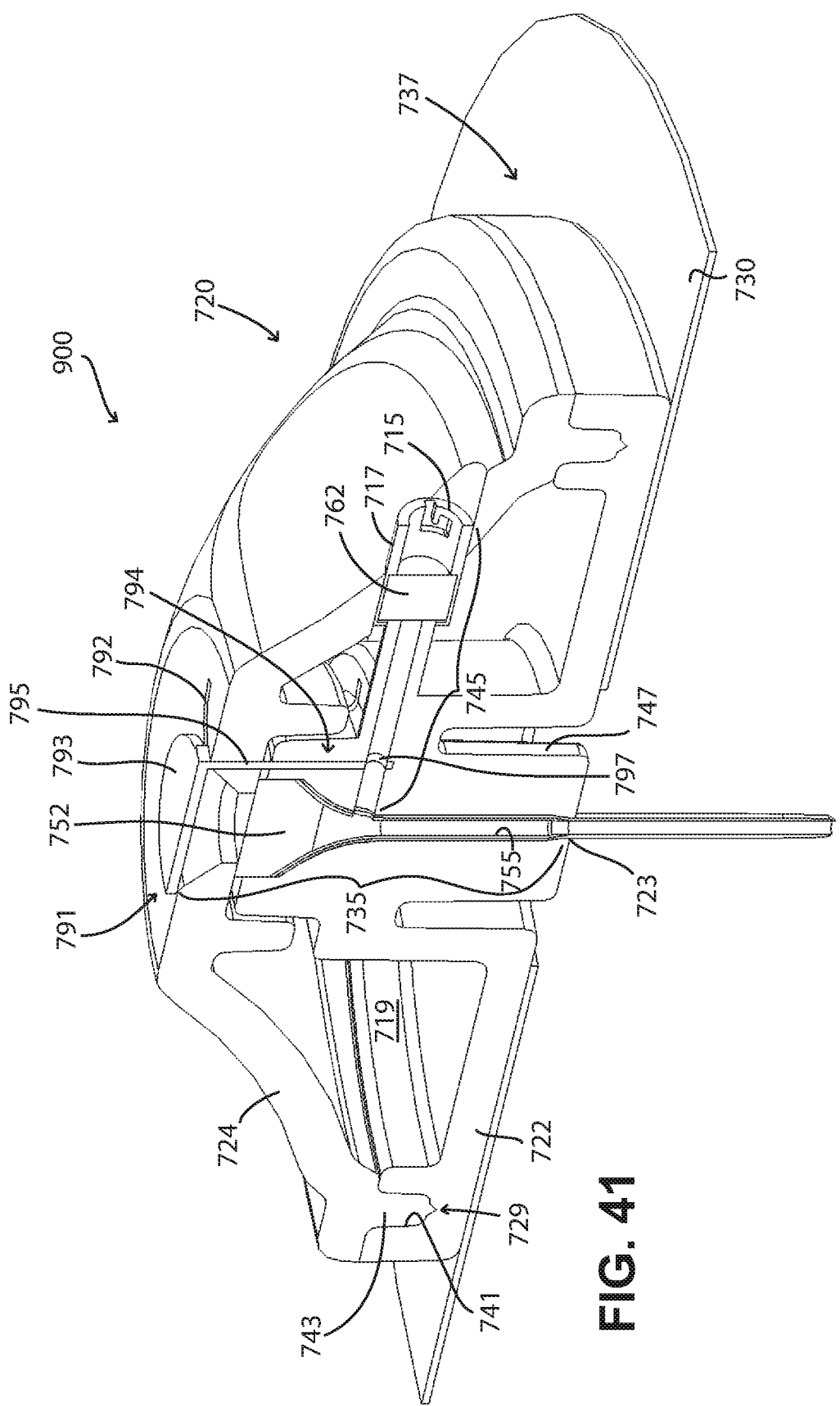
FIG. 41 is a perspective cross-sectional view (minus the cross-hatching), taken along line 41-41 in FIG. 40, showing how the opening in the passageway closing structure of the FIG. 37 fluid delivery device aligns with the laterally-oriented fluid delivery passageway.

FIGS. 40-43 illustrate how passageway closing structure 791 pivots, and the slots in the cap and base elements of body 720 that enable it to do so. FIG. 40 is another perspective view of fluid delivery device 900, and shows passageway closing structure 791 in a first position in which fluid flow into and through fluid delivery passageway 735 is blocked because passageway blocking cap 793 is covering inlet 705. FIG. 41 is a perspective cross-sectional view of device 900, taken along line 41-41 in FIG. 40. This figure shows that cap element 724 includes a slot 792, which in this embodiment is arcuate-shaped, that receives a portion of passageway blocking section 795 of structure 791. Base element includes a slot 794, which is also arcuate-shaped, that receives a lower portion of passageway blocking section 795.

In the first position shown in FIGS. 40 and 41, opening 797 of passageway blocking structure 791 is aligned with a portion of fluid delivery passageway 745, thus allowing fluid to flow through it, into a lower portion of fluid delivery passageway 735, and out of body 720. The fluid that flows through substantially unobstructed fluid delivery passageway 745 may be injected using a pump (not shown) that is coupled to device 900 through inlet fitting 717.

Figure 42:
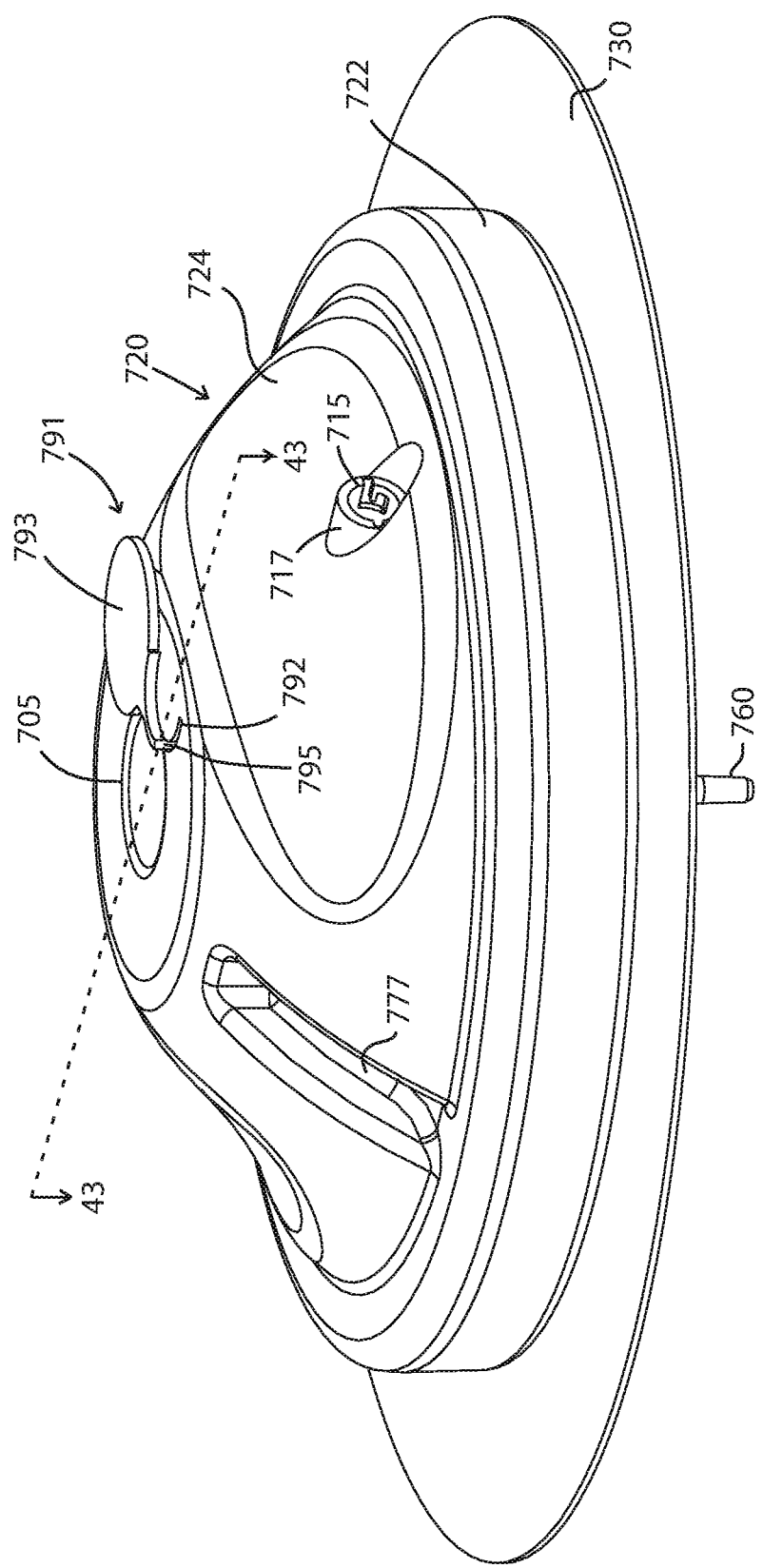
FIG. 42 is another perspective view of the FIG. 37 fluid delivery device, showing the passageway closing structure allowing flow into and through the centrally-oriented fluid delivery passageway.
Figure 43:
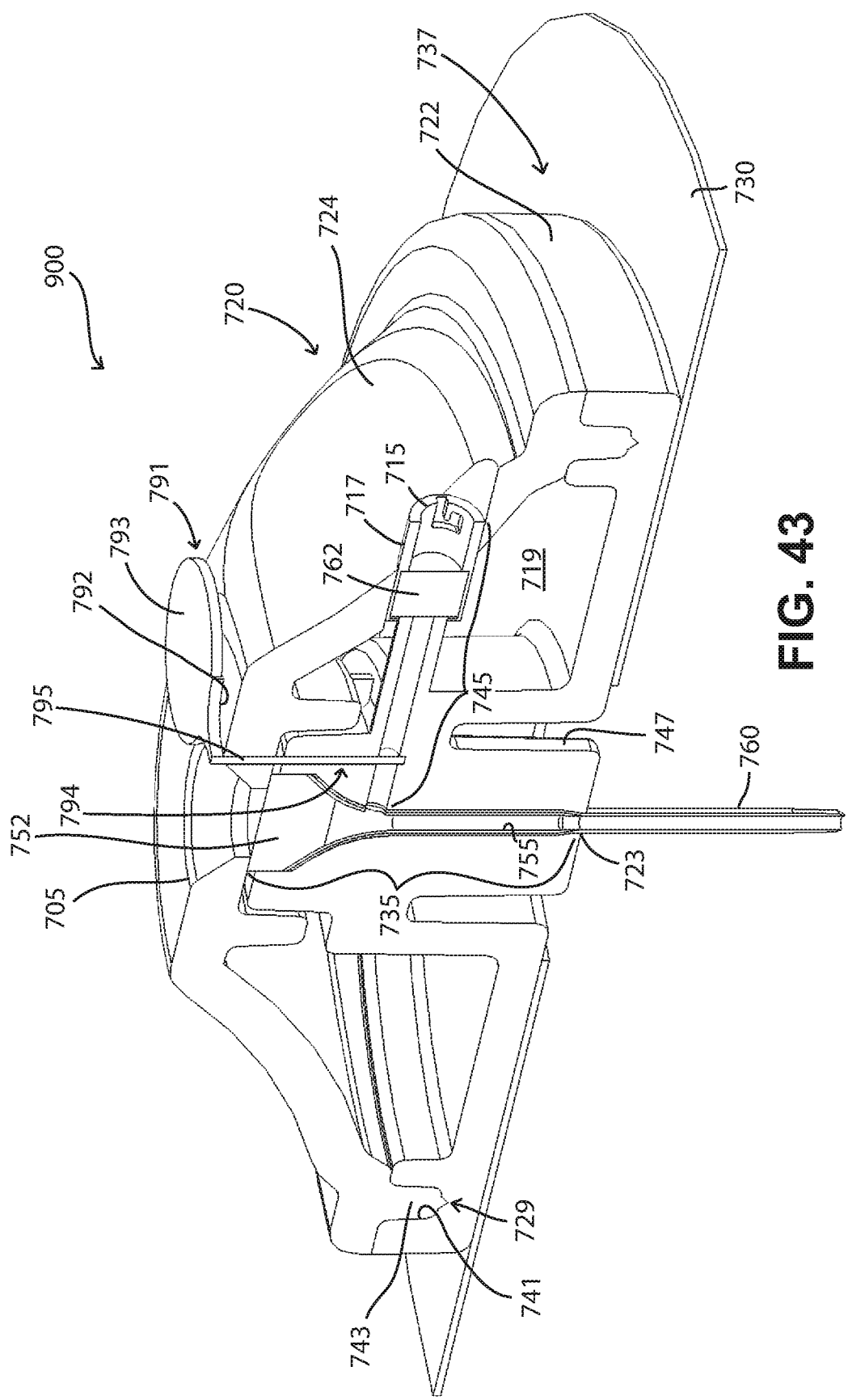
FIG. 43 is a perspective cross-sectional view (minus the cross-hatching), taken along line 43-43 in FIG. 42, showing how a portion of the passageway closing structure of the FIG. 37 fluid delivery device blocks flow through the laterally-oriented fluid delivery passageway and out of the body of the device.

In the second position shown in FIGS. 42 and 43, a portion of passageway blocking section 795 has been pivoted into the path of the portion of fluid delivery passageway 745 that was aligned with opening 797 in the first position. In addition, cap 793 has been pivoted out of the path of inlet 705. As a result, fluid can flow into and through fluid delivery passageway 735, but fluid cannot flow through fluid delivery passageway 745 and out of body 720. The axis (not shown) about which passageway blocking structure 791 pivots is substantially parallel to (a) an axis centered within a portion of fluid delivery passageway 735, and (b) the normal direction of insertion of device 900 into a living being.

The present fluid delivery systems may include on or more of the present fluid delivery devices that are sterilized (e.g., with ethylene oxide or gamma radiation) and sealed in a package, which may take the form of a pouch, tray, box (such as a box containing multiple trays), tube, or the like. The package may include instructions for use on the outside of the package or on material (e.g., a folded piece of paper) placed in the package. In some embodiments of systems that include a package containing multiple trays for resale, one set of instructions for use may be placed in the package. The systems also may include a vial or vials of fluid to be delivered to the user (such as insulin).

The materials from which the elements of the present fluid delivery devices may be made should be biocompatible. The septa that may be used with some embodiments of the present fluid delivery devices may be characterized as self-sealing septa, or resealing septa, and may be made from a resilient material. One example of a suitable material for such septa is silicone elastomer, which may be described as an elastomeric material, although other materials may be used. If the injection structure chosen to inject fluid into a given embodiment of the present fluid delivery devices is an injection needle, the injection needle used should be sized such that the septum will reseal when the needle is withdrawn. For example, the needle size should be chosen in light of the septum material and the radial pressure the needle will exert on the septum material it contacts such that the needle does not leave a septum opening when withdrawn that is large enough for fluid to leak upstream through it.

The bodies of the present fluid delivery devices (e.g., both the caps and bases of the two-element bodies) may be made from many different materials, such as any suitable medical grade plastic. The insertion hubs (or handles) (e.g., insertion hub 74) of the present fluid delivery devices that include them also may be made, for example, from any suitable medical grade plastic. The insertion structures (e.g., insertion needle 72) of the present fluid delivery devices that include them may be made from any suitable material, such as stainless steel or a suitably rigid polymer. The needle guides (e.g., needle guide 50) of the present fluid delivery devices that include them may be made from any suitable material, such as stainless steel, although other materials may be used. The embodiments of the present needle guides that are made from metal, such as an alloy, may be characterized as metal needle guides. The soft cannulas (e.g., cannula 60) of the present fluid delivery devices that include them may be made from many different materials, such as any suitable medical grade plastic. Those that are not made from metal may be characterized as non-rigid cannulas or non-metal cannulas.

The needle guards (e.g., needle guard 80) of the present fluid delivery devices that include them may be made from many different materials, such as any suitable medical grade plastic. The adhesive layers or pads (e.g., adhesive layer 30) of the present fluid delivery devices that include them may be made from any suitable material, and any adhesive that is used may include an anti-bacterial and/or healing promotion substance (such as dexamethasone, or the like) that reduces the risk of infection and speeds the healing process once the fluid delivery device is removed from the user. The rigid cannulas (e.g., cannula 260) of the present fluid delivery devices that include them may be made from any suitable material—such as stainless steel, any suitable alloy or any suitably rigid polymer. Versions of the present rigid cannulas that are made from metal may (in such embodiments) be characterized as metal cannulas.

If a medical grade plastic is used for one of the elements discussed above, the material chosen may, be translucent, transparent, semi-transparent, or opaque in different embodiments.

Embodiments of the present fluid delivery devices that use a soft cannula may be inserted using any well-known and appropriately configured insertion device, such as the insertion devices shown in FIGS. 1-4. Inserting one of the present fluid delivery devices into a user using only such an insertion device may be characterized as non-spring driven insertion, or insertion using force applied directly by hand. Other suitable insertion devices include those that are triggered by releasing the potential force built up in a compressed spring. Insertion using a spring-driven device may be characterized as spring-driven insertion. Some embodiments of such devices may be used with the insertion device shown in FIGS. 1-4 to achieve insertion of one of the present fluid delivery devices into a user. Still other insertion devices could be computer-controlled. Other forces that may be used to insert one of the present fluid delivery device into a user include pneumatic and hydraulic forces. In general, insertion of the embodiments of the present insertion devices that include non-rigid cannulas without any reinforcing coating should be relatively quick and forceful to reduce the chance of the cannula crimping or bending during insertion. The insertion of embodiments that include a rigid cannula or a non-rigid cannula that has been reinforced in some manner may be achieved more slowly and, in some cases, with less force.

As an alternative to the use of insertion devices with needles for inserting embodiments of the present fluid delivery devices that have a non-rigid cannula, an outer surface of the exposed portion of the cannula may be coated with a fluid soluble coating that provides a sharp tip, or point, at the end of the cannula, but that dissolves in the bodily fluids of the user after insertion. Such a coating is described in paragraphs 0035 to 0045 of U.S. Patent Application Pub. No. 2002/0072720, which paragraphs are incorporated by reference.

Different injection devices may be used to facilitate the delivery of fluid to, for example, the subcutaneous tissue of a user. For example, a standard syringe and syringe needle may be used. The syringe needle may be sharp and open at its end, sharp and open somewhere along its shaft other than at its end, blunt and open at its end, or blunt and open somewhere along its shaft other than at its end. Other suitable injection devices include pen-like devices having some sort of needle that is generally concealed. Injection of fluid into a patient using one of these injection devices may be characterized as delivering fluid to a user from a non-pump source, or delivering fluid to a user from a source that is not connected to a pump. In other embodiments of the present devices, systems and methods, a pump may be used in the fluid delivery process. For example, this is true of the fluid delivery devices that include an inlet fitting such as inlet fitting 717.

While the target tissue of a patient may be pinched and/or pulled outwardly from the body slightly to isolate it, insertion of one of the present fluid delivery devices into the tissue of a user still may, in some embodiments, be characterized as being at a substantially perpendicular angle to a target skin location of a user/living being because the rigid cannula or non-rigid cannula and insertion structure will enter the user's tissue at an angle that is substantially perpendicular to the plane in which the target tissue lies.

Some embodiments of the present methods include the use of the insertion and/or injection techniques described above.

The present fluid delivery devices, systems and methods are not intended to be limited to the particular forms disclosed. Rather, they include all modifications, equivalents, and alternatives falling within the scope of the claims. For example, the cap elements of the multi-element embodiments that include them can have configurations other than those depicted in the figures. Such cap elements may have an inlet that is not circular (e.g., the inlet may be rectangular, hexagonal, or octagonal), and the wall of the portion of the cap element that forms the upper portion of a given fluid delivery passageway may be straight-walled, may have a taper of constant angle, or may have a taper of non-constant angle.

As another example, multiple cannulas may extend from and be coupled to a body of one of the present fluid delivery devices such that the delivery of medication may be spread to different areas of a user's tissue. For example, a single inlet may be in fluid communication with multiple cannulas positioned to delivery fluid to a target tissue location; alternatively, a body may have multiple inlets, each of which is in fluid communication with a cannula positioned to deliver fluid to a target tissue location.

As another example, in some embodiments of the present fluid delivery systems, the package containing one or more of the present fluid delivery devices also may include one or more capsules, or vials, containing a prescribed amount of fluid. The package also may include a pump and associated tubing for coupling to a fitting such an inlet fitting 717.

As another example, some embodiments of the present fluid delivery devices that include a fluid delivery passageway having a portion oriented at an angle that is not parallel to the normal direction of insertion of the device may have only one inlet (although two inlets are illustrated in FIGS. 27 and 31, for example). Some embodiments of such a device may include a rigid cannula having a sharp end, and the cannula may be oriented with respect to the body as shown, for example, in FIG. 18. Some embodiments of such a device also may include only one fluid delivery passageway that includes a portion angled at a non-parallel angle to the normal direction of insertion device and another portion angled parallel to the normal direction of insertion.

As another example, an upper portion of a given fluid delivery passageway (including the inlet) may be set at an angle other than parallel to an intended direction of insertion for the device. Similarly, any portion of the cannula that is exposed when not inserted into a user (no such portions are shown in the figures, but may exist) may be set at a non-parallel angle to an intended direction of insertion for the device.

As another example, the needle guides shown in the figures are configured such that at least some open space exists below the bottommost portion of the septum positioned within the needle guide and above the beginning of the straight-walled portion of the needle guide. In other embodiments, the bottommost portion of the septum positioned within the needle guide may extend even further downstream such that there is less such open space than what is shown in the figures down to no such open space. In some embodiments of the present fluid delivery devices, one may want to put the length (or thickness) of the septum in compression to cause the septum to exert a radial force on the needle guide that tends to restrict upstream and downstream movement of the septum relative to the needle guide. Having at least some open space beneath the bottommost portion of the septum and the uppermost portion of the straight-walled portion of the needle guide may facilitate such compression.

The claims are not to be interpreted as including means-plus- or step-plus-function limitations, unless such a limitation is explicitly recited in a given claim using the phrase(s) "means for" or "step for," respectively.

The invention claimed is:

1. A fluid delivery device comprising:
   a body having a first fluid delivery passageway and a second fluid delivery passageway intersecting the first fluid delivery passageway, wherein the first fluid delivery passageway is fed by an inlet port adapted for engagement with an infusion pump connector fitting;
   a cannula having a portion that is coaxial with the first fluid delivery passageway, the cannula also having a cannula passageway having an internal width;
   a needle guide having a portion positioned within the second fluid delivery passageway and defining a needle guide passageway therethrough;
   a septum having a portion positioned within the needle guide, the septum also having an accessible portion that is accessible to an injection needle during normal use of the fluid delivery device, the accessible portion having a width that is at least twice as great as the internal width of the cannula, and
   a passageway closing structure oriented in a first position that at least partially prevents fluid from flowing through the first fluid delivery passageway while allowing fluid to flow unobstructed through the second fluid delivery passageway, the passageway closing structure being movable to a second position that at least partially prevents fluid from flowing through the second fluid delivery passageway while allowing fluid to flow unobstructed through the first fluid delivery passageway,
   wherein the passageway closing structure is positioned at least partially within the needle guide passageway while in the first position but not within the needle guide passageway while in the second position.

2. The fluid delivery device of claim 1 configured such that fluid exiting the fluid delivery device into a living being must exit from the cannula.

3. The fluid delivery device of claim 1, wherein the cannula is in fluid communication with the each of the first and second fluid delivery passageways.

4. The fluid delivery device of claim 1, wherein the first fluid delivery passageway and the second fluid delivery passageway intersect at a non-perpendicular angle.

5. The fluid delivery device of claim 1, further comprising an adhesive layer attached to the body.

6. The fluid delivery device of claim 5, wherein the first fluid delivery passageway is closer to being parallel with the adhesive layer than to being perpendicular to the adhesive layer.

7. The fluid delivery device of claim 1, wherein a length of at least one of the first fluid delivery passageway or the second fluid delivery passageway is greater than a height of the body.

8. A fluid delivery device comprising:
   a body having a first fluid delivery passageway and a second fluid delivery passageway, wherein the first fluid delivery passageway is fed by an inlet port adapted for engagement with an infusion pump connector fitting;
   a cannula fluidically coupled to each of the first fluid delivery passageway and the second fluid delivery passageway, the cannula having a cannula passageway having a smallest internal width, the cannula being coaxial with one of the first or second fluid delivery passageways;
   a needle guide having a portion positioned within the other of the first or second fluid delivery passageways and defining a needle guide passageway therethrough; and
   a septum having a portion positioned within the needle guide, the septum also having an accessible portion that is accessible to an injection needle during normal use of the fluid delivery device, the accessible portion having a greatest width that is at least twice as great as the smallest internal width of the cannula;
   a passageway closing structure configured to be oriented in a first position that at least partially prevents fluid from flowing through the first fluid delivery passageway while allowing fluid to flow unobstructed through the second fluid delivery passageway, the passageway closing structure movable to a second position that at least partially prevents fluid from flowing through the second fluid delivery passageway while allowing fluid to flow unobstructed through the first fluid delivery passageway,
   wherein the passageway closing structure is positioned at least partially within the needle guide passageway while in the first position but not within the needle guide passageway while in the second position.

9. The fluid delivery device of claim 8, wherein the first and second fluid delivery passageways are oriented along intersecting axes.

10. The fluid delivery device of claim 9, wherein the intersecting axes are oriented at a non-perpendicular angle.

11. The fluid delivery device of claim 8, further comprising an adhesive layer attached to the body.

12. The fluid delivery device of claim 11, wherein the first fluid delivery passageway is closer to being parallel with the adhesive layer than to being perpendicular to the adhesive layer.

13. The fluid delivery device of claim 8, wherein a length of at least one of the first fluid delivery passageway or the second fluid delivery passageway is greater than a height of the body.

14. The fluid delivery device of claim 8, wherein the cannula is positioned at least partially within the first fluid delivery passageway.

15. The fluid delivery device of claim 8, wherein the device is configured such that fluid exiting the fluid delivery device into a living being must exit from the cannula.

16. A fluid delivery device comprising:
   a body having two fluid delivery passageways;
   a cannula having a portion that is coaxial with a portion of one of the two fluid delivery passageways, the cannula also having a cannula passageway having a smallest internal width;
   a needle guide having a portion positioned within one of the fluid delivery passageways and defining a needle guide passageway therethrough;
   a septum having a portion positioned within the needle guide, the septum also having an accessible portion that is accessible to an injection needle during normal use of the fluid delivery device, the accessible portion having a greatest width that is at least twice as great as the smallest internal width of the cannula; and
   a passageway closing structure movable between a first position that at least partially prevents fluid from flowing through the first fluid delivery passageway while allowing fluid to flow unobstructed through the second fluid delivery passageway and a second position that at least partially prevents fluid from flowing through the second fluid delivery passageway while allowing fluid to flow unobstructed through the first fluid delivery passageway, wherein the passageway closing structure is positioned at least partially within the needle guide passageway while in one of the first position or the second position but not within the needle guide passageway while in the other of the first position or the second position.

\* \* \* \* \*

UNITED STATES PATENT AND TRADEMARK OFFICE
CERTIFICATE OF CORRECTION

| | |
|---|---|
| PATENT NO. | : 11,771,823 B2 |
| APPLICATION NO. | : 16/460565 |
| DATED | : October 3, 2023 |
| INVENTOR(S) | : Turner et al. |

It is certified that error appears in the above-identified patent and that said Letters Patent is hereby corrected as shown below:

In the Claims

In Column 27, in Claim 1, Line 26, delete "cannula," and insert -- cannula; --, therefor.

Signed and Sealed this
Fourteenth Day of November, 2023

Katherine Kelly Vidal
*Director of the United States Patent and Trademark Office*